(12) United States Patent
Valentine et al.

(10) Patent No.: US 11,950,971 B2
(45) Date of Patent: *Apr. 9, 2024

(54) SURGICAL DEVICES WITH MOISTURE CONTROL

(71) Applicant: Covidien LP, Mansfield, MA (US)

(72) Inventors: David E. Valentine, Hamden, CT (US); Joseph Eisinger, Northford, CT (US); Patrick Mozdzierz, Glastonbury, CT (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/894,208

(22) Filed: Aug. 24, 2022

(65) Prior Publication Data

US 2022/0409330 A1 Dec. 29, 2022

Related U.S. Application Data

(63) Continuation of application No. 16/826,928, filed on Mar. 23, 2020, now Pat. No. 11,432,902, which is a
(Continued)

(51) Int. Cl.
*A61B 90/70* (2016.01)
*B08B 3/04* (2006.01)
(Continued)

(52) U.S. Cl.
CPC ............... *A61B 90/70* (2016.02); *B08B 3/04* (2013.01); *B08B 9/00* (2013.01); *A61B 2017/00292* (2013.01); *A61B 2017/0042* (2013.01); *A61B 17/1155* (2013.01); *A61B 2017/3437* (2013.01); *A61B 2034/301* (2016.02); *A61B 2090/701* (2016.02)

(58) Field of Classification Search
CPC .................................. A61B 90/70; B08B 3/04
See application file for complete search history.

(56) References Cited

U.S. PATENT DOCUMENTS 2,957,353 A 10/1960 Babacz
3,111,328 A 11/1963 Di Rito et al.
(Continued)

FOREIGN PATENT DOCUMENTS

CA 2451558 A1 1/2003
CN 1547454 A 11/2004
(Continued)

OTHER PUBLICATIONS

Extended European Search Report corresponding to International Application No. EP 14 18 4882.0 dated May 12, 2015.
(Continued)

*Primary Examiner* — Nathaniel C Chukwurah
(74) *Attorney, Agent, or Firm* — Carter, DeLuca & Farrell LLP

(57) ABSTRACT

A surgical device including a handle assembly, an elongated portion, an end effector, a drive shaft, and a wick is disclosed. The wick is disposed within an outer sleeve of the elongated portion and is made from a fibrous material. The wick is configured to transfer moisture from a first portion of the wick to a second portion of the wick.

20 Claims, 54 Drawing Sheets

Related U.S. Application Data continuation-in-part of application No. PCT/US2019/045049, filed on Aug. 5, 2019, which is a continuation-in-part of application No. 14/991,157, filed on Jan. 8, 2016, now Pat. No. 10,327,779.

(60) Provisional application No. 62/834,759, filed on Apr. 16, 2019, provisional application No. 62/718,065, filed on Aug. 13, 2018, provisional application No. 62/718,079, filed on Aug. 13, 2018, provisional application No. 62/718,089, filed on Aug. 13, 2018, provisional application No. 62/718,450, filed on Aug. 14, 2018, provisional application No. 62/718,102, filed on Aug. 13, 2018, provisional application No. 62/145,759, filed on Apr. 10, 2015.

(51) Int. Cl.
*B08B 9/00* (2006.01)
*A61B 17/00* (2006.01)
*A61B 17/115* (2006.01)
*A61B 17/34* (2006.01)
*A61B 34/30* (2016.01)

(56) References Cited

U.S. PATENT DOCUMENTS

| | | |
|---|---|---|
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,433,721 A | 7/1995 | Hooven et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,626,587 A | 5/1997 | Bishop et al. |
| 5,632,432 A | 5/1997 | Schulze et al. |
| 5,645,209 A | 7/1997 | Green et al. |
| 5,647,526 A | 7/1997 | Green et al. |
| 5,653,374 A | 8/1997 | Young et al. |
| 5,658,300 A | 8/1997 | Bito et al. |
| 5,662,662 A | 9/1997 | Bishop et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,792,573 A | 8/1998 | Pitzen et al. |
| 5,797,536 A | 8/1998 | Smith et al. |
| 5,820,009 A | 10/1998 | Melling et al. |
| 5,863,159 A | 1/1999 | Lasko |
| 5,865,361 A | 2/1999 | Milliman et al. |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,422,729 B1 | 7/2002 | Rohrbach et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,860,892 B1 | 3/2005 | Tanaka et al. |
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |

(56) References Cited

U.S. PATENT DOCUMENTS

| | | |
|---|---|---|
| 7,140,528 B2 | 11/2006 | Shelton, IV |
| 7,141,049 B2 | 11/2006 | Stern et al. |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,252,660 B2 | 8/2007 | Kunz |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,900,805 B2 | 3/2011 | Shelton, IV et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,011,550 B2 | 9/2011 | Aranyi et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,056,787 B2 | 11/2011 | Boudreaux et al. |
| 8,114,118 B2 | 2/2012 | Knodel et al. |
| 8,127,975 B2 | 3/2012 | Olson et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,303,581 B2 | 11/2012 | Arts et al. |
| 8,342,379 B2 | 1/2013 | Whitman et al. |
| 8,348,130 B2 | 1/2013 | Shah et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,403,926 B2 | 3/2013 | Nobis et al. |
| 8,403,949 B2 | 3/2013 | Palmer et al. |
| 8,418,904 B2 | 4/2013 | Wenchell et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,523,043 B2 | 9/2013 | Ullrich et al. |
| 8,551,076 B2 | 10/2013 | Duval et al. |
| 8,561,871 B2 | 10/2013 | Rajappa et al. |
| 8,561,874 B2 | 10/2013 | Scirica |
| 8,590,763 B2 | 11/2013 | Milliman |
| 8,602,287 B2 | 12/2013 | Yates et al. |
| 8,623,000 B2 | 1/2014 | Humayun et al. |
| 8,627,995 B2 | 1/2014 | Smith et al. |
| 8,632,463 B2 | 1/2014 | Drinan et al. |
| 8,636,766 B2 | 1/2014 | Milliman et al. |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,715,306 B2 | 5/2014 | Faller et al. |
| 8,752,749 B2 | 6/2014 | Moore et al. |
| 8,758,391 B2 | 6/2014 | Swayze et al. |
| 8,806,973 B2 | 8/2014 | Ross et al. |
| 8,808,311 B2 | 8/2014 | Heinrich et al. |
| 8,820,605 B2 | 9/2014 | Shelton, IV |
| 8,828,023 B2 | 9/2014 | Neff et al. |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,905,289 B2 | 12/2014 | Patel et al. |
| 8,919,630 B2 | 12/2014 | Milliman |
| 8,931,680 B2 | 1/2015 | Milliman |
| 8,939,344 B2 | 1/2015 | Olson et al. |
| 8,950,646 B2 | 2/2015 | Viola |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,016,545 B2 | 4/2015 | Aranyi et al. |

(56) References Cited

U.S. PATENT DOCUMENTS

| | | |
|---|---|---|
| 9,023,014 B2 | 5/2015 | Chowaniec et al. |
| 9,033,868 B2 | 5/2015 | Whitman et al. |
| 9,055,943 B2 | 6/2015 | Zemlok et al. |
| 9,064,653 B2 | 6/2015 | Prest et al. |
| 9,072,515 B2 | 7/2015 | Hall et al. |
| 9,113,847 B2 | 8/2015 | Whitman et al. |
| 9,113,875 B2 | 8/2015 | Viola et al. |
| 9,113,876 B2 | 8/2015 | Zemlok et al. |
| 9,113,899 B2 | 8/2015 | Garrison et al. |
| 9,216,013 B2 | 12/2015 | Scirica et al. |
| 9,241,712 B2 | 1/2016 | Zemlok et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 9,579,099 B2 | 2/2017 | Penna et al. |
| 11,432,902 B2 * | 9/2022 | Valentine ............ A61B 90/70 |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0034369 A1 | 2/2004 | Sauer et al. |
| 2004/0111012 A1 | 6/2004 | Whitman |
| 2004/0133189 A1 | 7/2004 | Sakurai |
| 2004/0153124 A1 | 8/2004 | Whitman |
| 2004/0176751 A1 | 9/2004 | Weitzner et al. |
| 2004/0193146 A1 | 9/2004 | Lee et al. |
| 2005/0125027 A1 | 6/2005 | Knodel et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2006/0278680 A1 | 12/2006 | Viola et al. |
| 2006/0284730 A1 | 12/2006 | Schmid et al. |
| 2007/0023476 A1 | 2/2007 | Whitman et al. |
| 2007/0023477 A1 | 2/2007 | Whitman et al. |
| 2007/0027469 A1 | 2/2007 | Smith et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0270784 A1 | 11/2007 | Smith et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0147089 A1 | 6/2008 | Loh et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0012533 A1 | 1/2009 | Barbagli et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209946 A1 | 8/2009 | Swayze et al. |
| 2009/0209990 A1 | 8/2009 | Yates et al. |
| 2009/0254094 A1 | 10/2009 | Knapp et al. |
| 2009/0299141 A1 | 12/2009 | Downey et al. |
| 2010/0023022 A1 | 1/2010 | Zeiner et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0006101 A1 | 1/2011 | Hall et al. |
| 2011/0017801 A1 | 1/2011 | Zemlok et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0152776 A1 | 6/2011 | Hartoumbekis et al. |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174009 A1 | 7/2011 | Iizuka et al. |
| 2011/0174099 A1 | 7/2011 | Ross et al. |
| 2011/0184245 A1 | 7/2011 | Xia et al. |
| 2011/0204119 A1 | 8/2011 | McCuen |
| 2011/0218522 A1 | 9/2011 | Whitman |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0211542 A1 | 8/2012 | Racenet |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0093149 A1 | 4/2013 | Saur et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0365235 A1 | 12/2014 | DeBoer et al. |
| 2014/0373652 A1 | 12/2014 | Zergiebel et al. |
| 2015/0014392 A1 | 1/2015 | Williams et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0108201 A1 | 4/2015 | Williams |
| 2015/0112381 A1 | 4/2015 | Richard |
| 2015/0122870 A1 | 5/2015 | Zemlok et al. |
| 2015/0133224 A1 | 5/2015 | Whitman et al. |

(56) References Cited

U.S. PATENT DOCUMENTS

| | | | |
|---|---|---|---|
| 2015/0142031 A1 | 5/2015 | Faller et al. | |
| 2015/0150547 A1 | 6/2015 | Ingmanson et al. | |
| 2015/0150574 A1 | 6/2015 | Richard et al. | |
| 2015/0157320 A1 | 6/2015 | Zergiebel et al. | |
| 2015/0157321 A1 | 6/2015 | Zergiebel et al. | |
| 2015/0164502 A1 | 6/2015 | Richard et al. | |
| 2015/0201931 A1 | 7/2015 | Zergiebel et al. | |
| 2015/0272577 A1 | 10/2015 | Zemlok et al. | |
| 2015/0297199 A1 | 10/2015 | Nicholas et al. | |
| 2015/0303996 A1 | 10/2015 | Calderoni | |
| 2015/0320420 A1 | 11/2015 | Penna et al. | |
| 2015/0327850 A1 | 11/2015 | Kostrzewski | |
| 2015/0342601 A1 | 12/2015 | Williams et al. | |
| 2015/0342603 A1 | 12/2015 | Zergiebel et al. | |
| 2015/0351776 A1* | 12/2015 | Swayze | A61B 17/12177 600/249 |
| 2015/0374366 A1 | 12/2015 | Zergiebel et al. | |
| 2015/0374370 A1 | 12/2015 | Zergiebel et al. | |
| 2015/0374371 A1 | 12/2015 | Richard et al. | |
| 2015/0374372 A1 | 12/2015 | Zergiebel et al. | |
| 2015/0374449 A1 | 12/2015 | Chowaniec et al. | |
| 2015/0380187 A1 | 12/2015 | Zergiebel et al. | |
| 2016/0095585 A1 | 4/2016 | Zergiebel et al. | |
| 2016/0095596 A1 | 4/2016 | Scirica et al. | |
| 2016/0106406 A1 | 4/2016 | Cabrera et al. | |
| 2016/0113648 A1 | 4/2016 | Zergiebel et al. | |
| 2016/0113649 A1 | 4/2016 | Zergiebel et al. | |
| 2017/0005598 A1 | 1/2017 | Schulze-Icking-Konert | |
| 2017/0055981 A1* | 3/2017 | Vendely | A61B 17/07292 |

FOREIGN PATENT DOCUMENTS

| | | |
|---|---|---|
| CN | 1957854 A | 5/2007 |
| CN | 101495046 A | 7/2009 |
| CN | 101856251 A | 10/2010 |
| CN | 105982703 A | 10/2016 |
| CN | 106901788 A | 6/2017 |
| DE | 102008053842 A1 | 5/2010 |
| EP | 0705571 A1 | 4/1996 |
| EP | 1563793 A1 | 8/2005 |
| EP | 1759652 A2 | 3/2007 |
| EP | 1769754 A1 | 4/2007 |
| EP | 1908412 A2 | 4/2008 |
| EP | 1917929 A1 | 5/2008 |
| EP | 1952769 A2 | 8/2008 |
| EP | 2090247 A1 | 8/2009 |
| EP | 2245994 A1 | 11/2010 |
| EP | 2316345 A1 | 5/2011 |
| EP | 2377472 A1 | 10/2011 |
| EP | 2668910 A2 | 12/2013 |
| EP | 2815705 A1 | 12/2014 |
| ES | 2333509 A1 | 2/2010 |
| FR | 2861574 A1 | 5/2005 |
| IN | 102247182 A | 11/2011 |
| JP | 2005125075 A | 5/2005 |
| JP | 2010240422 A | 10/2010 |
| KR | 20120022521 A | 3/2012 |
| WO | 2011108840 A2 | 9/2011 |
| WO | 2012040984 A1 | 4/2012 |
| WO | 2020036757 A2 | 2/2020 |

OTHER PUBLICATIONS

Canadian Office Action corresponding to International Application No. CA 2640399 dated May 7, 2015.
Japanese Office Action corresponding to International Application No. JP 2011-197365 dated Mar. 23, 2015.
Japanese Office Action corresponding to International Application No. JP 2011-084092 dated May 20, 2015.
Japanese Office Action corresponding to International Application No. JP 2014-148482 dated Jun. 2, 2015.
Extended European Search Report corresponding to International Application No. EP 14 18 9358.6 dated Jul. 8, 2015.
Extended European Search Report corresponding to International Application No. EP 14 19 6148.2 dated Apr. 23, 2015.
Partial European Search Report corresponding to International Application No. EP 14 19 6704.2 dated May 11, 2015.
Australian Office Action corresponding to International Application No. AU 2010241367 dated Aug. 20, 2015.
Partial European Search Report corresponding to International Application No. EP 14 19 9783.3 dated Sep. 3, 2015.
Extended European Search Report corresponding to International Application No. EP 15 16 9962.6 dated Sep. 14, 2015.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Chinese Office Action corresponding to counterpart Int'l Appln. No. CN 201310369318.2 dated Jun. 28, 2016.
Chinese Office Action (with English translation), dated Jul. 4, 2016, corresponding to Chinese Patent Application No. 2015101559718; 23 total pages.
European Search Report EP 15 156 035.6 dated Aug. 10, 2016.
European Search Report corresponding to EP 15 184 915.5-1654 dated Sep. 16, 2016.
Australian Examination Report No. 1 corresponding to International Application No. AU 2013205872 dated Oct. 19, 2016.
Australian Examination Report from Appl. No. AU 2013205840 dated Nov. 3, 2016.

(56) References Cited

OTHER PUBLICATIONS

Notification of Transmittal of the International Search Report and The Written Opinion of the International Searching Authority issued in corresponding application No. PCT/US2016/027042 dated Jul. 12, 2016.
Extended European Search Report dated Sep. 8, 2020 corresponding to counterpart Patent Application EP 20169691.1.
Japanese Office Action dated Dec. 4, 2023, issued in corresponding JP Appln. No. 2020102902547, 7 pages.
Japanese Office Action dated Dec. 15, 2023, issued in corresponding JP Appln. No. 2020072682, 4 pages.
European Office Action dated Feb. 6, 2024, issued in corresponding EP Appln. No. 20169691, 7 pages.

* cited by examiner

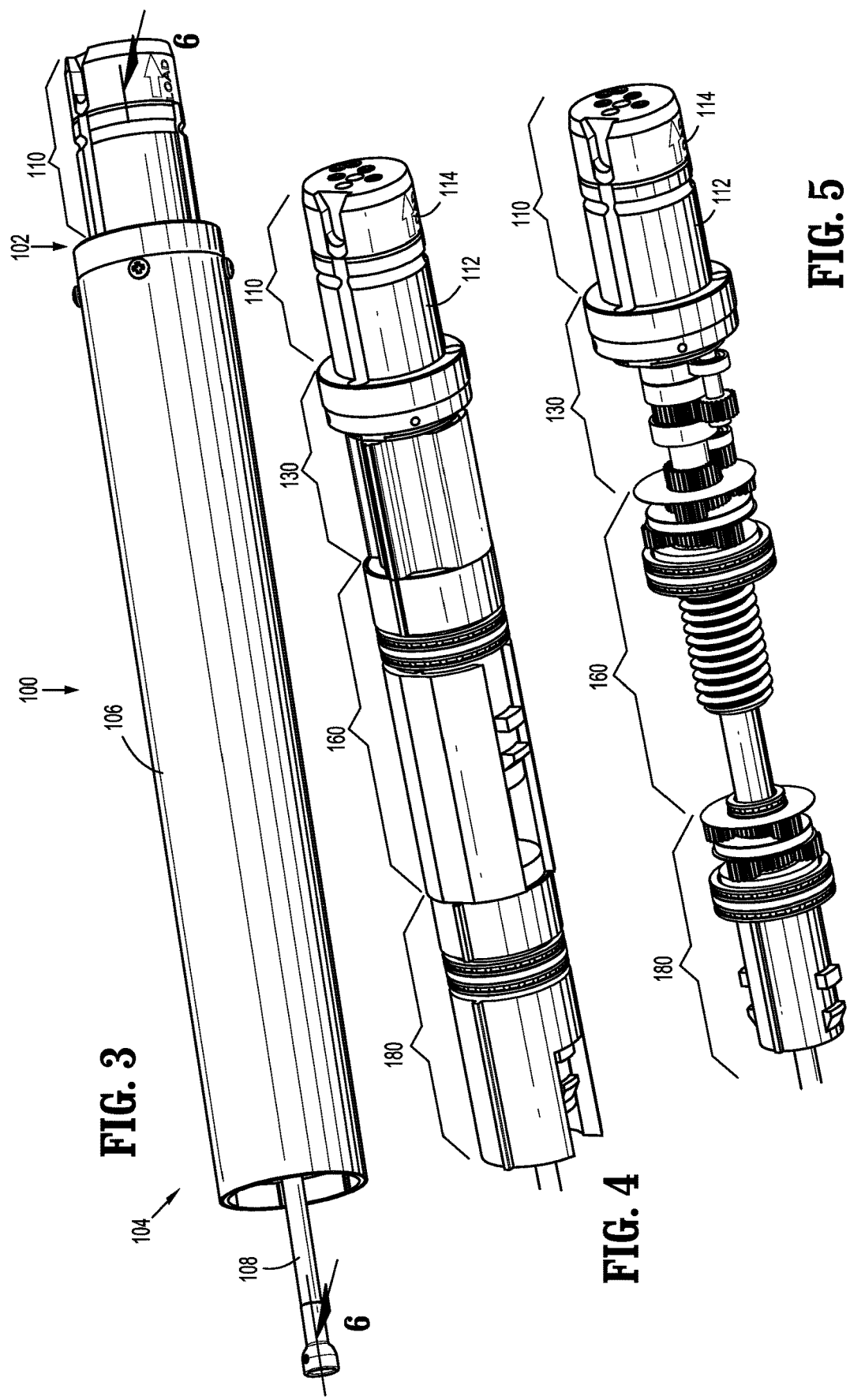

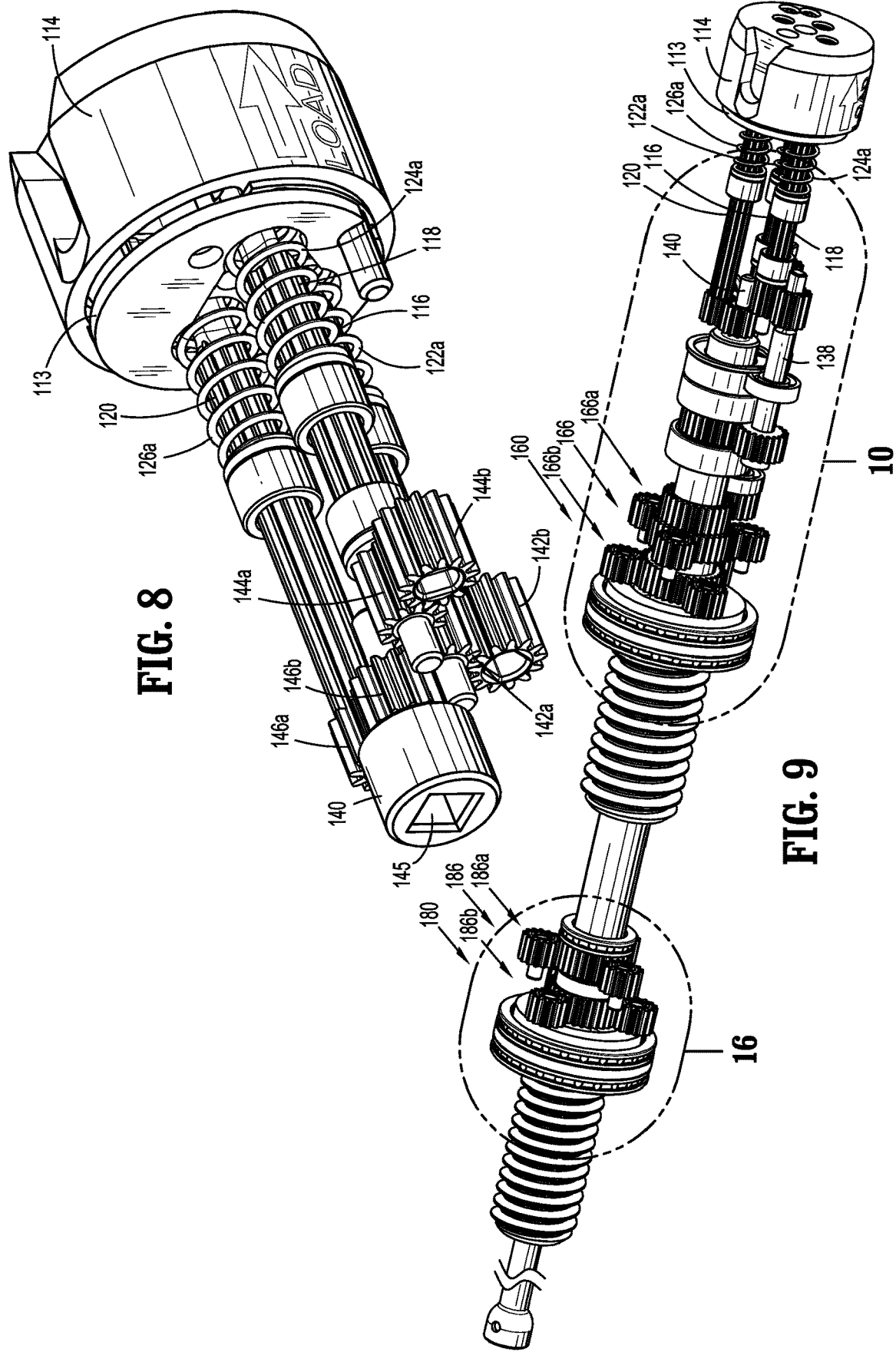

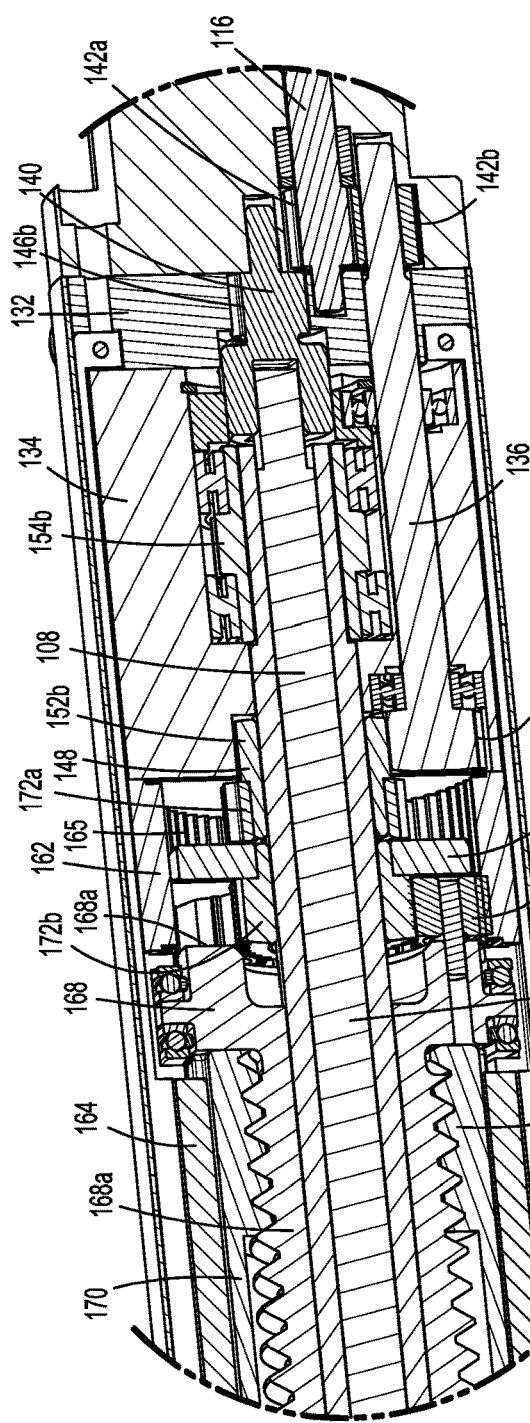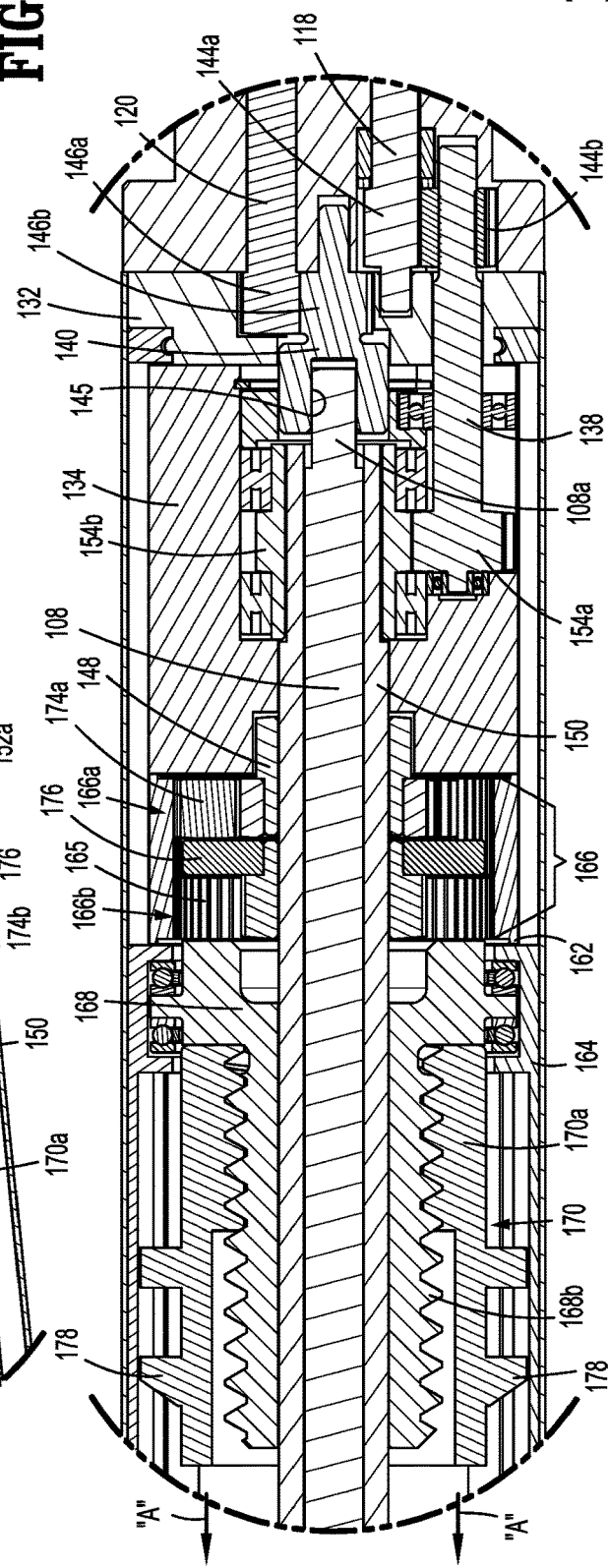

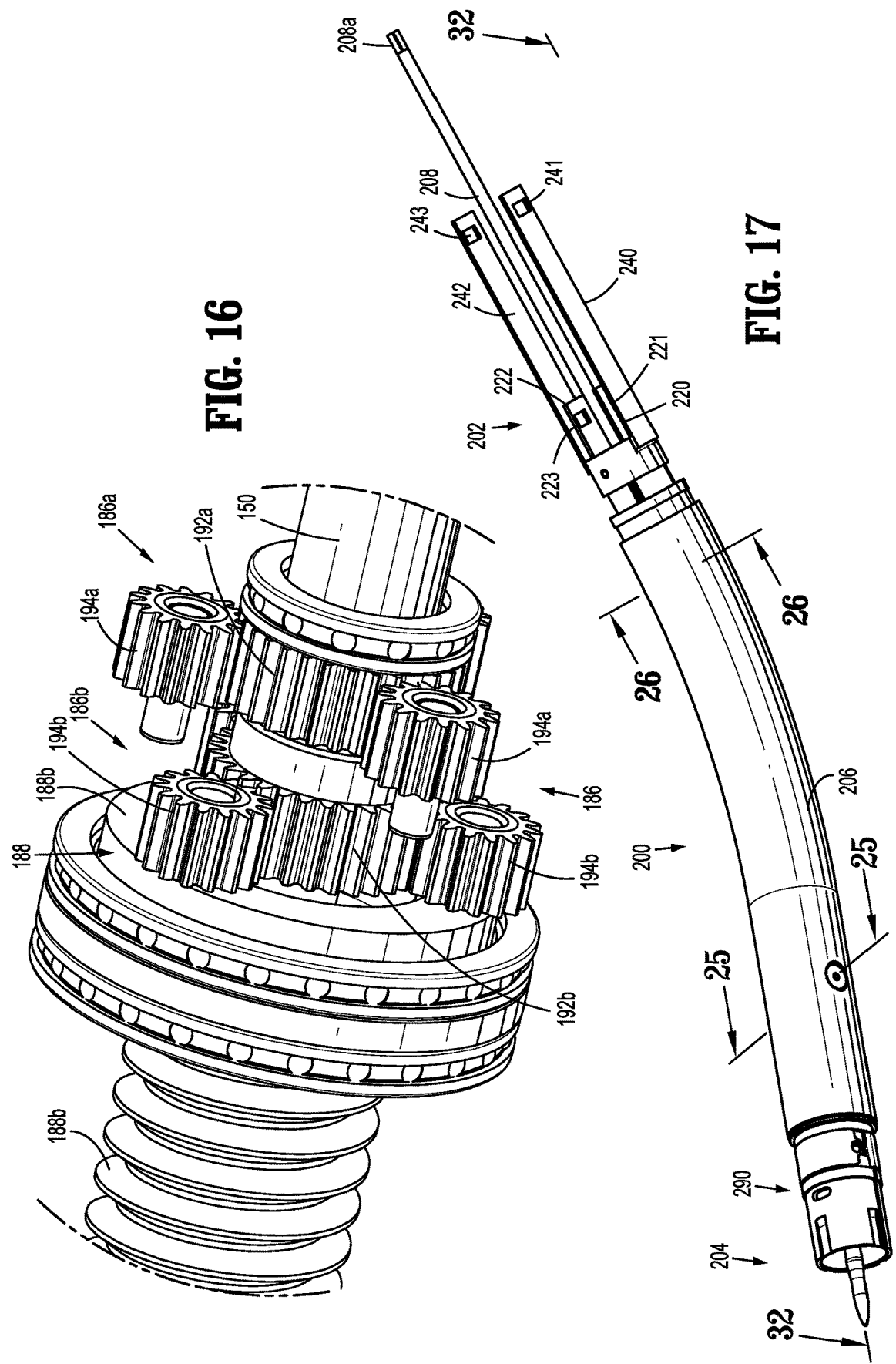

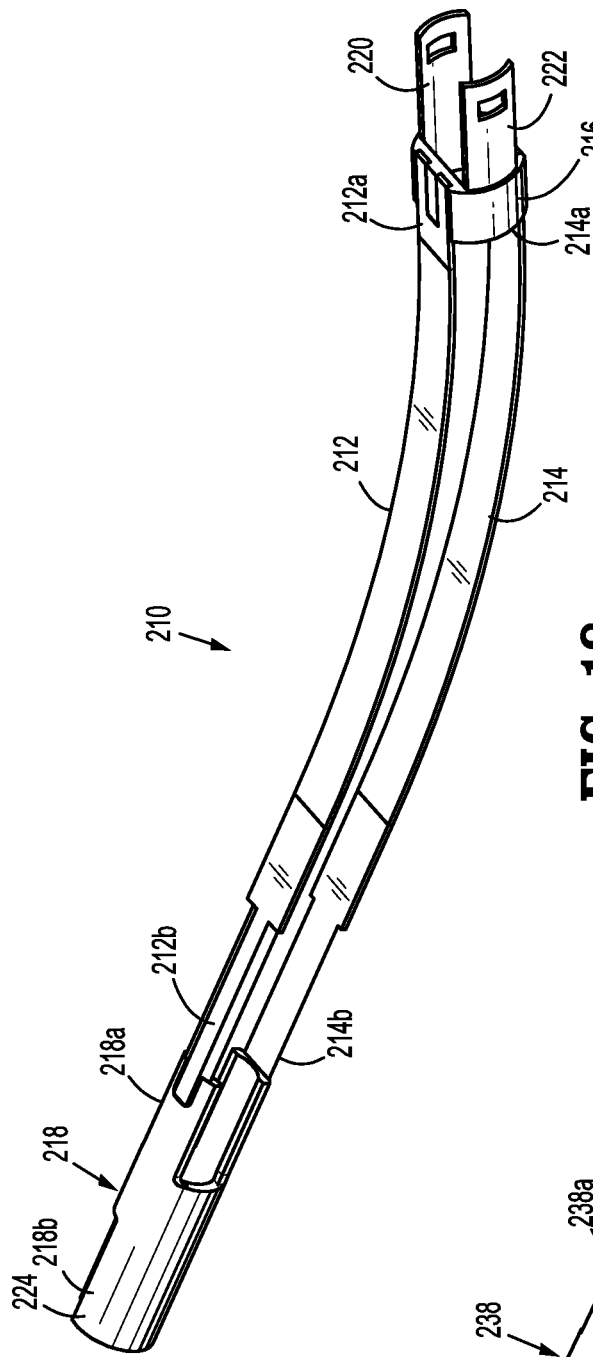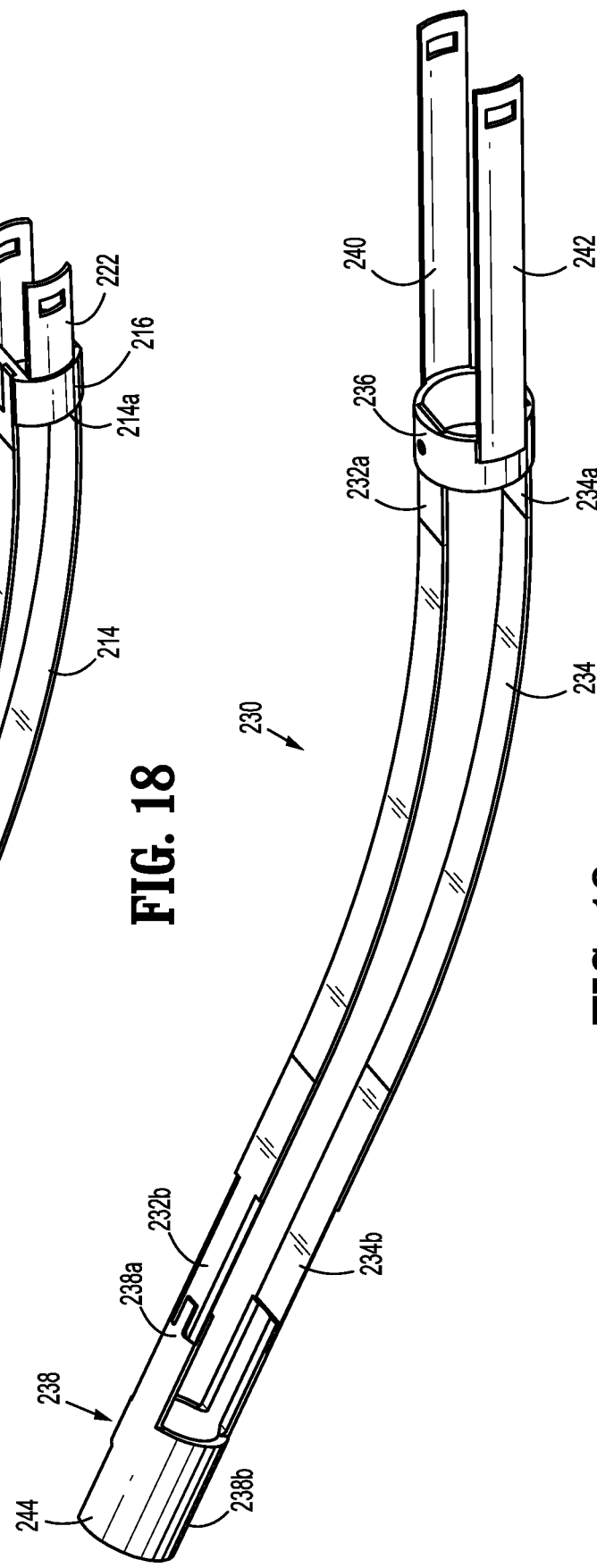

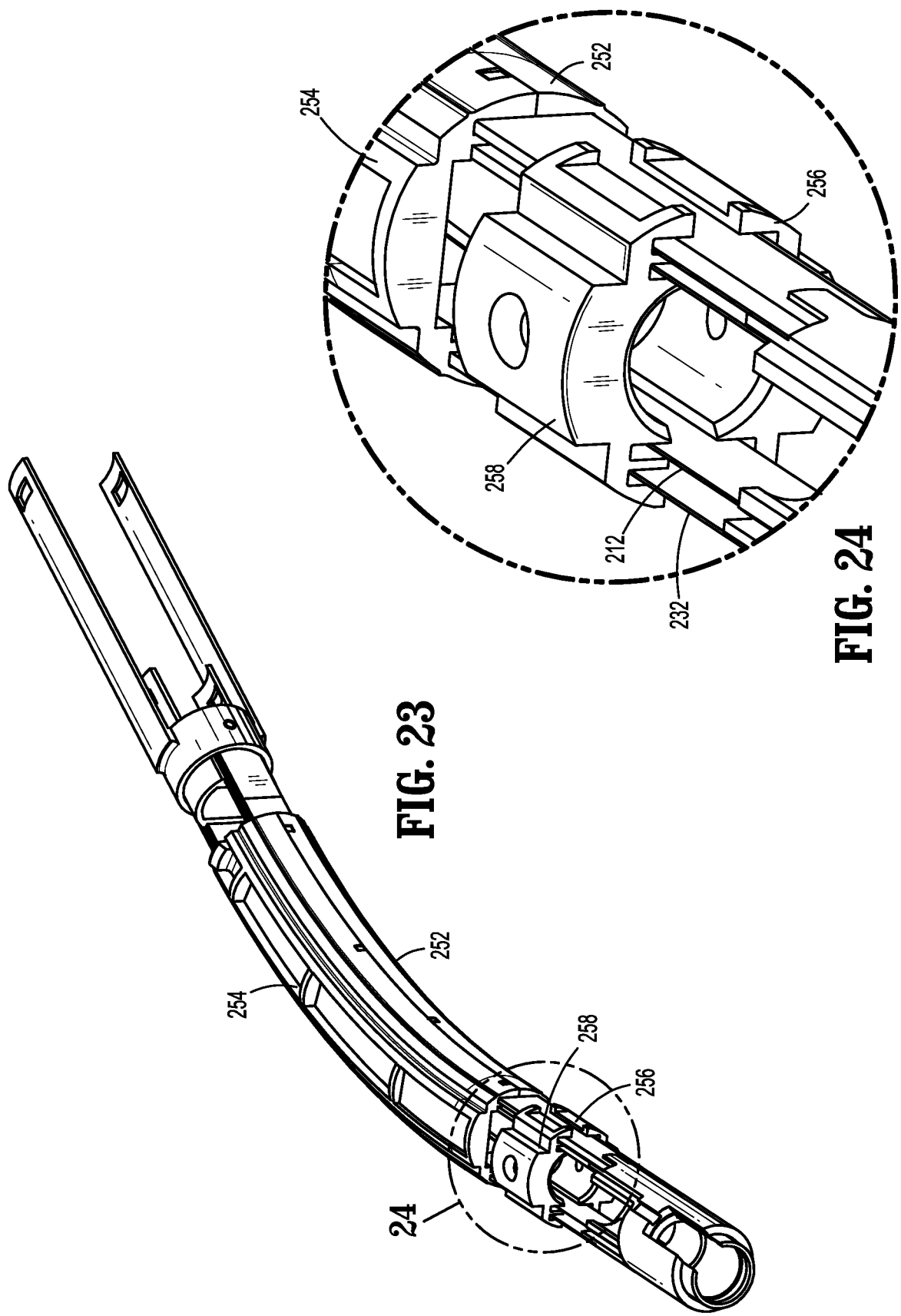

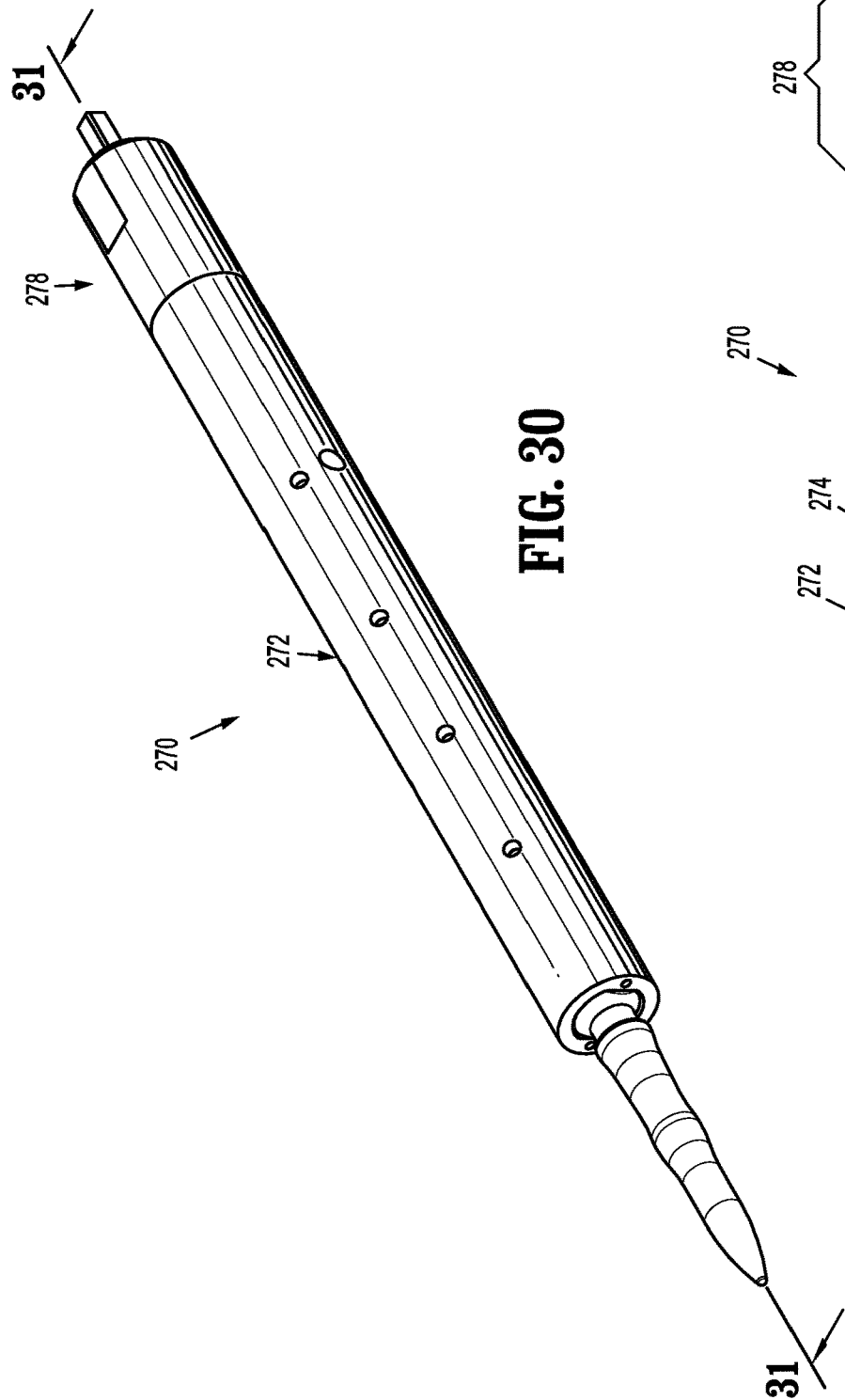
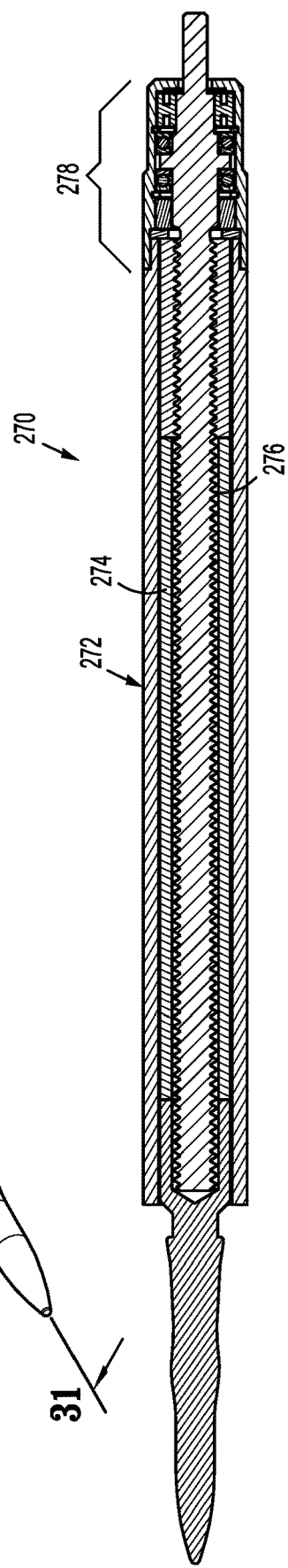

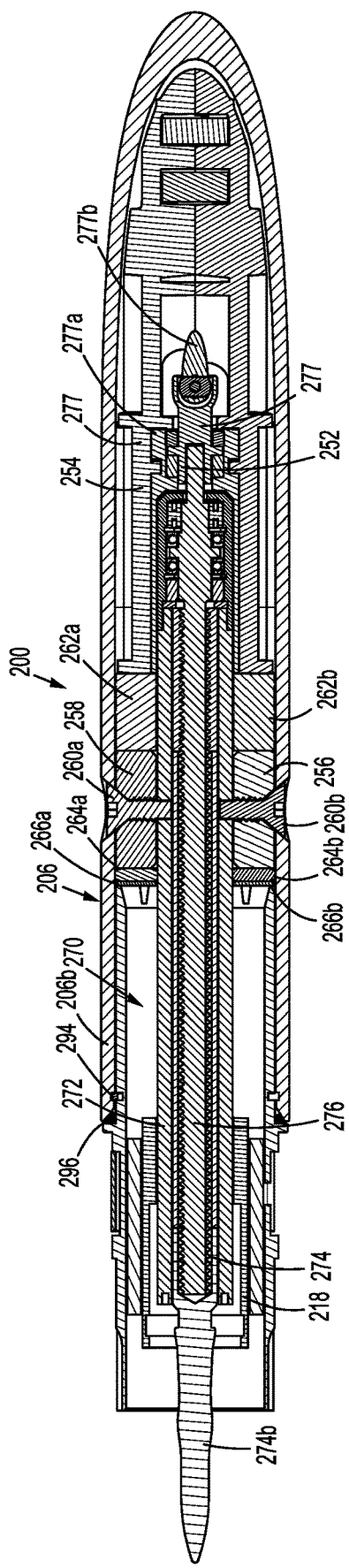
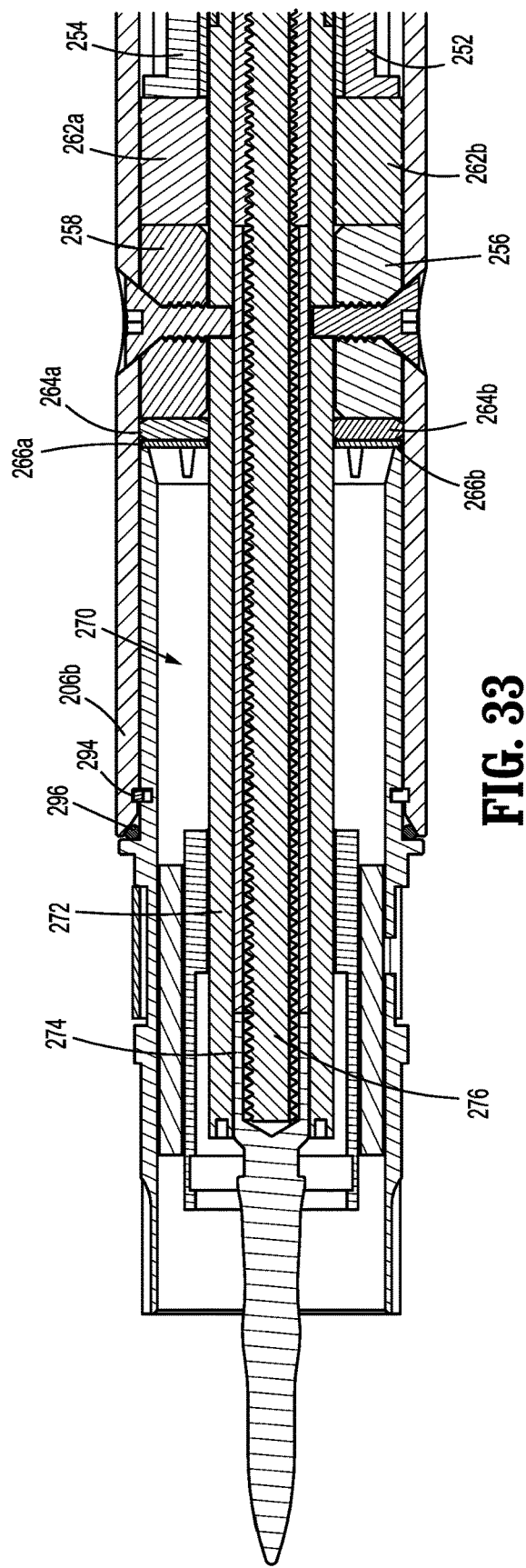
FIG. 32
FIG. 33

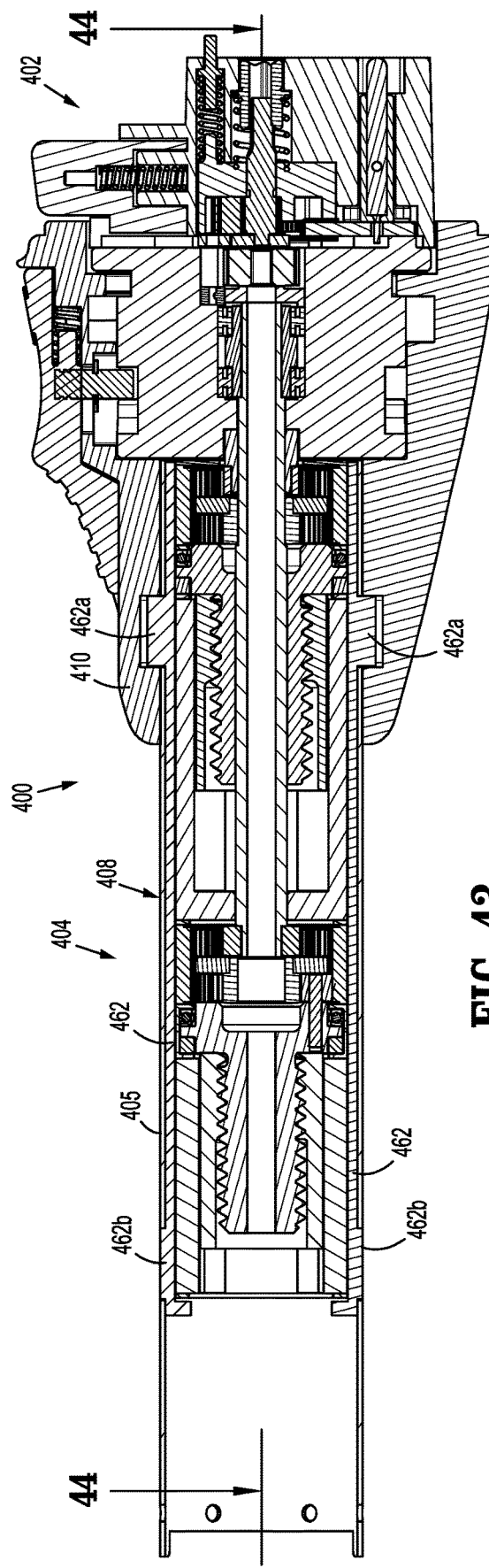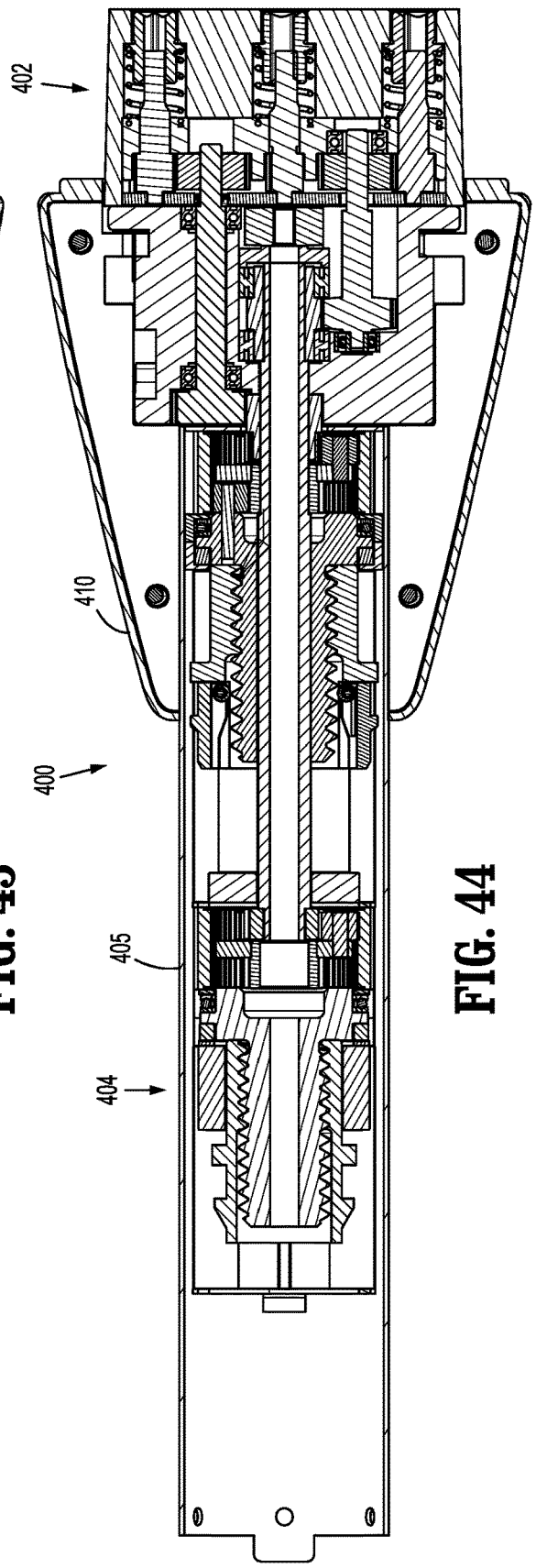
FIG. 43
FIG. 44

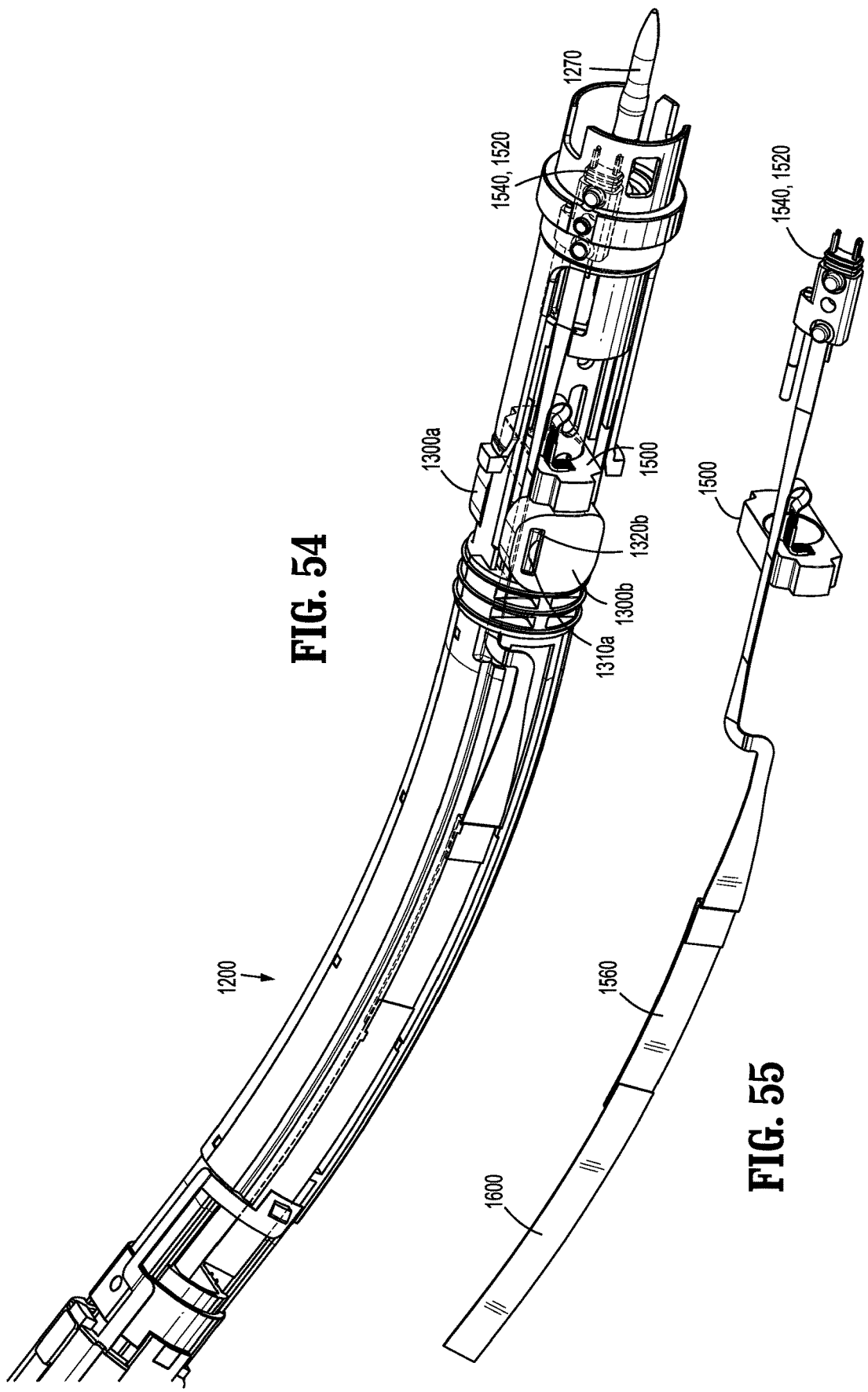

SURGICAL DEVICES WITH MOISTURE CONTROL

CROSS-REFERENCE TO RELATED APPLICATIONS

The present application is a Continuation Application claiming the benefit of and priority to U.S. patent application Ser. No. 16/826,928, filed on Mar. 23, 2020, (now U.S. Pat. No. 11,432,902), which claims the benefit of and priority to U.S. Provisional Patent Application Ser. No. 62/834,759, filed on Apr. 16, 2019, the entire content of each of which being incorporated herein by reference.

U.S. patent application Ser. No. 16/826,928, filed on Mar. 23, 2020, (now U.S. Pat. No. 11,432,902), is also a Continuation-in-Part Application claiming the benefit of and priority to International Patent Application No. PCT/US2019/045049, filed Aug. 5, 2019, which claims the benefit of and priority to each of U.S. Provisional Patent Application Ser. No. 62/718,065, filed on Aug. 13, 2018, U.S. Provisional Patent Application Ser. No. 62/718,079, filed on Aug. 13, 2018, U.S. Provisional Patent Application Ser. No. 62/718,089, filed on Aug. 13, 2018, U.S. Provisional Patent Application Ser. No. 62/718,102, filed on Aug. 13, 2018, and U.S. Provisional Patent Application Ser. No. 62/718,450, filed on Aug. 14, 2018, the entire content of each of which being incorporated herein by reference.

International Patent Application No. PCT/US2019/045049, filed Aug. 5, 2019, is a Continuation-in-Part Application claiming the benefit of and priority to U.S. patent application Ser. No. 14/991,157, filed on Jan. 8, 2016, (now U.S. Pat. No. 10,327,779), which claims the benefit of and priority to U.S. Provisional Application Ser. No. 62/145,759, filed on Apr. 10, 2015, the entire content of each of which being incorporated herein by reference.

BACKGROUND

Technical Field

The present disclosure relates generally to surgical devices. More specifically, the present disclosure relates to surgical devices with moisture control to facilitate thoroughly cleaning and drying the surgical devices.

Background of Related Art

Surgical instruments including powered devices for use in surgical procedures are known. To permit reuse of the handle assemblies of these surgical instruments and so that the handle assembly may be used with a variety of end effectors, adapter assemblies and extension assemblies have been developed for selective attachment to the handle assemblies and to a variety of end effectors. Additionally, following use, the adapter, end effector and/or extension assemblies may be thoroughly cleaned and/or sterilized for reuse.

SUMMARY

The present disclosure relates to a surgical device including an outer sleeve and a valve. The outer sleeve includes an inner wall, a port and a housing within the port. The port extends through the inner wall of the outer sleeve. The valve is disposed at least partially within the outer sleeve, and includes an engagement portion configured to selectively engage the port of the outer sleeve. The engagement portion of the valve is movable relative to the outer sleeve from an occluding position where the engagement portion forms a fluid-tight seal with the port, to an open position where at least a portion of the engagement portion is spaced from the port.

In disclosed embodiments, the valve is biased into the occluding position.

It is also disclosed that the valve includes a biasing element configured to urge the engagement portion of the valve radially outward and into the occluding position. In embodiments, the biasing element is a compression spring. It is further disclosed that the valve includes a body portion, and the biasing element is disposed about the body portion of the valve. It is additionally disclosed that the biasing element is disposed between the engagement portion of the valve and a wall of the housing of the outer sleeve.

Further, it is disclosed that the surgical device includes a second valve configured to selectively engage a second port of the outer sleeve.

The present disclosure also relates to a method of cleaning a surgical device. The method includes moving an engagement portion of a valve radially inward relative to a port of an outer sleeve of the surgical device from an occluding position where the engagement portion forms a fluid-tight seal with the port, to an open position where at least a portion of the engagement portion is spaced from the port, inserting fluid through the port in the outer tube of the surgical device, moving the fluid out of the surgical device, and maintaining the engagement portion of the valve in the open position after a majority of the fluid has moved out of the surgical device.

In disclosed embodiments, the method includes biasing the engagement portion of the valve into the occluding position.

Additionally, embodiments of the method include moving an engagement portion of a second valve radially inward relative to a second port of the outer sleeve of the surgical device from an occluding position where the engagement portion of the second valve forms a fluid-tight seal with the second port, to an open position where at least a portion of the engagement portion of the second valve is spaced from the second port. In embodiments, the method includes maintaining the engagement portion of the second valve in the open position while inserting fluid through the port in the outer tube of the surgical device.

The present disclosure relates to a surgical device including a handle housing, an elongated portion and a valve. The handle housing includes an outer wall and a port. The port extends through the outer wall. The elongated portion extends distally from the handle housing. The valve is disposed at least partially within the handle housing, and includes an engagement portion configured to selectively engage the port of the handle housing. The engagement portion of the valve is movable relative to the outer wall from an occluding position where the engagement portion forms a fluid-tight seal with the port, to an open position where at least a portion of the engagement portion is spaced from the port.

In disclosed embodiments, the valve is biased into the occluding position.

It is also disclosed that the valve includes a biasing element configured to urge the engagement portion of the valve radially outward and into the occluding position. In embodiments, the biasing element is a compression spring. It is further disclosed that the valve includes a body portion, and the biasing element is disposed about the body portion of the valve.

Further, it is disclosed that the surgical device includes a second valve configured to selectively engage a second port of the elongated portion.

The present disclosure also relates to a method of cleaning a surgical device. The method includes moving an engagement portion of a valve radially inward relative to a port of a handle housing of the surgical device from an occluding position where the engagement portion forms a fluid-tight seal with the port, to an open position where at least a portion of the engagement portion is spaced from the port, inserting fluid into the surgical device, moving the fluid out of the surgical device, and maintaining the engagement portion of the valve in the open position after a majority of the fluid has moved out of the surgical device.

In disclosed embodiments, the method includes biasing the engagement portion of the valve into the occluding position.

Additionally, embodiments of the method include moving an engagement portion of a second valve radially inward relative to a second port of the surgical device from an occluding position where the engagement portion of the second valve forms a fluid-tight seal with the second port, to an open position where at least a portion of the engagement portion of the second valve is spaced from the second port.

The present disclosure relates to a surgical kit including a surgical device and an actuator. The surgical device includes a handle assembly, an elongated portion extending distally from the handle assembly, a port, and a valve. The valve includes an engagement portion configured to selectively engage the port. The engagement portion of the valve is movable from an occluding position where the engagement portion forms a fluid-tight seal with the port, to an open position where at least a portion of the engagement portion is spaced from the port. The actuator includes a sleeve body and a finger. The sleeve body is configured to slidingly engage the elongated portion of the surgical device. The finger is configured to selectively engage the engagement portion of the valve to move the valve from the occluding position to the open position.

In disclosed embodiments, the finger of the actuator includes a plus sign-like or cruciform transverse cross-sectional profile, and the engagement portion of the valve of the surgical device includes a circular transverse cross-sectional profile.

It is also disclosed that the sleeve is ring-shaped, and that the finger extends radially inward from the sleeve body. In embodiments, the actuator includes a second finger extending radially inward from the sleeve body.

It is further disclosed that the surgical device includes a second port and a second valve. The second valve includes a second engagement portion configured to selectively engage the second port. The second engagement portion of the second valve is movable from an occluding position where the second engagement portion forms a fluid-tight seal with the second port, to an open position where at least a portion of the second engagement portion is spaced from the second port. The finger is configured to selectively engage the engagement portion of the valve to move the valve from the occluding position to the open position at the same time as the second finger engages the second engagement portion of the second valve to move the second valve from the occluding position to the open position.

The present disclosure also relates to a surgical kit including a surgical device and an actuator. The surgical device includes a handle housing, an elongated portion extending distally from the handle housing, a port, and a valve. The valve includes an engagement portion configured to selectively engage the port. The engagement portion of the valve is movable from an occluding position where the engagement portion forms a fluid-tight seal with the port, to an open position where at least a portion of the engagement portion is spaced from the port. The actuator includes a rack and a post extending from the rack. At least a portion of the surgical device is positionable on the actuator. The post is configured to selectively engage the engagement portion of the valve to move the valve from the occluding position to the open position.

In disclosed embodiments, the valve is disposed at least partially within handle housing of the surgical device.

It is also disclosed that the surgical device includes a second port and a second valve. The second valve includes a second engagement portion configured to selectively engage the second port. The second engagement portion of the second valve is movable from an occluding position where the second engagement portion forms a fluid-tight seal with the second port, to an open position where at least a portion of the second engagement portion is spaced from the second port.

In embodiments, the valve is disposed at least partially within the handle housing of the surgical device, and the second valve is disposed at least partially within the elongated portion of the surgical device.

It is further disclosed that the actuator includes a second post extending from the rack. The post is configured to selectively engage the engagement portion of the valve to move the valve from the occluding position to the open position at the same time as the second post engages the second engagement portion of the second valve to move the second valve from the occluding position to the open position.

The present disclosure relates to a surgical device including an outer sleeve, a port extending through the outer sleeve, and a valve disposed at least partially within the outer sleeve. The valve includes a vent that is slidably disposed with respect to the port between an open position and an occluding position, and a thermostat configured to urge the vent to its open position in response to the thermostat being exposed to a predetermined temperature.

In disclosed embodiments, the valve includes a biasing element configured to urge the vent towards its occluding position. It is also disclosed that a portion of the thermostat contacts a portion of the vent.

In embodiments, the vent is configured to move to its occluding position in response to the thermostat being exposed to a temperature that is below the predetermined temperature. It is further disclosed that the predetermined temperature is about 130° C.

The present disclosure also relates to a surgical device including an outer sleeve, a port extending through the outer sleeve, and a valve. The valve is disposed at least partially within the outer sleeve, and is made from a bimetal material. A portion of the valve is configured to move relative to the port between an open position and an occluding position in response to the valve being exposed to a predetermined temperature.

It is also disclosed that the valve includes a first leg, a second leg, a third leg, and an occluding portion. The second leg extends adjacent a first end of the first leg, and the third leg extends adjacent a second end of the second leg. It is further disclosed that the first leg moves toward the second leg in response to the valve being exposed to the predetermined temperature.

In embodiments, the portion of the valve is configured to remain in its occluding position in response to the valve being exposed to a temperature that is below the predetermined temperature. It is disclosed that the predetermined temperature is about 130° C.

In disclosed embodiments, the surgical device includes a shaft, and that rotation of the shaft relative to the outer sleeve causes the valve to move to its occluding position.

The present disclosure relates to a surgical device including a handle assembly, and elongated portion, an end effector, a drive shaft, and a wick. The elongated portion is configured to extend distally from the handle assembly and includes an outer sleeve. The end effector is configured to operatively engage a distal portion of the elongated portion. The drive shaft extends at least partially through the elongated portion and is configured to mechanically engage the handle assembly and the end effector. The wick is disposed within the outer sleeve and is made from a fibrous material. The wick is configured to transfer moisture from a first portion of the wick to a second portion of the wick.

In disclosed embodiments, the wick is in the shape of a cylindrical sleeve.

It is disclosed that an entirety of the wick is disposed within the outer sleeve.

It is further disclosed that a first portion of the wick is cylindrical, and a second portion of the wick surrounds a longitudinal passage which surrounds the drive shaft.

In embodiments, the wick is configured to transfer moisture from a proximal portion of the wick to a distal portion of the wick. The distal portion of the wick is in fluid communication with ambient air outside of the elongated portion.

In disclosed embodiments, the wick is a fibrous sheet of material.

The present disclosure also relates to a method of cleaning a surgical device. The method includes inserting fluid into the surgical device, absorbing the fluid with a first portion of a fibrous wick disposed within the surgical device, transferring the fluid from the first portion of the fibrous wick to a second portion of the fibrous wick, and desorbing the fluid from the fibrous wick into ambient air.

In disclosed embodiments, transferring the fluid from the first portion of the fibrous wick to the second portion of the fibrous wick includes moving the fluid distally.

In an embodiment, the wick may be impregnated with a desiccating compound.

The desiccating compound may include at least one of activated alumina, aerogel, benzophenone, bentonite clay, calcium chloride, calcium oxide, calcium sulfate, cobalt(II) chloride, copper(II) sulfate, lithium chloride, lithium bromide, magnesium sulfate, magnesium perchlorate, molecular sieve, potassium carbonate, potassium hydroxide, silica gel, sodium, sodium chlorate, sodium chloride, sodium hydroxide, sodium sulfate, sucrose or sulfuric acid.

BRIEF DESCRIPTION OF THE DRAWINGS

Embodiments of the present disclosure are described herein with reference to the accompanying drawings, wherein:

FIG. 3 is perspective side view of the adapter assembly of FIG. 1;

FIG. 4 is a perspective side view of the adapter assembly of FIG. 3 with the outer sleeve removed;

FIG. 5 is a perspective side view of the adapter assembly of FIGS. 3 and 4 with proximal and distal housings of first and second pusher assemblies removed;

FIG. 8 is an enlarged, perspective view of a coupling assembly and a transfer assembly of the adapter assembly of FIGS. 2-7;

FIG. 9 is a perspective side view of the adapter assembly of FIGS. 2-7 with the housing assemblies removed;

FIG. 11 is an enlarged view of the indicated area of detail of FIG. 6;

FIG. 12 is an enlarged view of the indicated area of detail of FIG. 7;

FIG. 16 is an enlarged view of the indicated area of detail of FIG. 9;

FIG. 17 is a perspective side view of the extension assembly of FIG. 1;

FIG. 18 is a perspective side view of an inner flexible band assembly of the extension assembly of FIG. 17;

FIG. 19 is a perspective side view of an outer flexible band assembly of the extension assembly of FIG. 17;

FIG. 23 is a front, perspective view of the inner and outer flexible band assemblies and the frame assembly of FIG. 20;

FIG. 24 is an enlarged view of the indicated area of detail of FIG. 23;

FIG. 30 is a perspective side view of the trocar assembly of FIG. 29;

FIG. 31 is a cross-sectional side view taken along line 31-31 of FIG. 30;

FIG. 32 is a cross-sectional top view taken along line 32-32 of FIG. 17;

FIG. 33 is an enlarge cross-sectional view of the distal end of the extension assembly of FIG. 17;

FIG. 43 is a cross-sectional side view taken along line 43-43 of FIG. 42;

FIG. 44 is a cross-sectional side view taken along line 44-44 of FIG. 42;

FIGS. 53 and 54 are perspective views of a distal portion of the adapter assembly of FIG. 50, with some parts removed;

FIG. 55 is a perspective view of a sensor assembly of the adapter assembly of FIG. 50;

DETAILED DESCRIPTION

Figure 1:
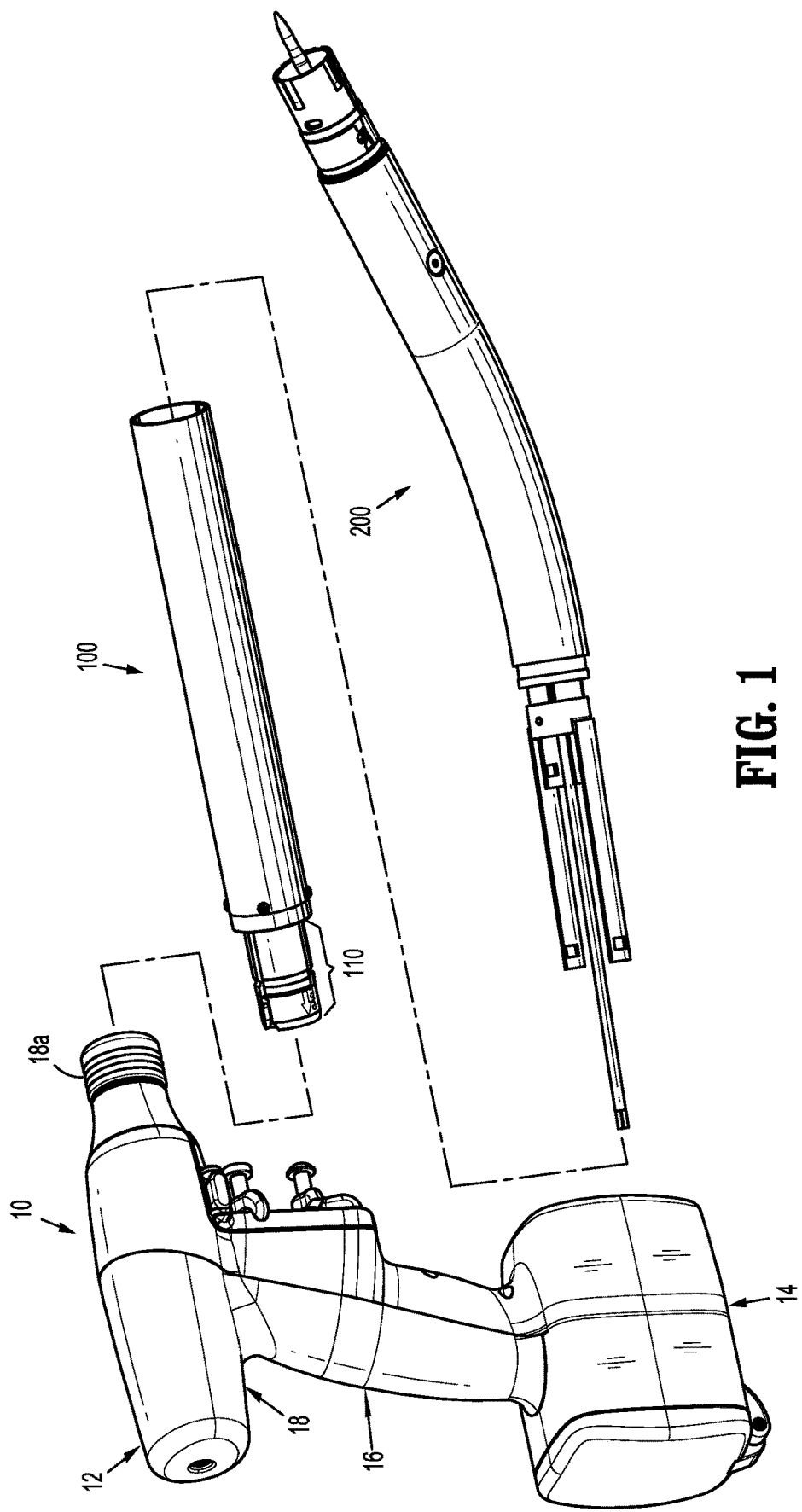
FIG. 1 is a perspective separated view of an adapter assembly, in accordance with an embodiment of the present disclosure, an extension assembly, in accordance with an embodiment of the present disclosure, and an exemplary handheld electromechanical surgical device.

Embodiments of the presently disclosed seal assemblies for surgical instruments are described in detail with reference to the drawings, in which like reference numerals designate identical or corresponding elements in each of the several views. As used herein the term "distal" refers to that portion of the seal assembly or surgical instrument, or component thereof, farther from the user, while the term "proximal" refers to that portion of the seal assembly or surgical instrument, or component thereof, closer to the user.

With reference to FIG. 1, an adapter assembly in accordance with an embodiment of the present disclosure, shown generally as adapter assembly 100, and an extension assembly according to an embodiment of the present disclosure, shown generally as extension assembly 200, are configured for selective connection to a powered handheld electromechanical instrument shown, generally as surgical device 10. As illustrated in FIG. 1, surgical device 10 is configured for selective connection with adapter assembly 100, and, in turn, adapter assembly 100 is configured for selective connection with an extension assembly 200. Extension assembly 200 is configured for selective connection with a tool assembly or end effector, e.g. tool assembly 30 (FIG. 34), including a loading unit, e.g. loading unit 40 (FIG. 34), and an anvil assembly, e.g., anvil assembly 50 (FIG. 34), for applying a circular array of staples (not shown) to tissue (not shown).

Figure 2:
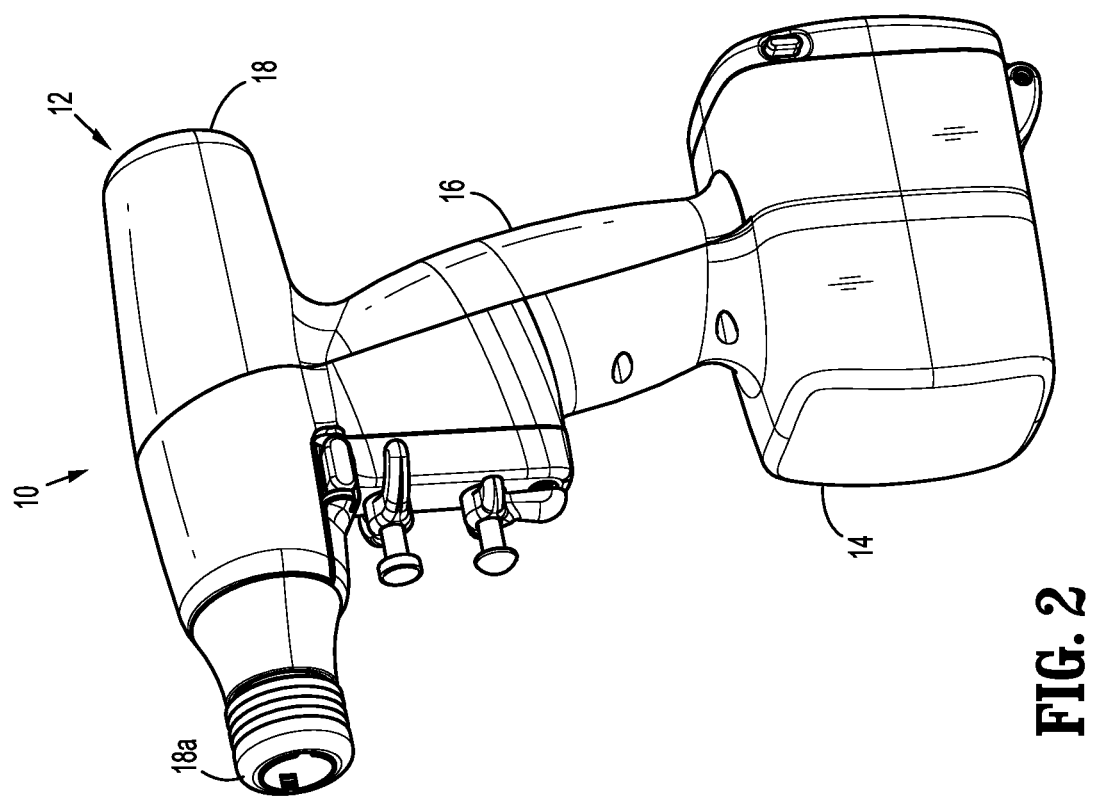
FIG. 2 is a perspective side view of the exemplary handheld electromechanical surgical device of FIG. 1.
Figure 6:
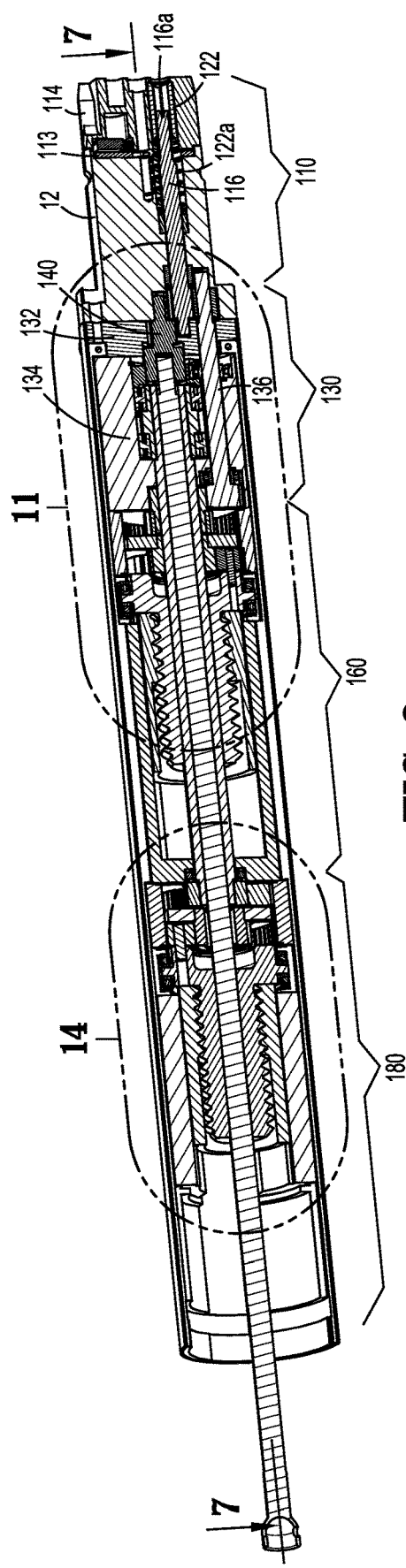
FIG. 6 is a cross-sectional side view of the adapter assembly of FIGS. 2-4 taken along line 6-6 in FIG. 3.
Figure 7:
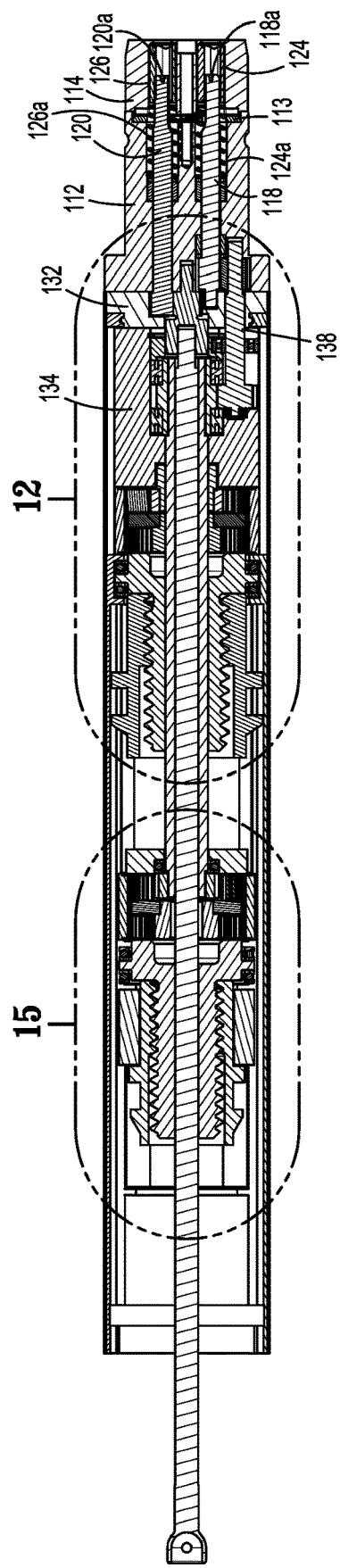
FIG. 7 is a cross-sectional side view of the adapter assembly of FIGS. 2-5 taken along line 7-7 in FIG. 5.

As illustrated in FIGS. 1 and 2, surgical device 10 includes a handle housing 12 having a lower housing portion 14, an intermediate housing portion 16 extending from and/or supported on lower housing portion 14, and an upper housing portion 18 extending from and/or supported on intermediate housing portion 16. A distal half-section of upper housing portion 18 defines a nose or connecting portion 18a configured to accept a corresponding drive coupling assembly 110 (FIG. 10) of adapter assembly 100. For a detailed description of the structure and function of an exemplary electromechanical instrument, please refer to commonly-owned U.S. Pat. No. 9,055,943, the contents of which is incorporated by reference herein in its entirety.

Adapter assembly 100 will now be described with reference to FIGS. 3-20. Referring initially to FIG. 3, adapter assembly 100 includes a proximal end 102 configured for operable connection to connecting portion 18a (FIG. 1) of surgical device 10 (FIG. 1) and a distal end 104 configured for operable connection to extension assembly 200 (FIG. 1). In accordance with the present disclosure, adapter assembly 100 may be substantially or fully rigid along the entire length.

Turning to FIGS. 3-5, from proximal end 102 to distal end 104 of adapter assembly 100, adapter assembly 100 includes a drive coupling assembly 110, a drive transfer assembly 130 operably connected to drive coupling assembly 110, a first pusher assembly 160 operably connected to drive transfer assembly 130, and a second pusher assembly 180 operably connected to drive transfer assembly 130. Each of drive transfer assembly 130, first pusher assembly 160 and second pusher assembly 180 are operably maintained within an outer sleeve 106 (FIG. 3). As will be described in further detail below, a shaft 108 (FIG. 3) extends longitudinally through adapter assembly 100 and is operably connected to drive transfer assembly 130.

With reference to FIGS. 5-9, drive coupling assembly 110 has a cylindrical profile and is configured to selectively secure adapter assembly 100 to surgical device 10 (FIG. 1). Drive coupling assembly 110 includes a connector housing 112 and a connector extension 114 fixedly connected to connector housing 112 by a mounting plate 113. Connector housing 112 and connector extension 114 operate to rotatably support a first rotatable proximal drive shaft 116, a second rotatable proximal drive shaft 118, and a third rotatable proximal drive shaft 120. Connector housing 112 and connector extension 114 of drive coupling assembly 110 also rotatably supports first, second, and third connector sleeves 116, 118, and 120, respectively. Each of connector sleeves 122, 124, 126 is configured to mate with respective first, second, and third drive connectors (not shown) of surgical device 10 (FIG. 1). Each connector sleeve 122, 124, 126 is further configured to mate with a proximal end 116a, 118a, 120a of respective first, second and third proximal drive shafts 116, 118, 120.

Drive coupling assembly 110 also includes first, second and third biasing members 122a, 124a and 126a disposed distally of respective first, second and third connector sleeves 122, 124, 126. Each of biasing members 122a, 124a and 126a is disposed about respective first, second, and third rotatable proximal drive shafts 122, 124 and 126 to help maintain connector sleeves 122, 124, and 126 engaged with the distal end of respective drive rotatable drive connectors (not shown) of surgical device 10 when adapter assembly 100 is connect to surgical device 10. In particular, first, second and third biasing members 122a, 124a and 126a function to bias respective connector sleeves 122, 124 and 126 in a proximal direction.

For a detailed description of an exemplary drive coupling assembly, please refer to U.S. Pat. No. 9,055,943, the contents of which was previously incorporated by reference herein.

With reference to FIGS. 9-13, drive transfer assembly 130 (FIGS. 10 and 13) of adapter assembly 100 has a cylindrical profile and operably connects distal ends of first, second and third rotatable proximal drive shafts 116, 118 and 120 to shaft 108, first pusher assembly 160, and second pusher assembly 180, respectively. Drive transfer assembly 130 includes a support plate 132 (FIGS. 11 and 12) secured to a proximal end of connector housing 112 and a drive transfer housing 134 positioned adjacent support plate 132. Support plate 132 and housing 134 operate to rotatably support a first rotatable distal drive shaft 136, a second rotatable distal drive shaft 138 and a drive member 140.

First and second rotatable distal drive shafts 136 and 138 are each operably connected to respective first and second rotatable proximal drive shafts 116 and 118 of drive coupling assembly 110 by a pair of gears. In particular, distal ends of each of first and second rotatable proximal drive shaft 116 and 118 include a geared portion 142a and 144a, respectively, which engages a proximal drive gear 142b and 144b on a proximal end of respective first and second distal drive shafts 136 and 138. As shown, each of respective paired geared portion and proximal drive gear 142a, 142b and 144a, 144b are the same size to provide a 1:1 gear ratio between the respective rotatable proximal and distal drive shafts. In this manner, respective rotatable proximal and distal drive shafts rotate at the same speed. However, it is envisioned that either or both of the paired geared portions and proximal drive gears may be of different sizes to alter the gear ratio between the rotatable proximal and distal drive shafts.

A distal end of third proximal drive shaft 120 of drive coupling assembly 110 includes a geared portion 146a that engages a geared portion 146b formed on a proximal end of drive member 140 of drive transfer assembly 130. The size of geared portion 146a on third proximal drive shaft 120 and geared portion 146b on drive member 140 are the same size to provide a 1:1 gear ratio between third proximal drive shaft 120 and drive member 140. In this manner, third proximal drive shaft 120 and drive member 140 rotate at the same speed. However, it is envisioned that either or both of geared portions 146a, 146b may be of different sizes to alter the gear ratio between third proximal drive shaft 120 and drive member 140. A distal end of drive member 140 defines a socket 145 that receives a proximal end 108a of shaft 108. Alternatively, socket 145 may be configured to operably engage a proximal end 208a of a drive shaft (FIG. 17) of an extension assembly 200 (FIG. 17).

Drive transfer assembly 130 also includes a drive connector 148 (FIG. 11) operably connecting first rotatable distal drive shaft 136 to first pusher assembly 160 and a tubular connector 150 operably connecting second rotatable distal drive shaft 138 to second pusher assembly 180. In particular, a distal end of first rotatable distal drive shaft 136 includes a geared portion 152a that engages a geared portion 152b of drive connector 148. A distal end of second rotatable distal drive shaft 138 includes a geared portion 154a that engages a drive gear 154b secured to a distal end of tubular connector 150.

Figure 10:
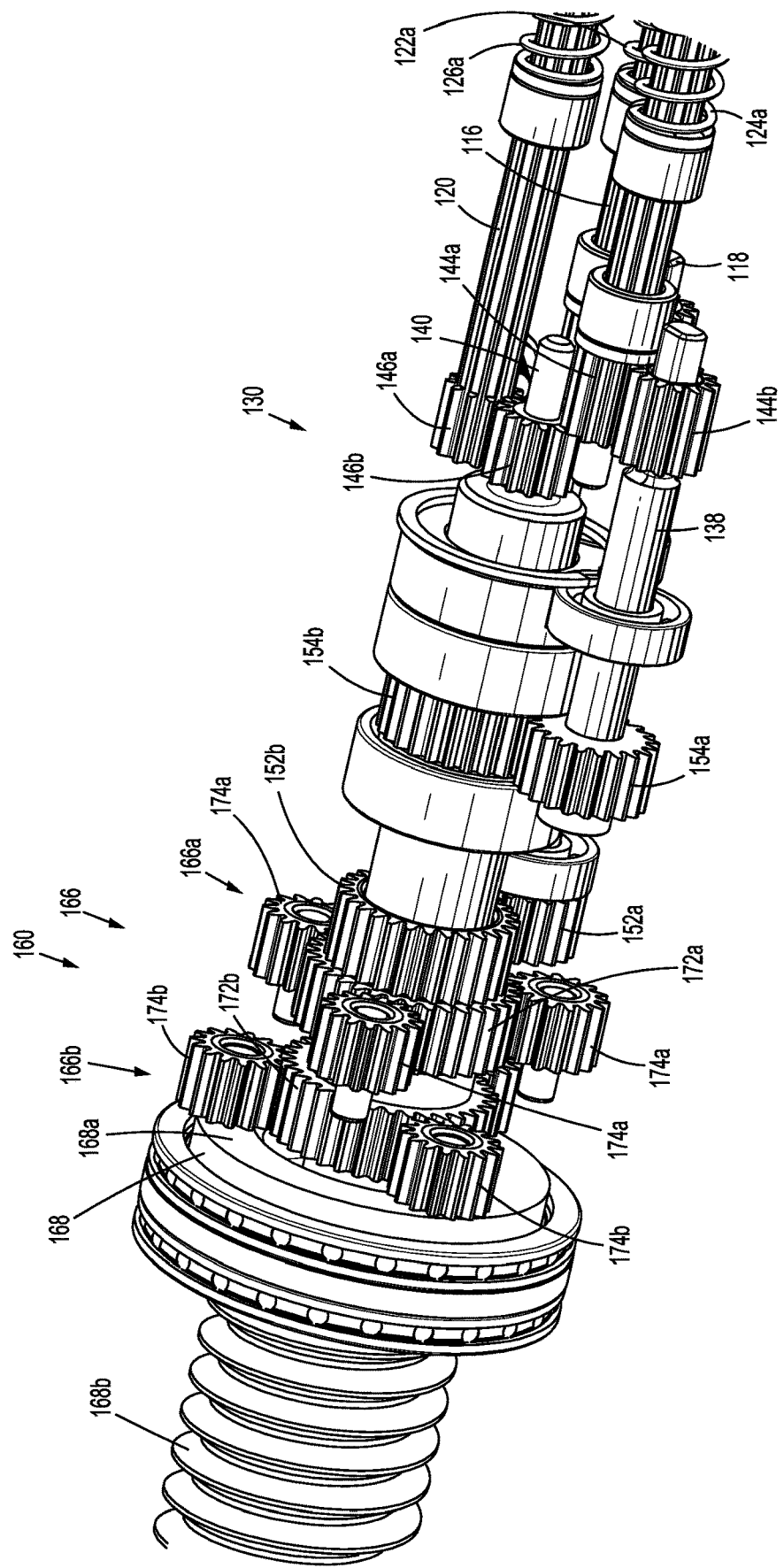
FIG. 10 is an enlarged view of the indicated area of detail of FIG. 9.
Figure 13:
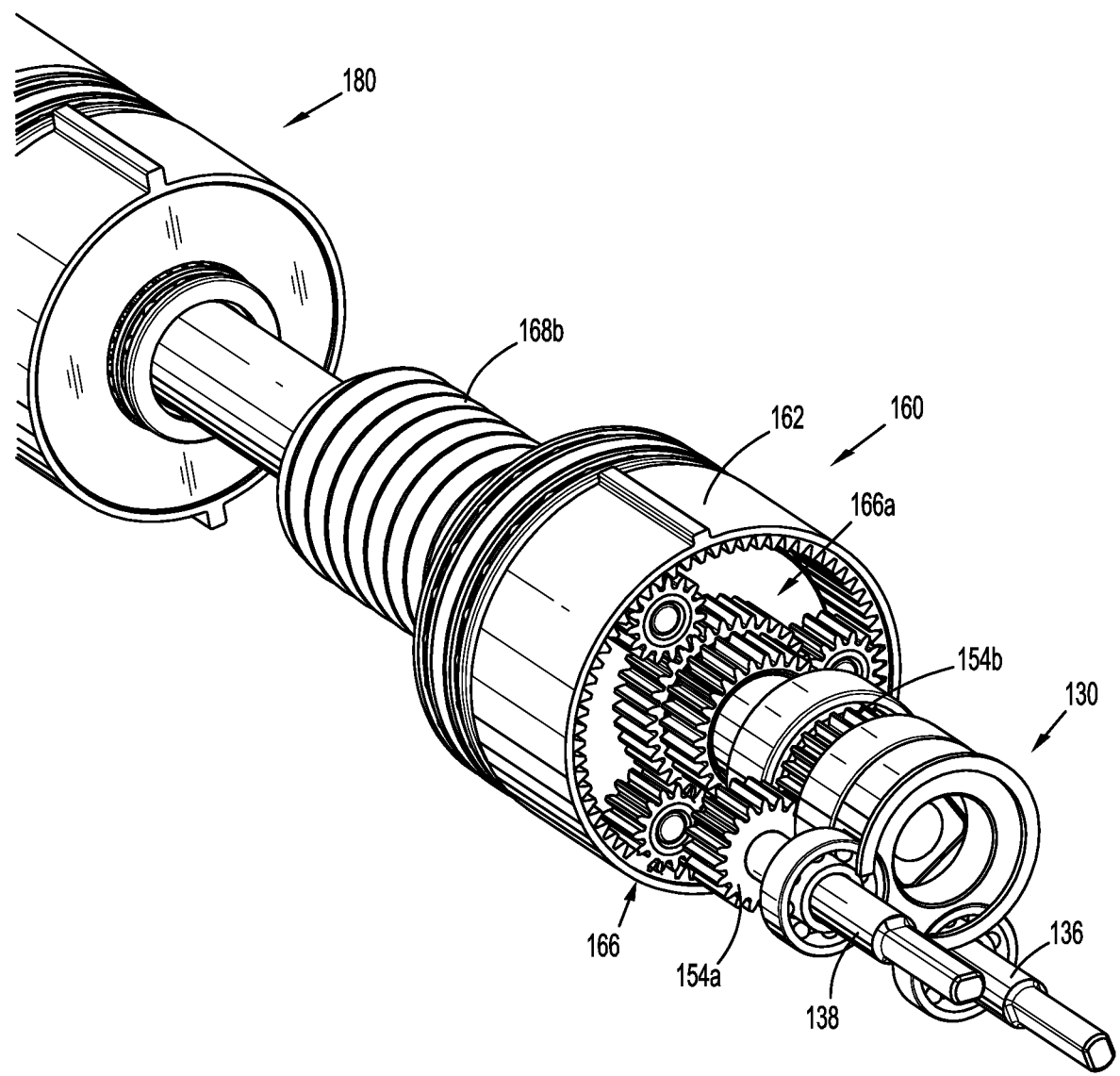
FIG. 13 is a perspective end view of the transfer assembly of FIG. 8.

As shown in FIG. 10, geared portion 152a of first rotatable distal drive shaft 136 is smaller than geared portion 152b of drive connector 148 to provide a gear ratio of greater than 1:1 between first rotatable distal drive shaft 136 and drive connector 148. In this manner, drive connector 148 rotates at a slower speed than first rotatable distal drive shaft 136. Similarly, geared portion 154a of second rotatable distal drive shaft 138 is smaller than drive gear 154b on tubular connector 150 to provide a gear ratio of greater than 1:1 between second rotatable distal drive shaft 138 and drive connector 148. In this manner, tubular connector 150 rotates at a slower speed than second rotatable distal drive shaft 138. However, it is envisioned that each of paired geared portion 152a and geared portion 152b, and geared portion 154a and drive gear 154b may be the same size to provide a gear ratio of 1:1 between respective first rotatable distal drive shaft 136 and drive connector 148 and between second rotatable distal drive shaft 138 and tubular connector 150.

With particular reference to FIGS. 9-13, first pusher assembly 160 includes proximal and distal housing sections 162, 164 (FIG. 11), a planetary gear assembly 166 operably mounted within proximal housing section 162, a screw member 168 (FIG. 11) operably connected to planetary gear assembly 166 and rotatably supported within distal housing section 164, and a pusher member 170 (FIG. 11) operably connected to screw member 168 and slidably disposed within distal housing section 164. Planetary gear assembly 166 includes first and second planetary gear systems 166a, 166b (FIG. 10). First planetary gear system 166a includes a central drive gear 172a mounted on a distal end of drive connector 148 of drive transfer assembly 130 and a plurality of planetary gears 174a rotatably mounted to a rotatable support ring 176.

Each planetary gear 174a of first planetary gear system 166a engages central drive gear 172a and a toothed inner surface 165 of proximal housing section 162. As central drive gear 172a rotates in a first direction, e.g., clockwise, each planetary gear 174a rotates in a second direction, e.g., counter-clockwise. As each planetary gear 174a rotates in the second direction, engagement of planetary gears 174a with toothed inner surface 165 of distal housing section 162 causes rotatable support ring 176 to rotate in the first direction. Conversely, rotation of central drive gear 172a in the second direction causes rotation of each planetary gear 174a in the first direction thereby causing rotation of rotatable support ring 176 in the second direction. The configuration of first planetary gear system 166a provides a reduction in the gear ratio. In this manner, the speed of rotation of rotatable support ring 174 is less than the speed of rotation of central drive gear 170a.

Second planetary gear system 166b includes a central drive gear 172b securely affixed to rotatable support ring 176 and a plurality of planetary gears 174b rotatably mounted to a proximal end surface 168a of screw member 168. Each planetary gear 174b of second planetary gear system 166b engages central drive gear 172b and toothed inner surface 165 of proximal housing section 162. As rotatable support ring 176 of first planetary gear system 166a rotates in the first direction thereby causing central drive gear 172b to also rotate in the first direction, each planetary gear 174b rotates in the second direction. As each planetary gear 174b rotates in the second direction, engagement of planetary gears 174b with toothed inner surface 165 of proximal housing section 162 causes screw member 168 to rotate in the first direction. Conversely, rotation of central drive gear 172b in the second direction causes rotation of each planetary gear 174b in the first direction, thereby causing screw member 168 to rotate in the second direction. The configuration of second planetary gear system 166b provides a reduction in the gear ratio. In this manner, the speed of rotation of screw member 168 is less than the speed of rotation of central drive gear 172b. First and second planetary gear systems 166a, 166b operate in unison to provide a reduction in the gear ratio between first rotatable proximal drive shaft 116 and screw member 168. In this manner, the reduction in the speed of rotation of screw member 168 relative to drive connector 148 is a product of the reduction provided by the first and second planetary gear systems 166a, 166b.

Screw member 168 is rotatably supported within proximal housing portion 162 and includes a threaded distal end 168b that operably engages a threaded inner surface 170a of pusher member 170. As screw member 168 is rotated in the first direction, engagement of threaded distal end 168b of screw member 168 with threaded inner surface 170a of pusher member 170 (which is keyed to permit axial translation and prevent rotation thereof) causes longitudinal advancement of pusher member 170, as indicated by arrows "A" in FIG. 12. Conversely, rotation of screw member 168 in the second direction causes retraction of pusher member 170.

Pusher member 170 of first pusher assembly 160 of adapter assembly 100 includes a pair of tabs 178 formed on a distal end thereof for engaging connector extensions 240, 242 (FIG. 19) of outer flexible band assembly 230 (FIG. 19) of extension assembly 200 (FIG. 17). Although shown as tabs 178, it is envisioned that pusher member 170 may include any structure suitable for selectively engaging connector extensions 240, 242 of outer flexible band 230 of extension assembly 200.

Figure 14:
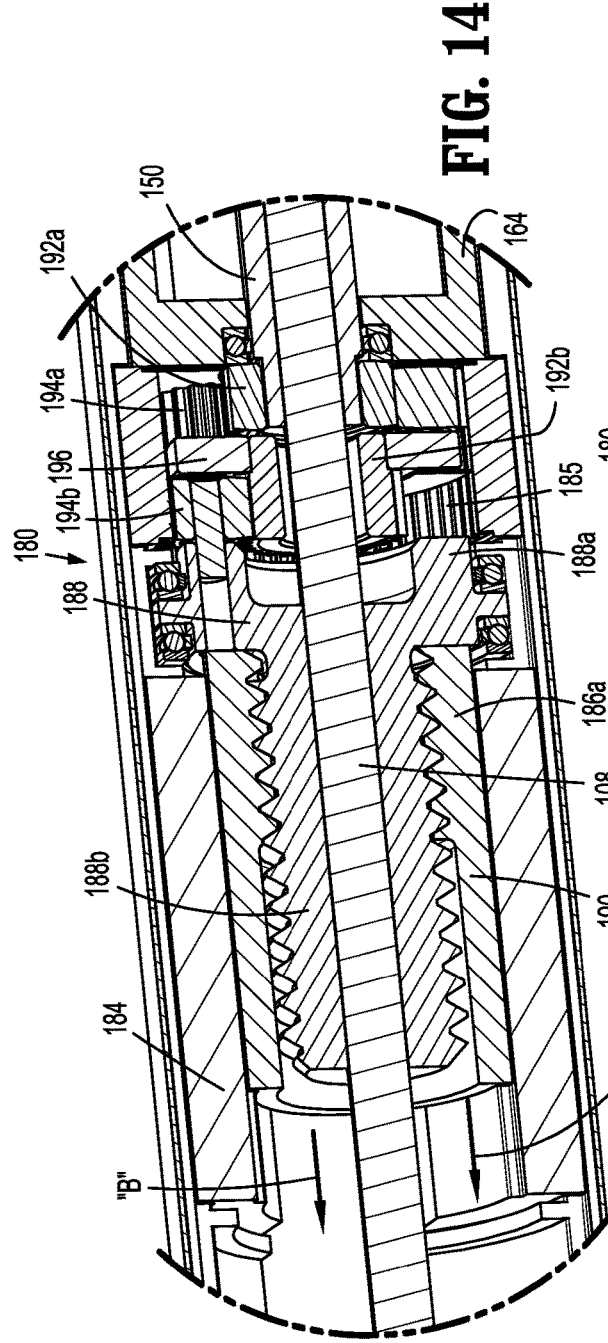
FIG. 14 is an enlarged view of the indicated area of detail of FIG. 6.
Figure 15:
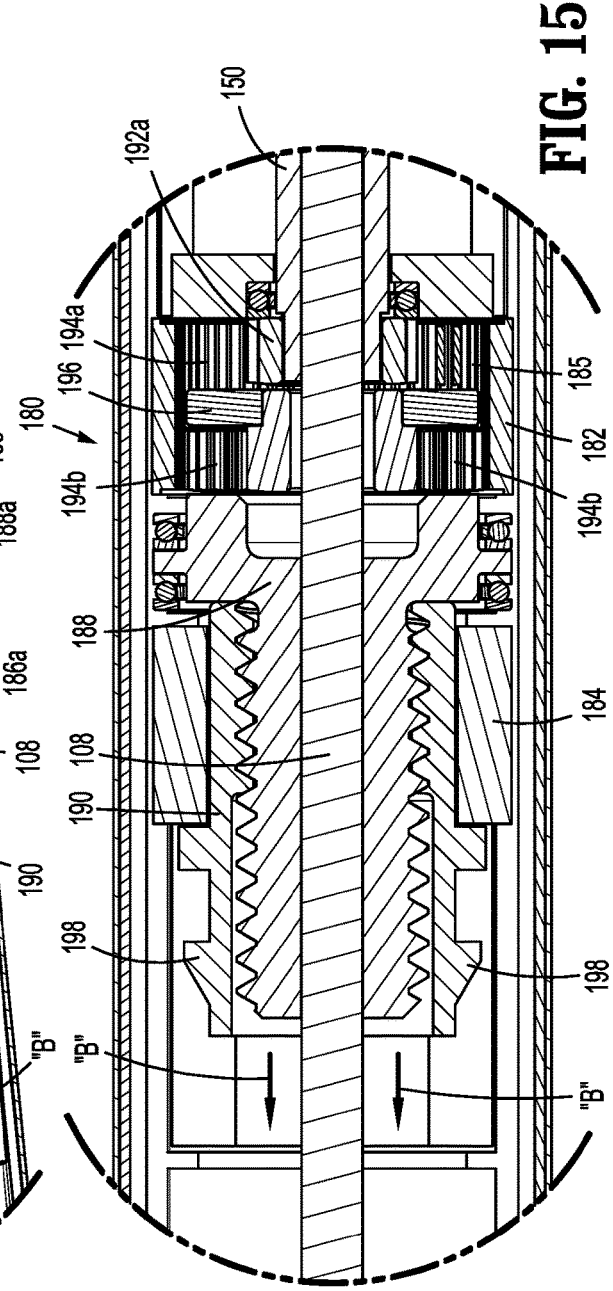
FIG. 15 is an enlarged view of the indicated area of detail of FIG. 7.
Figure 20:
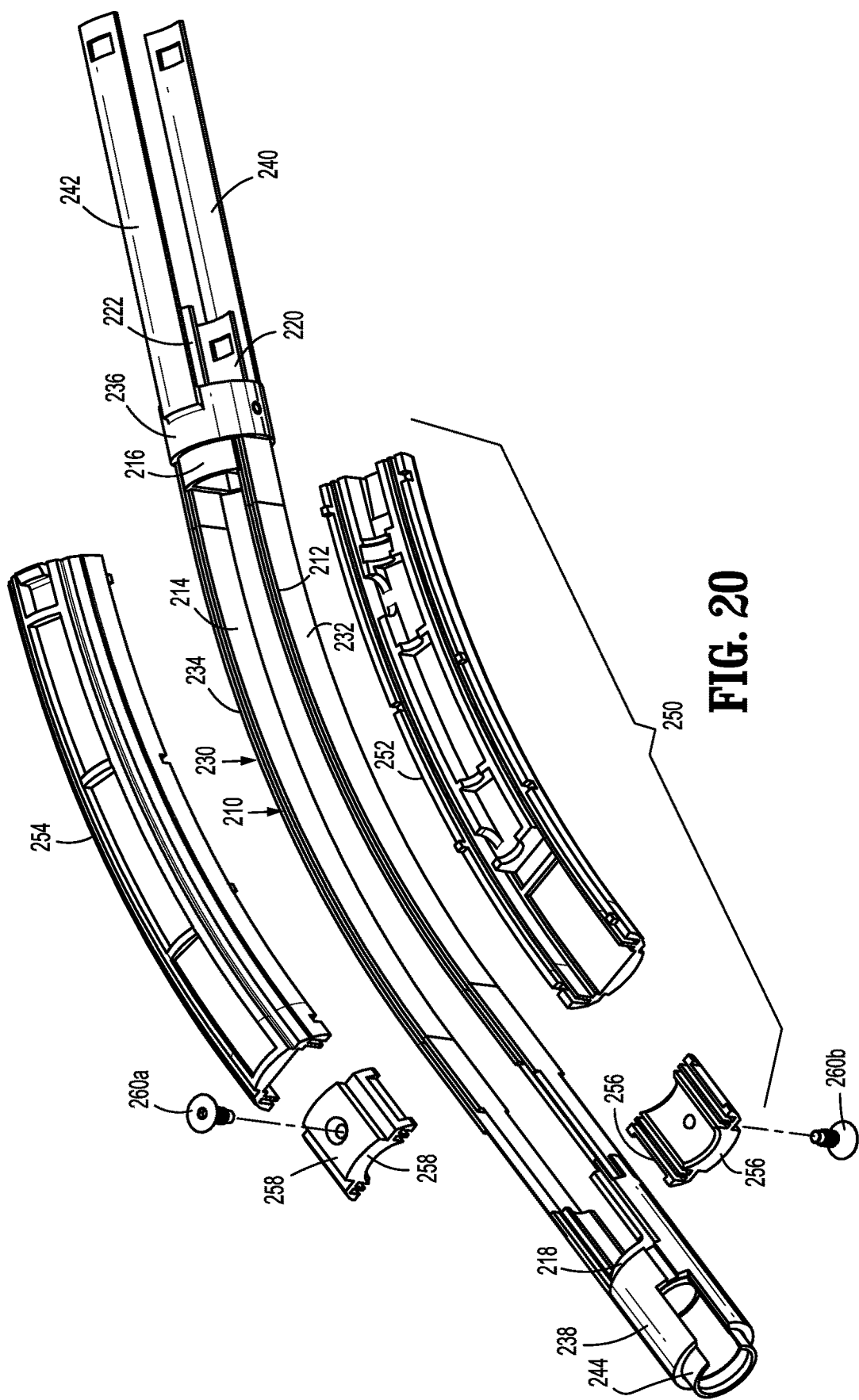
FIG. 20 is a perspective side view of the inner and outer flexible band assemblies of FIGS. 18 and 19 and an exploded view of a frame assembly of the extension assembly of FIG. 17.
Figure 21:
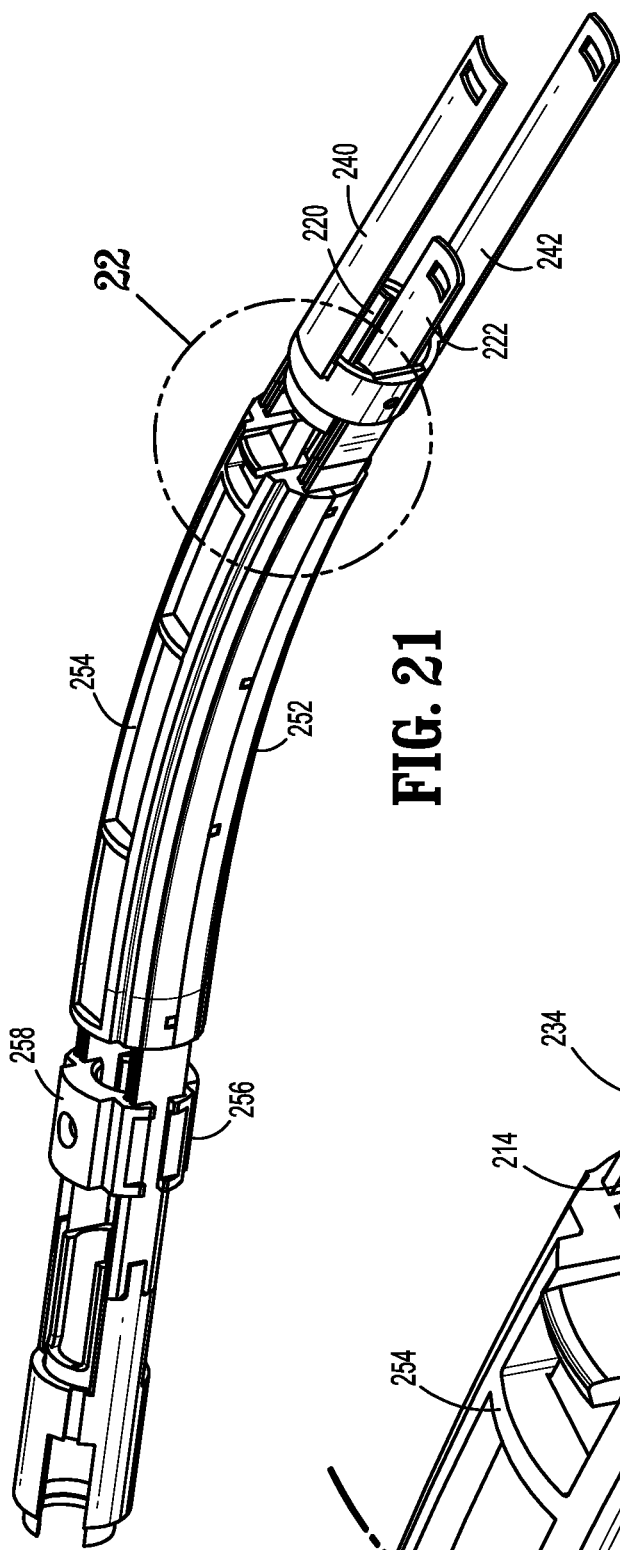
FIG. 21 is a perspective side view of the inner and outer flexible band assemblies and the frame assembly of FIG. 20.
Figure 22:
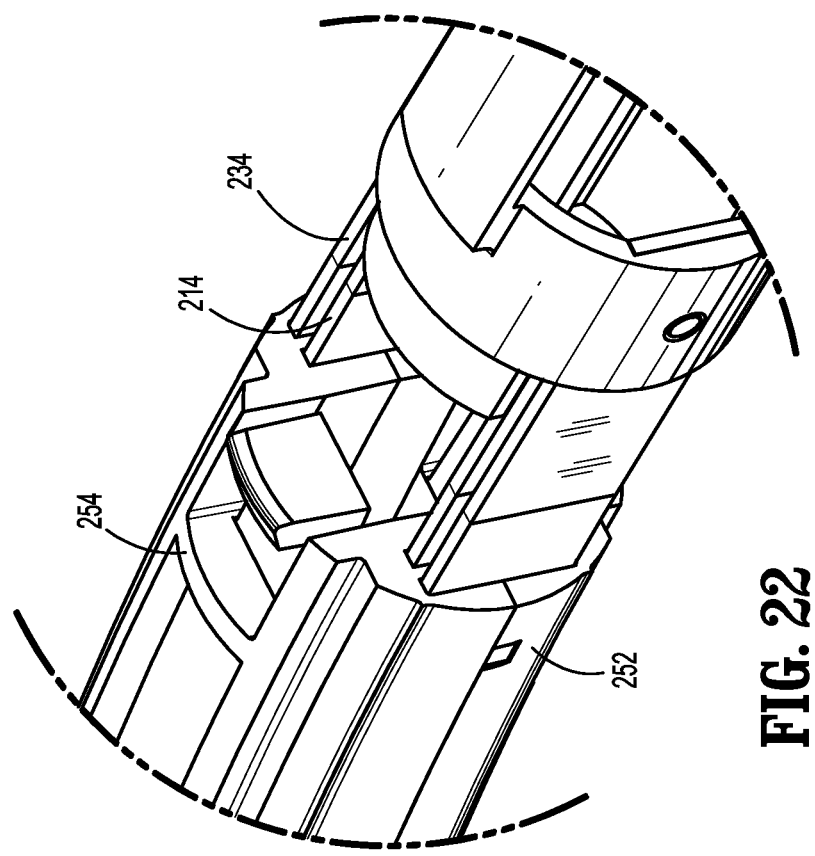
FIG. 22 is an enlarged view of the indicated area of detail of FIG. 21.
Figure 25:
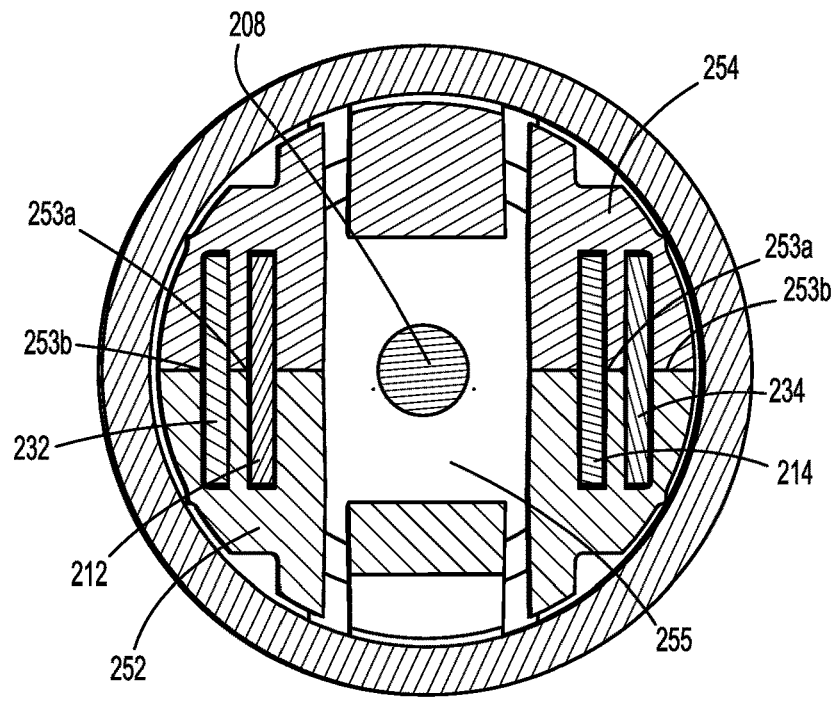
FIG. 25 is a cross-sectional end view taken along line 25-25 of FIG. 17.

With particular reference now to FIGS. 14-16, second pusher assembly 180 is substantially similar to first pusher assembly 160, and includes proximal and distal housing sections 182, 184, a planetary gear assembly 186 operably mounted within proximal housing section 182, a screw member 188 operably connected to planetary gear assembly 186 and rotatably supported within distal housing section 184, and a pusher member 190 operably connected to screw member 188 and slidably disposed within distal housing section 184. Planetary gear assembly 186 includes first and second planetary gear systems 186a, 186b (FIG. 16). First planetary gear system 186a includes a central drive gear 192a mounted on a distal end of tubular connector 150 of drive transfer assembly 130 and a plurality of planetary gears 194a rotatably mounted to a rotatable support ring 196.

Each planetary gear 194a of first planetary gear system 186a engages central drive gear 192a and a toothed inner surface 185 of proximal housing section 182. As central drive gear 192a rotates in a first direction, e.g., clockwise, each planetary gear 194a rotates in a second direction, e.g., counter-clockwise. As each planetary gear 194a rotates in the second direction, engagement of planetary gears 194*a* with toothed inner surface 185 of distal housing section 182 causes rotatable support ring 196 to rotate in the first direction. Conversely, rotation of central drive gear 192*a* in the second direction causes rotation of each planetary gear 194*a* in the first direction thereby causing rotation of rotatable support ring 196 in the second direction. The configuration of first planetary gear system 186*a* provides a reduction in the gear ratio. In this manner, the speed of rotation of rotatable support ring 194 is less than the speed of rotation of central drive gear 190*a*.

Second planetary gear system 186*b* includes a central drive gear 192*b* securely affixed to rotatable support ring 196 and a plurality of planetary gears 194*b* rotatably mounted to a proximal end surface 188*a* of screw member 188. Each planetary gear 194*b* of second planetary gear system 186*b* engages central drive gear 192*b* and toothed inner surface 185 of proximal housing section 182. As rotatable support ring 196 of first planetary gear system 186*a* rotates in the first direction thereby causing central drive gear 192*b* to also rotate in the first direction, each planetary gear 174*b* rotates in the second direction. As each planetary gear 194*b* rotates in the second direction, engagement of planetary gears 194*b* with toothed inner surface 185 of proximal housing section 182 causes screw member 188 to rotate in the first direction. Conversely, rotation of central drive gear 192*b* in the second direction causes rotation of each planetary gear 194*b* in the first direction, thereby causing screw member 198 to rotate in the second direction. The configuration of second planetary gear system 186*b* provides a reduction in the gear ratio. In this manner, the speed of rotation of screw member 188 is less than the speed of rotation of central drive gear 182*b*. First and second planetary gear systems 186*a*, 186*b* operate in unison to provide a reduction in the gear ratio between second rotatable proximal drive shaft 118 and screw member 188. In this manner, the reduction in the speed of rotation of screw member 188 relative to tubular connector 150 is a product of the reduction provided by the first and second planetary gear systems 186*a*, 186*b*.

Screw member 188 is rotatably supported within proximal housing portion 182 and includes a threaded distal end 188*b* that operably engages a threaded inner surface 190*a* of pusher member 190. As screw member 188 is rotated in the first direction, engagement of threaded distal end 188*b* of screw member 188 with threaded inner surface 190*a* of pusher member 190 (which is keyed to permit axial translation and prevent rotation thereof) causes longitudinal advancement of pusher member 190. Conversely, rotation of screw member 188 in the second direction causes retraction of pusher member 190.

Pusher member 190 of second pusher assembly 180 of adapter assembly 100 includes a pair of tabs 198 formed on a distal end thereof for engaging connector extensions 220, 224 (FIG. 18) of inner flexible band assembly 220 (FIG. 18) of extension assembly 200 (FIG. 17). Although shown as tabs 198, it is envisioned that pusher member 190 may include any structure suitable for selectively engaging connector extensions 240, 242 of outer flexible band 230 of extension assembly 200.

Turning now to FIGS. 17-34, extension assembly 200 for operably connecting adapter assembly 100 (FIG. 3) with a circular loading unit, e.g., loading unit 40 (FIG. 34) and an anvil assembly, e.g., anvil assembly 50 (FIG. 34) will be described. In particular, a proximal end 202 of extension assembly 200 operably connects with distal end 104 (FIG. 3) of adapter assembly 100 (FIG. 3) and a distal end 204 of extension assembly 200 operably connects with loading unit 40 and anvil assembly 50. As shown, extension assembly 200 provides a slight curvature between proximal and distal end 202, 204. In an alternative embodiment, extension assembly 200 may be straight or may include a greater curvature. In accordance with the present disclosure, extension assembly 200 may be substantially or fully rigid along its entire length.

Although extension assembly 200 will be shown and described as being used to connect loading unit 40 and anvil assembly 50 to adapter assembly 100 (FIG. 3), it is envisioned that the aspects of the present disclosure may be modified for use with various loading units, anvil assemblies, and adapter assemblies. Exemplary loading units and anvil assemblies are described in commonly owned U.S. Pat. Nos. 8,590,763 and 9,579,099, and U.S. patent application Ser. No. 14/056,301, filed Oct. 17, 2013 (now U.S. Pat. No. 10,463,365), the contents of each being incorporated herein by reference in their entirety.

Extension assembly 200 includes an inner flexible band assembly 210 (FIG. 18), about an outer flexible band assembly 230 (FIG. 19) slidably disposed about inner flexible band assembly 210, a frame assembly 250 (FIG. 20) for supporting inner and outer flexible band assemblies 210, 230, a trocar assembly 270 (FIG. 28) operably received through inner and outer flexible band assemblies 210, 230, and a connector assembly 290 for securing loading unit 40 (FIG. 34) to extension assembly 200. An outer sleeve 206 (FIG. 17) is received about frame assembly 250 and trocar assembly 270, and inner and outer flexible band assemblies 210, 230 are slidably received through outer sleeve 206. As will be described in further detail below, extension assembly 200 may include a drive shaft 208 operably connected to trocar assembly 270 and extending through proximal end 202 of extension assembly 200.

With reference to FIG. 18, inner flexible band assembly 210 includes first and second inner flexible bands 212, 214, a support ring 216, a support base 218, and first and second connection extensions 220, 222. Proximal ends 212*a*, 214*a* of respective first and second inner flexible bands 212, 214 are laterally spaced apart and securely attached to support ring 216. Distal ends 212*b*, 214*b* of first and second inner flexible bands 212, 214 are laterally spaced apart and securely attached to a proximal end 218*a* of support base 218. Each of first and second inner flexible bands 212, 214 may be attached to support ring 216 and/or support base 218 in any suitable manner, including, for example, by press-fitting, welding, adhesives, and/or with mechanical fasteners. As will be described in further detail below, inner flexible band assembly 210 is configured to be slidably received about trocar assembly 270 (FIG. 28) and within outer flexible band assembly 230 (FIG. 19) and outer sleeve 206 (FIG. 17).

First and second connection extensions 220, 222 of inner flexible band assembly 210 extend proximally from support ring 216 and operably connect inner flexible band assembly 210 with pusher member 190 (FIG. 15) of second pusher assembly 180 (FIG. 15) of adapter assembly 100 (FIG. 3). In particular, each of first and second connection extensions 220, 222 define respective openings 221, 223 configured to receive tabs 198 (FIG. 15) of pusher member 190 (FIG. 15) of second pusher assembly 180. Receipt of tabs 198 of pusher member 190 within openings 221, 223 of respective first and second extensions 220, 222 secure inner flexible band assembly 210 of extension assembly 200 with second pusher assembly 180 of adapter assembly 100. First and second connection extensions 220, 222 may be integrally formed with support ring 216, or attached thereto in any suitable manner.

Figure 34:
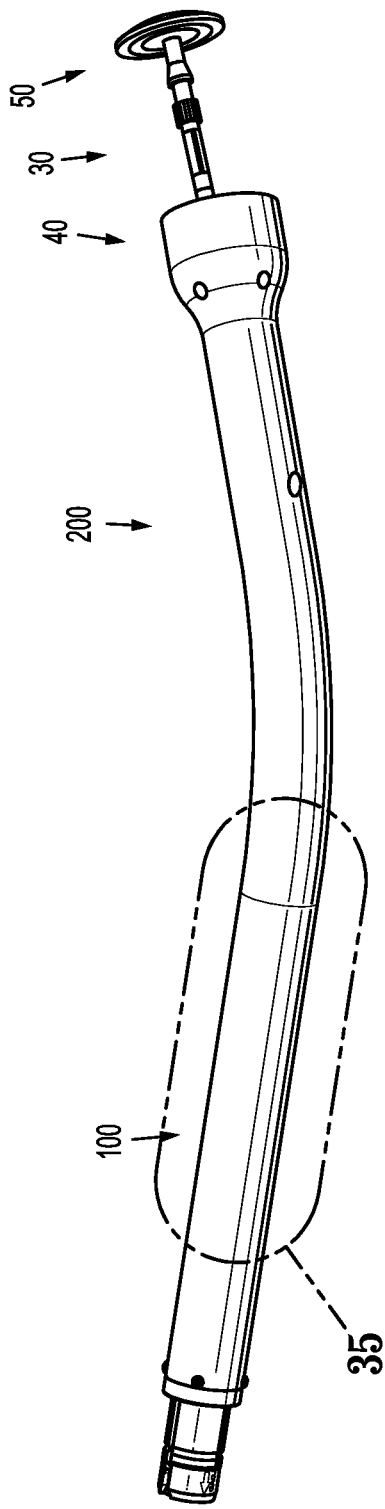
FIG. 34 is a perspective side view of the adapter assembly of FIG. 3 connected to the extension assembly of FIG. 17 and an end effector and an anvil assembly connected to the extension assembly.

Support base 218 extends distally from inner flexible bands 212, 214 and is configured to selectively connect extension assembly 200 with loading unit 40 (FIG. 34). Specifically, a distal end 218a of support base 218 includes a flange 224 for operable engagement with an axially movable assembly (not shown) of loading unit 40 (FIG. 34). In one embodiment, flange 224 is configured for connection with a knife assembly (not shown) of loading unit 40 (FIG. 34).

With reference now to FIG. 19, outer flexible band assembly 230 is substantially similar to inner flexible band assembly 210 and includes first and second flexible bands 232, 234 laterally spaced and connected on proximal ends 232a, 234a to a support ring 236 and on distal ends 234b, 234b to a proximal end 238a of a support base 238. Each of first and second outer flexible bands 232, 234 may be attached to support ring 236 and support base 238 in any suitable manner, including, for example, by press-fitting, welding, adhesives, and/or with mechanical fasteners. As will be described in further detail below, outer flexible band assembly 230 is configured to receive trocar assembly 270 (FIG. 28) therethrough.

First and second connection extensions 240, 242 of outer flexible band assembly 230 extend proximally from support ring 236 and operably connect outer flexible band assembly 230 with pusher member 170 (FIG. 12) of first pusher assembly 160 (FIG. 12) of adapter assembly 100 (FIG. 1). In particular, each of first and second connection extensions 240, 242 define respective openings 241, 243 configured to receive tabs 178 (FIG. 12) of pusher member 170 of first pusher assembly 180. Receipt of tabs 178 of pusher member 170 within openings 241, 243 of respective first and second extensions 240, 242 secures outer flexible band assembly 230 of extension assembly 200 with first pusher assembly 180 of adapter assembly 100. First and second connection extensions 240, 242 may be integrally formed with support ring 236, or attached thereto in any suitable manner.

Support base 238 extends distally from outer flexible bands 232, 234 and is configured to selectively connect extension assembly 200 with loading unit 40 (FIG. 34). Specifically, a distal end 238b of support base 238 includes a flange 244 for operable engagement with an axially movable assembly (not shown) of a loading unit (not shown). In one embodiment, flange 244 is configured for connection with a staple pusher assembly (not shown) of loading unit 40 (FIG. 34).

With reference now to FIGS. 20-26, frame assembly 250 includes first and second proximal spacer members 252, 254, and first and second distal spacer members 256, 258. When secured together, first and second proximal spacer members 252, 254 define a pair of inner longitudinal slots 253a for slidably receiving first and second flexible bands 212, 214 (FIG. 18) of inner flexible band assembly 210 (FIG. 18) and a pair of outer longitudinal slots 253b for slidably receiving first and second flexible bands 232, 234 (FIG. 19) of outer flexible band assembly 230 (FIG. 19). First and second proximal spacer members 252, 254 further define a longitudinal passage 255 for receipt of trocar assembly 270.

In one embodiment, and as shown, first and second proximal spacer members 252, 254 are formed of plastic and are secured together with a snap-fit arrangement. Alternatively, first and second proximal spacer members 252, 254 may be formed of metal or other suitable material and may be secured together in any suitable manner, including by welding, adhesives, and/or using mechanical fasteners.

First and second distal spacer members 256, 258 define a pair of inner slots 257a for slidably receiving first and second flexible bands 212, 214 (FIG. 18) of inner flexible band assembly 210 (FIG. 18) and a pair of outer slots 257b for slidably receiving first and second flexible bands 232, 234 (FIG. 19) of outer flexible band assembly 230 (FIG. 19). First and second distal spacer members 256, 258 further define a longitudinal passage 259 for receipt of trocar assembly 270.

Figure 26:
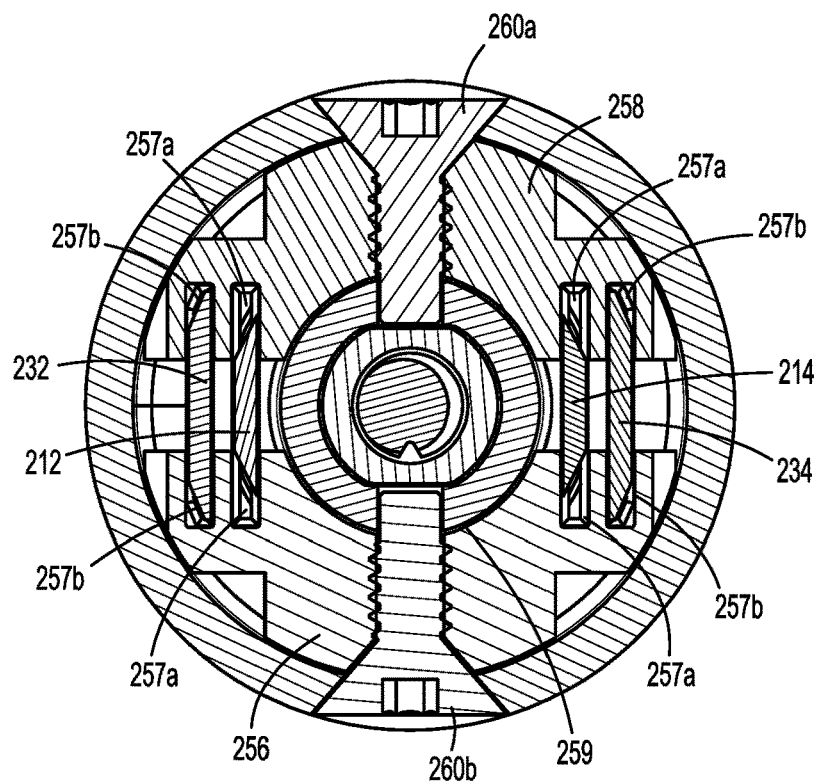
FIG. 26 is a cross-sectional end view taken along line 26-26 of FIG. 17.

In one embodiment, and as shown, each of first and second distal spacer members 256, 258 are secured about inner and outer flexible band assemblies 210, 230 and to outer sleeve 206 (FIG. 17) by a pair of screws 260a, 260b (FIG. 26). Alternatively, first and second distal spacer members 256, 258 may be secured together in any suitable manner, including by welding, adhesives, and/or using mechanical fasteners. First and second distal spacer members 256, 258 may be formed of metal or any other suitable material.

Figure 27:
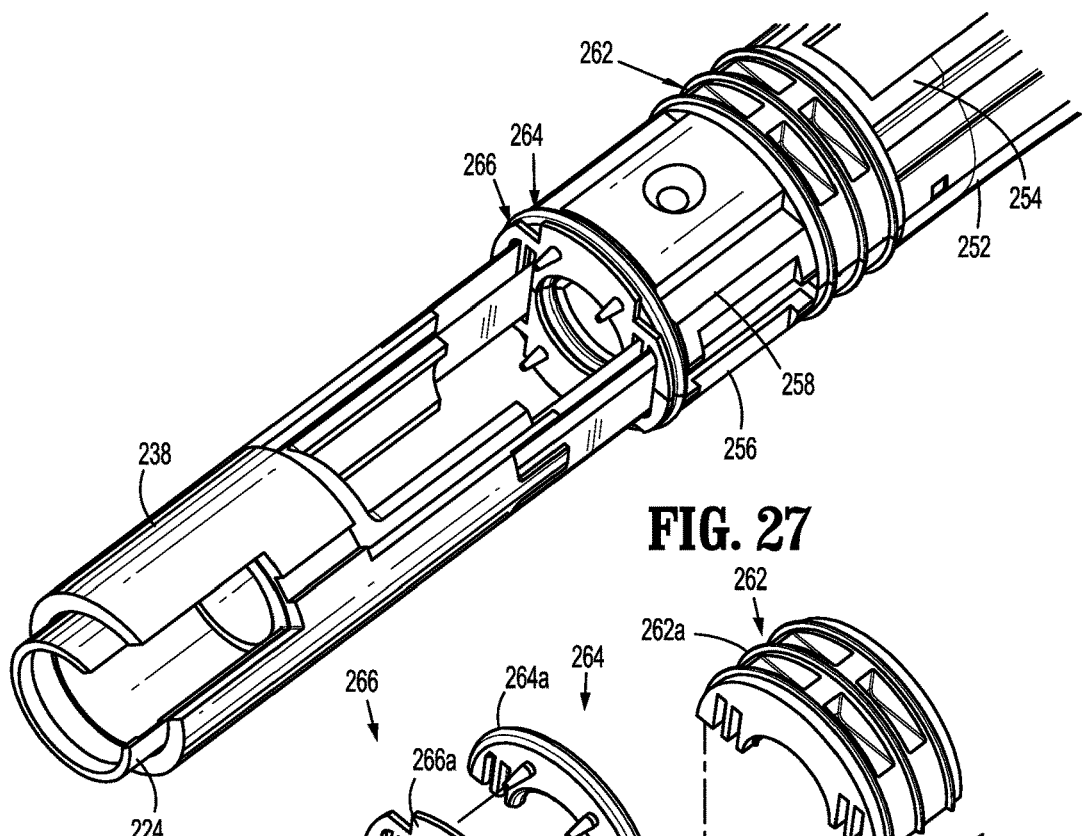
FIG. 27 is an enlarged perspective side view of a distal end of the inner and outer flexible band assemblies and the frame assembly of FIG. 20 including a proximal seal member and first and second distal seal members.
Figure 28:
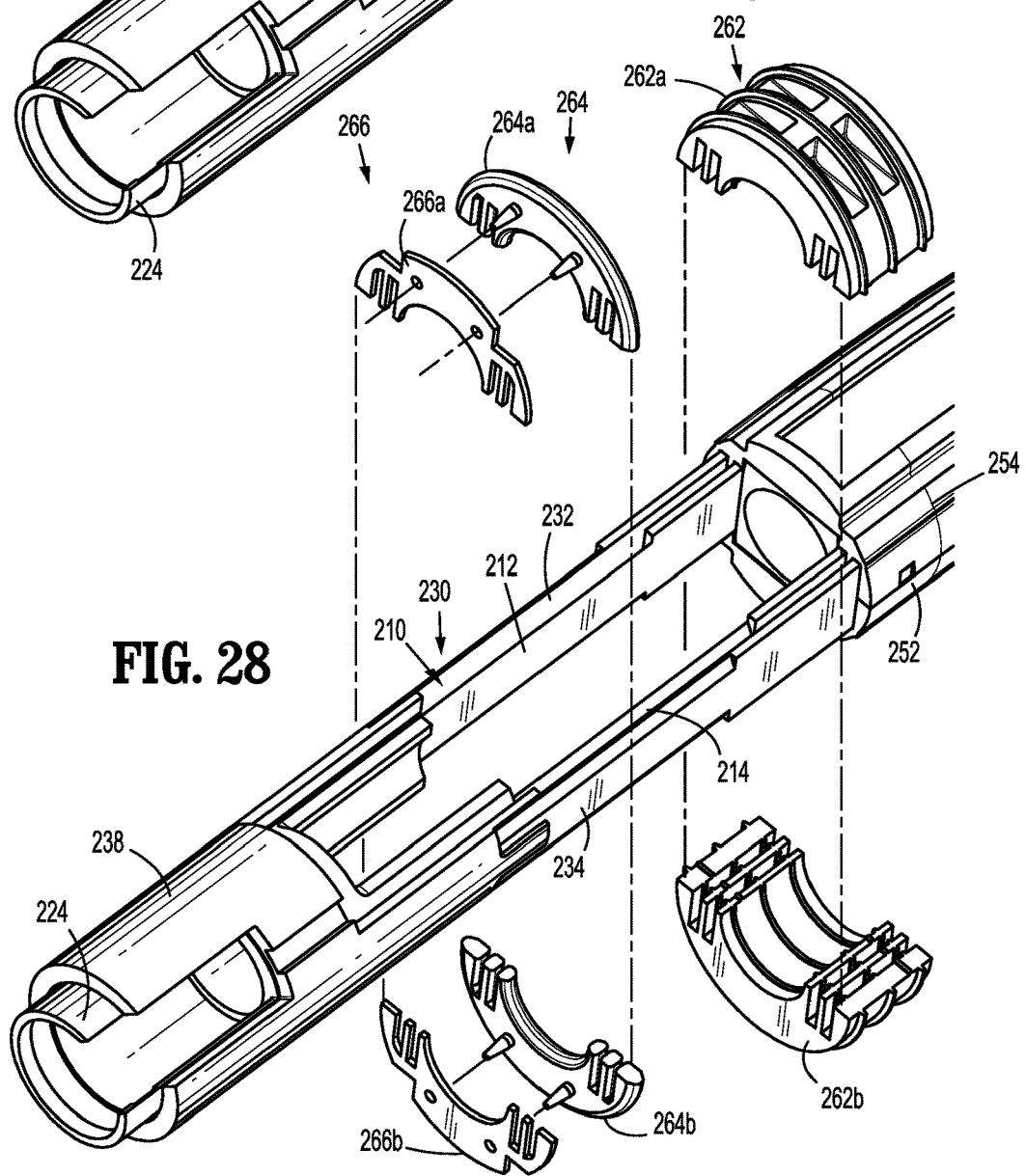
FIG. 28 is an exploded perspective view of the proximal seal member and first and second distal seal members of FIG. 27.
Figure 29:
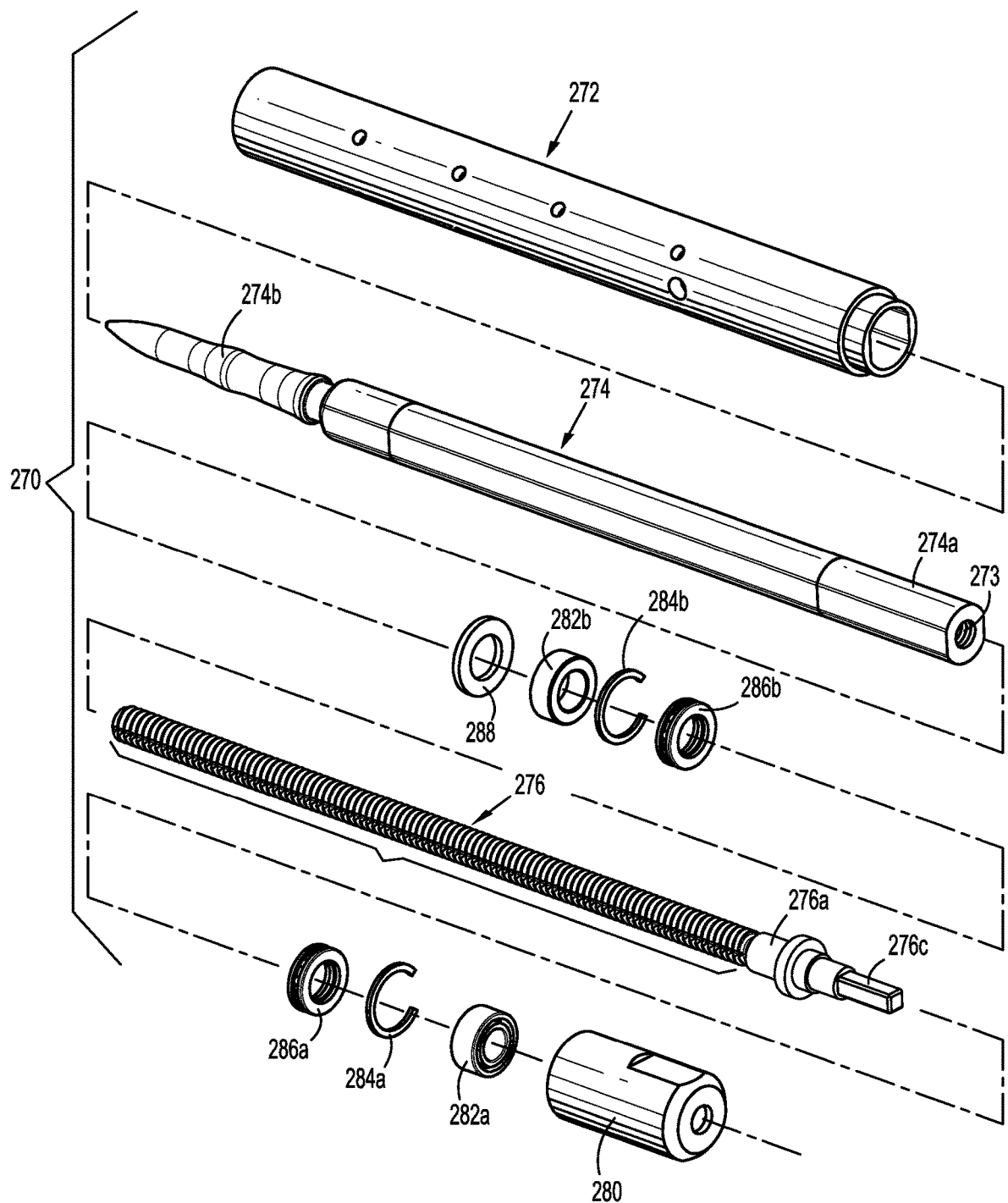
FIG. 29 is an exploded view of a trocar assembly of the extension assembly of FIG. 17.

With reference now to FIGS. 27 and 28, frame assembly 250 further includes a proximal seal member 262 and first and second distal seal members 264, 266. Each of proximal seal member 252 and first and second distal seal members 264, 266 include seals halves 262a, 262b, 264a, 264b, 266a, 266b, respectively. Proximal seal member 262 is received between first and second proximal spacer members 252, 254 and first and second distal spacer members 256, 258. First half 264a of first distal seal member 264 is secured to first half 266a of second distal seal member 266 and second half 264b of first distal seal member 264 is secured to second half of second distal seal member 266. Proximal seal member 262 and first and second distal seal members 264, 266 engage outer sleeve 206 (FIG. 17), inner and outer flexible bands 212, 214 and 232, 234 of respective inner and outer flexible band assemblies 210, 230 and trocar assembly 270 (FIG. 28) in a sealing manner. In this manner, proximal seal member 262 and first and second distal seal members 264, 266 operate to provide a fluid tight seal between distal end 204 and proximal end 202 of extension assembly 200.

With reference to FIGS. 29-32, trocar assembly 270 of extension assembly 200 includes an outer housing 272, a trocar member 274 slidably disposed within tubular outer housing 272, and a drive screw 276 operably received within trocar member 274 for axially moving trocar member 274 relative to tubular housing 272. In particular, trocar member 274 includes a proximal end 274a having an inner threaded portion 275 which engages a threaded distal portion 276b of drive screw 276. As drive screw 276 is rotated within trocar member 274, engagement of inner threaded portion 275 of trocar member 274 with threaded distal portion 276b of drive screw 276 causes longitudinal movement of trocar member 274 within outer housing 272 of trocar assembly 270. Rotation of drive screw 276 in a first direction causes longitudinal advancement of trocar member 274 and rotation of drive screw 276 in a second direction causes longitudinal retraction of trocar member 274. A distal end 274b of trocar member 274 is configured to selectively engage anvil assembly 50 (FIG. 34).

A bearing assembly 278 is mounted to a proximal end 272a of outer housing 272 of trocar assembly 270 for rotatably supporting a proximal end 276a of drive screw 276 relative to outer housing 272 and trocar member 274. Bearing assembly 278 includes a housing 280, proximal and distal spacers 282a, 282b, proximal and distal retention clips 284a, 284b, proximal and distal bearings 286a, 286b, and a washer 288. As shown, proximal end 276a of drive screw 276 includes a flange 276c for connection with a link assembly 277. A distal portion 277b of link assembly 277 is pivotally received between first and second proximal spacer members 252, 254 and operably engages flange 276c on drive screw 276. A proximal end 277a of link assembly 277 is configured for operable engagement with a distal end 208b of drive shaft 208.

With reference now to FIGS. 32 and 33, connector assembly 290 of extension assembly 200 includes a tubular connector 292 attached to a distal end 206a of outer sleeve 206 and about distal ends of inner and outer flexible assemblies 210, 230 (FIG. 26) and trocar assembly 270. In particular, a proximal end 292a of tubular connector 292 is received within and securely attached to distal end 206b of outer sleeve 206 by a retaining clip 294. An O-ring 296 forms a fluid tight seal between tubular connector 292 of connector assembly 290 and outer sleeve 206. A distal end 292b of tubular connector 292 is configured to selectively engage a proximal end of loading unit 40 (FIG. 34). Distal end 292b of tubular connector 292 engages the circular loading unit with a snap-fit arrangement, bayonet coupling, or in another suitable manner.

Figure 35:
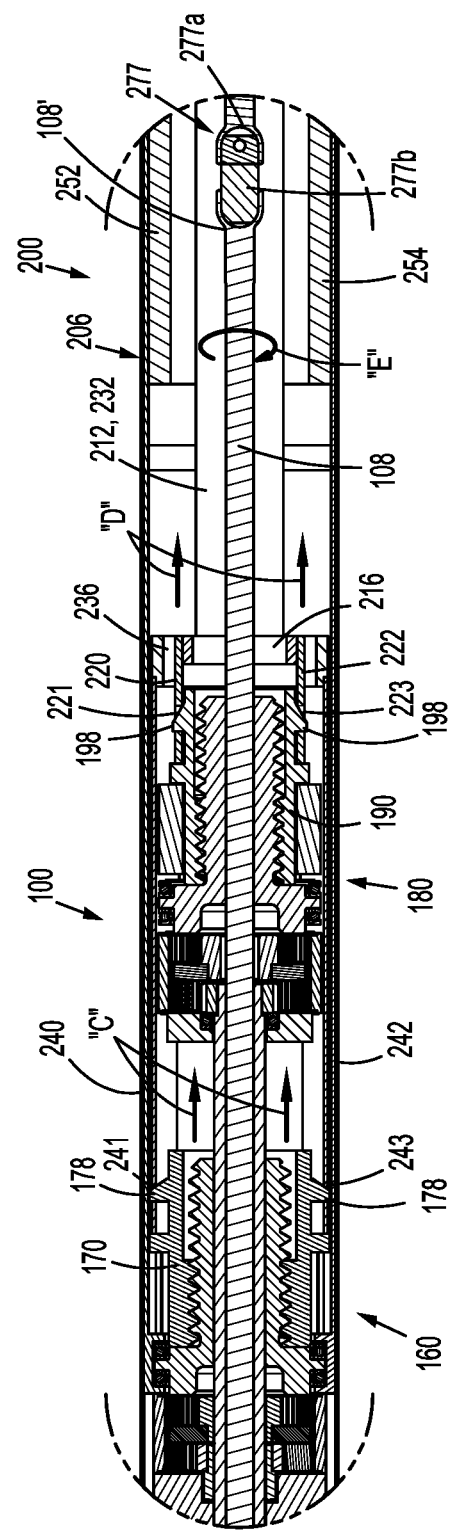
FIG. 35 is an enlarged cross-sectional side view of the indicated area of detail of FIG. 34.
Figure 36:
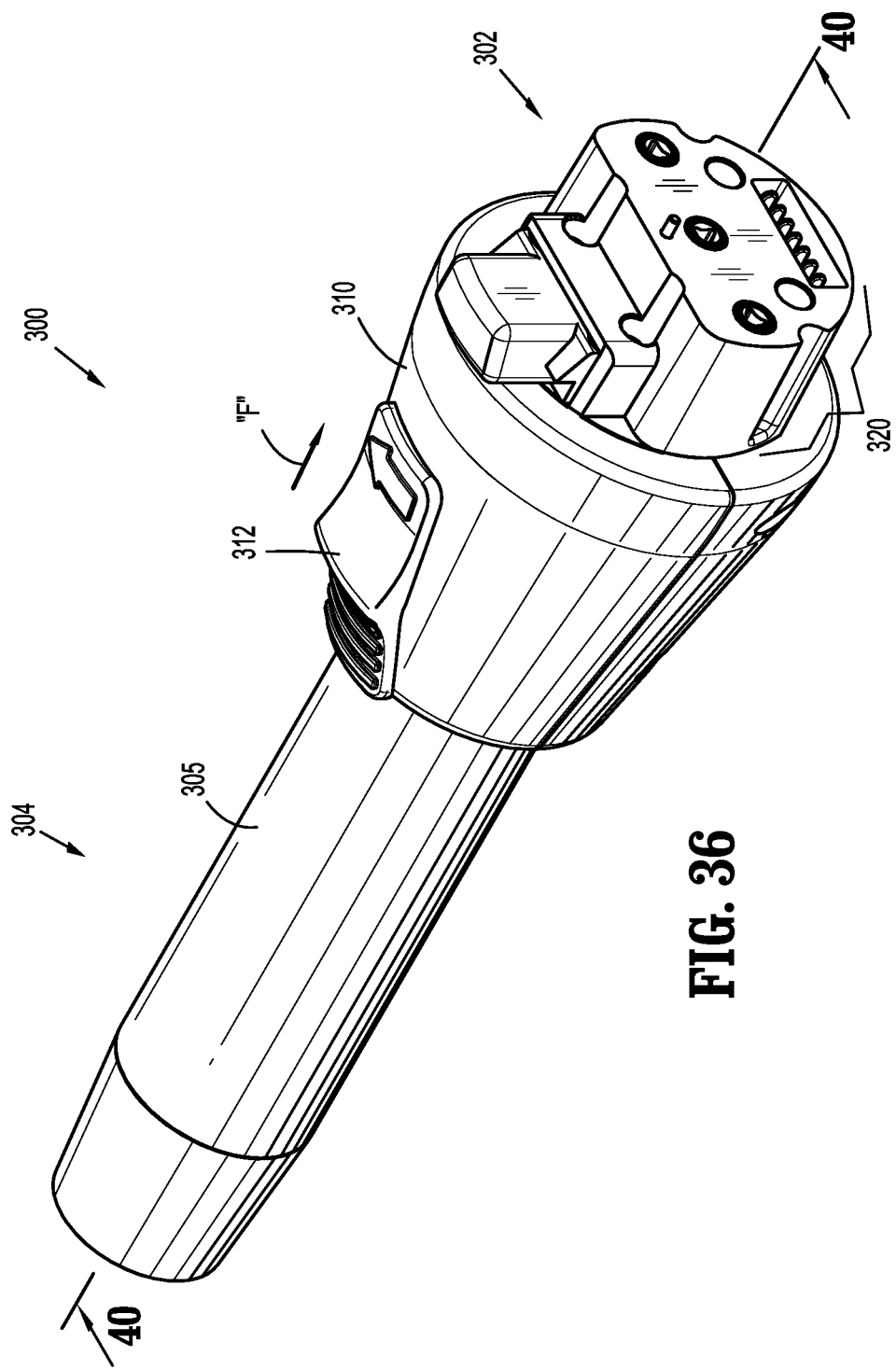
FIG. 36 is a rear, perspective view of an adapter assembly according to another embodiment of the present disclosure.
Figure 37:
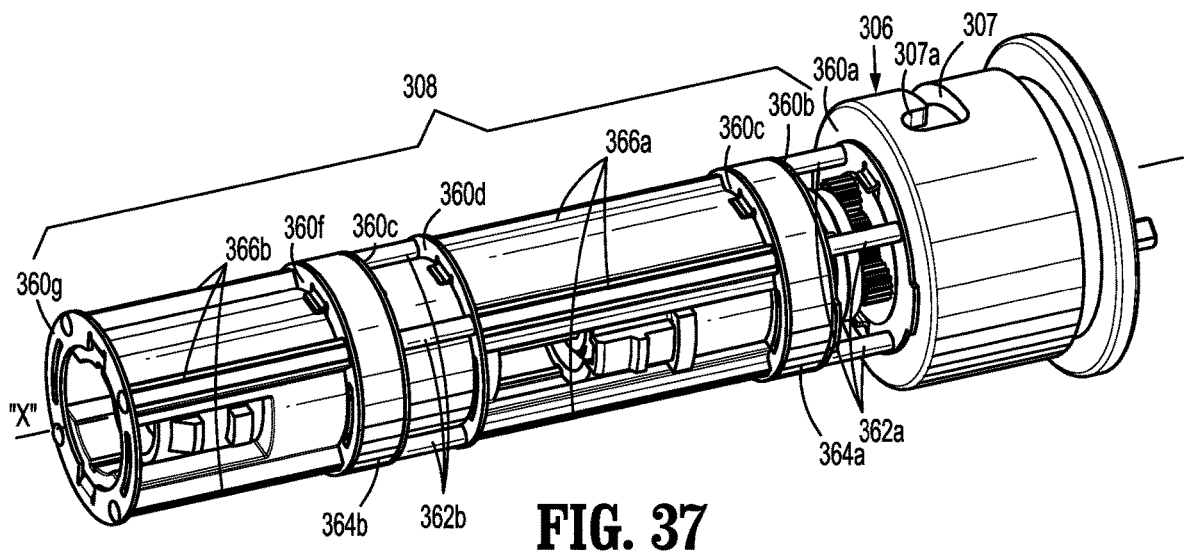
FIG. 37 is a perspective side view of the adapter assembly of FIG. 36 with an outer sleeve and a handle member removed.
Figure 38:
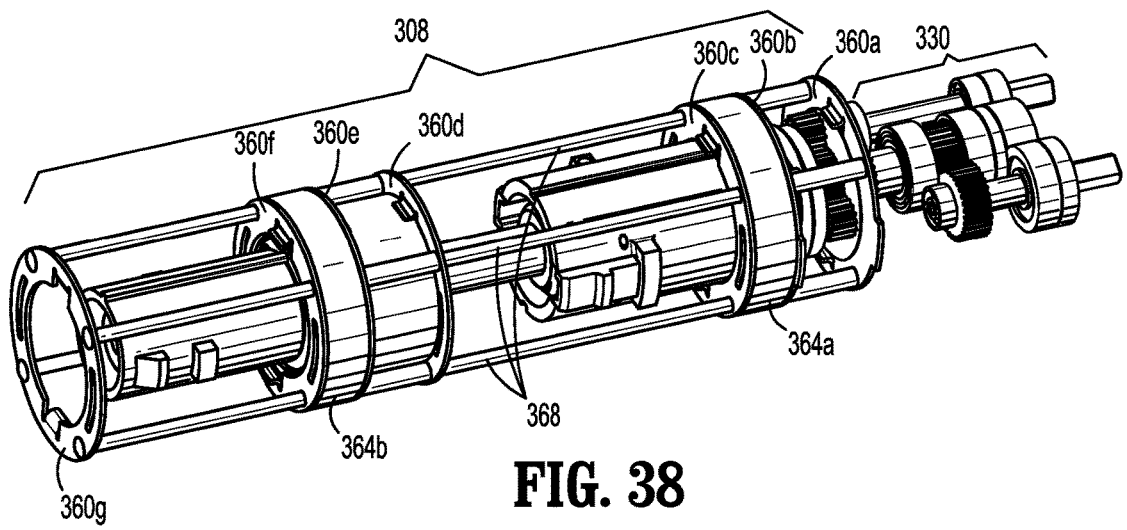
FIG. 38 is a perspective side view of the adapter assembly of FIG. 37 with a base and a housing member removed.
Figure 39:
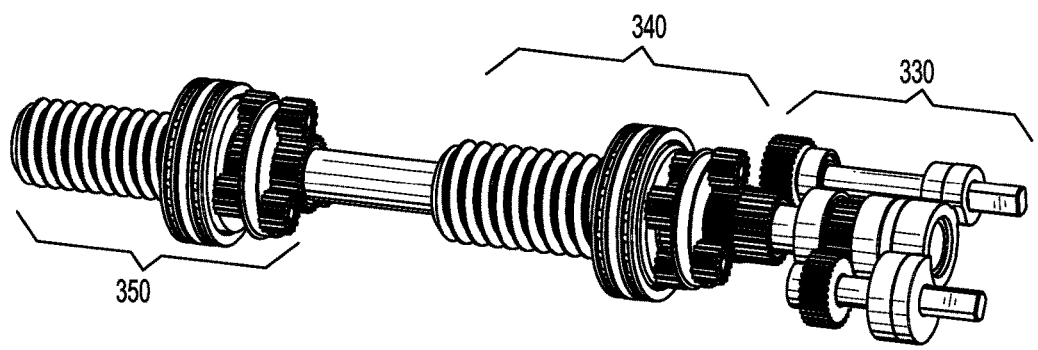
FIG. 39 is a perspective side view of the adapter assembly of FIG. 38 with a support structure removed.
Figures 40, 41:
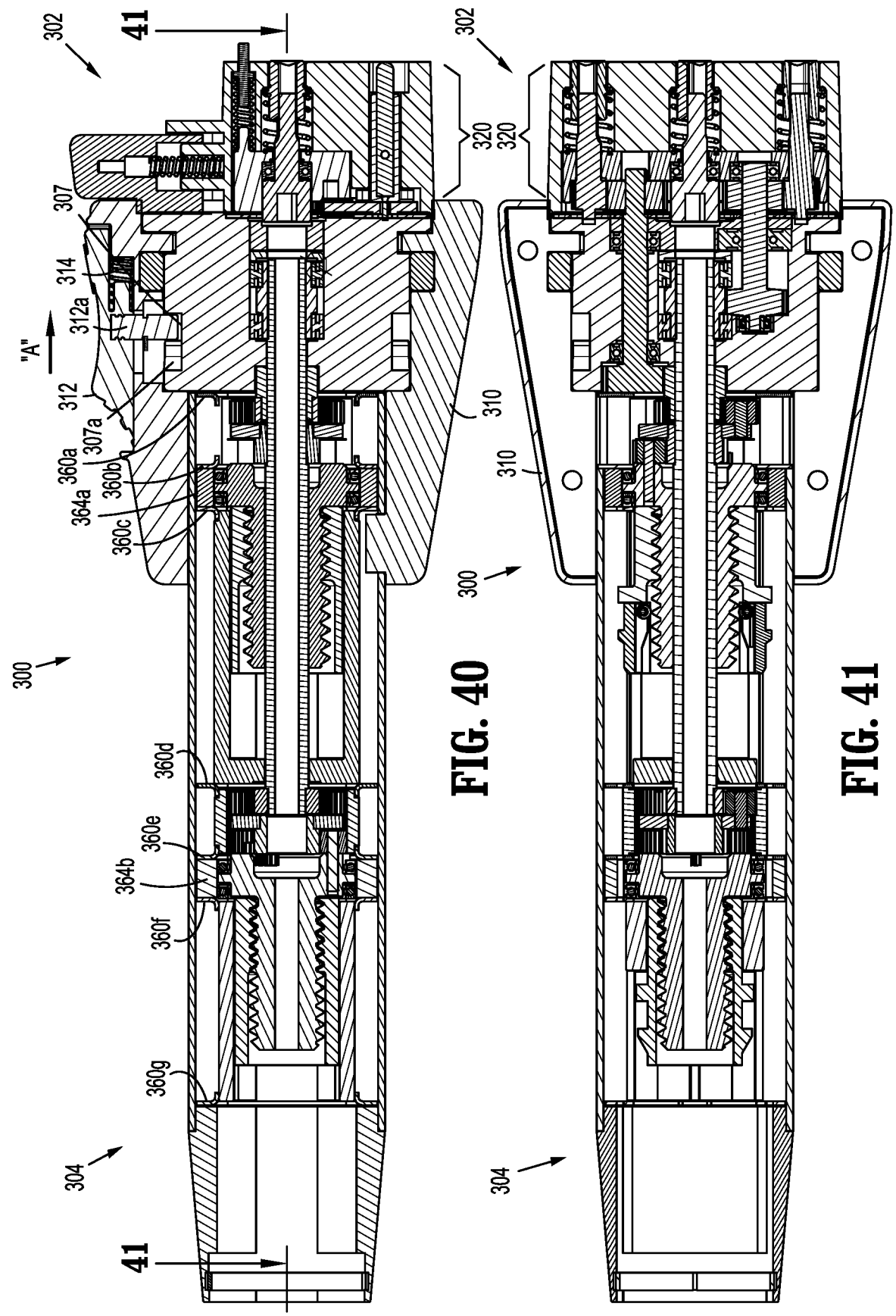
FIG. 40 is a cross-sectional side view taken along line 40-40 of FIG. 36.
FIG. 41 is a cross-sectional side view taken along line 41-41 of FIG. 40.

With reference now to FIGS. 34 and 35, extension assembly 200 is connected to adapter assembly 100 by receiving proximal end 202 (FIG. 17) of extension assembly 200 within distal end 104 of adapter assembly 100. In particular, first and second connection extensions 220, 240, 222, 242 of respective inner and outer flexible band assemblies 210, 230 are received within sleeve 106 of adapter assembly 100 such that tabs 178 of pusher member 170 of first pusher assembly 160 of adapter assembly 100 are received within openings 241, 243 of respective first and second connection extensions 240, 242 of outer flexible band assembly 230 to secure outer flexible band assembly 230 with first pusher assembly 160 and tabs 198 of pusher member 190 of second pusher assembly 180 of adapter assembly 100 are received within openings 221, 223 of first and second connection extensions 221, 223 of inner flexible band assembly 210 to secure inner flexible band assembly 210 with second pusher assembly 180.

As noted above, adapter assembly 100 may include a drive shaft 108 (FIG. 3) that extends from distal end 104 of adapter assembly 100. Alternatively, extension assembly 200 may include a drive shaft 208 extending from proximal portion 202 of extension assembly 200. In the event that both adapter assembly 100 includes drive shaft 108 and extension assembly 200 includes drive shaft 208, prior to receipt of proximal portion 202 of extension assembly 200 within distal end 104 of extension assembly 100, one of drive shaft 108, 208 must be removed from respective adapter assembly 100 and extension assembly 200. During receipt of proximal portion 202 of extension assembly 200 within distal end 102 of adapter assembly 100, either distal end 108b (FIG. 35) of drive shaft 108b (FIG. 35) engages proximal portion 277b (FIG. 35) of link assembly 277, or proximal end 208a (FIG. 17) of drive shaft 208 (FIG. 17) is received within socket 145 of drive member 140 of drive transfer assembly 130 of extension assembly 100 (FIG. 12).

After extension assembly 200 is operably engaged with adapter assembly 100, and adapter assembly 100 is operably engaged with surgical device 10 (FIG. 1), loading unit 40 (FIG. 34) of end effector 30 (FIG. 34) may be attached to connector assembly 290 of extension assembly 200 and an anvil assembly 50 (FIG. 34) may be attached to distal end 274b of trocar 274 of extension assembly 200 in a conventional manner. During actuation of loading unit 40 and anvil assembly 50, longitudinal advancement of pusher member 190 of second pusher assembly 180 of adapter assembly 100, as described above, and as indicated by arrows "C" in FIG. 35, causes longitudinal advancement of outer flexible band assembly 230 of extension assembly 200 and longitudinal advancement of pusher member 170 of first pusher assembly 160, as described above, and as indicated by arrows "D" in FIG. 35, causes longitudinal advancement of inner flexible band assembly 210. Rotation of drive shaft 108 in a first direction, as described above, and as indicated by arrow "E", causes advancement of trocar 274 of extension assembly 200. Conversely, longitudinal retraction of pusher member 190 causes longitudinal retraction of outer flexible band assembly 230, longitudinal retraction of pusher member 170 causes longitudinal retraction of inner flexible band assembly 210, and rotation of drive shaft 108 in a second direction causes retraction of trocar 274 of extension assembly 200.

In one embodiment, inner flexible band assembly 210 is operably connected to a knife assembly (not show) of loading unit 40 (FIG. 34) of end effector 30 (FIG. 34) attached to connection assembly 290 of extension assembly 200, outer flexible band assembly 230 is operably connected to a staple driver assembly (not shown) of loading unit 40, and trocar 274 is operably connected to anvil assembly 50 (FIG. 34) of end effector 30 (FIG. 34). In this manner, longitudinal movement of inner flexible band assembly 210 causes longitudinal movement of the knife assembly, longitudinal movement of outer flexible band assembly 230 causes longitudinal movement of the staple driver assembly, and longitudinal movement of trocar 274 causes longitudinal movement of anvil assembly 50 relative to loading unit 40.

With reference to FIGS. 36-41, an adapter assembly according to another embodiment of the present disclosure is shown as adapter assembly 300. Adapter assembly 300 is substantially similar to adapter assembly 100 described hereinabove and will only be described as it relates to the differences therebetween.

As will become apparent from the following description, the configuration of adapter assembly 300 permits rotation of a distal portion 304 of adapter assembly 300 about a longitudinal axis "X" (FIG. 37), relative to a proximal portion 302 of adapter assembly 300. In this manner, an end effector, e.g. end effector 30 (FIG. 34) secured to distal portion 304 of adapter assembly 300 or an end effector secured to an extension assembly, e.g., extension assembly 200 (FIG. 17) which is secured to distal portion 304 of adapter assembly 300 is rotatable about longitudinal axis "X" independent of movement of the surgical device (not shown) to which adapter assembly 300 is attached.

Adapter assembly 300 includes a base 306 and a support structure 308 rotatable relative to base 306 along longitudinal axis "X" of adapter assembly 300. A rotation handle 310 is rotatably secured to base 306 and fixedly secured to a proximal end of support structure 308. Rotation handle 310 permits longitudinal rotation of distal portion 304 of adapter assembly 300 relative to proximal end 302 of adapter assembly 300. As will be described in further detail below, a latch 312 is mounted to rotation handle 310 and selectively secures rotation handle 310 in a fixed longitudinal position.

Proximal portion 302 of adapter assembly 300 includes a drive coupling assembly 320 and a drive transfer assembly 330 operably connected to drive coupling assembly 320. Distal portion 304 of adapter assembly 300 includes a first pusher assembly 340 operably connected to drive transfer assembly 330, and a second pusher assembly 350 operably connected to drive transfer assembly 330. Drive coupling assembly 320 and drive transfer assembly 330 are mounted within base 306, and thus, remain rotationally fixed relative to the surgical device (not shown) to which adapter assembly 300 is attached. First pusher assembly 340 and second pusher assembly 350 are mounted within support structure 308, and thus, are rotatable relative to the surgical device (not shown) to which adapter assembly 300 is attached.

Drive coupling assembly 320 is configured to selectively secure adapter assembly 300 to a surgical device (not shown). For a detailed description of an exemplary surgical device and drive coupling assembly, please refer to commonly owned U.S. patent application Ser. No. 14/550,183, filed Nov. 21, 2014 (now U.S. Patent Publication No. 2015/0157321), and U.S. patent application Ser. No. 14/822,970, filed Aug. 11, 2015 (now U.S. Pat. No. 10,123,799), the content of each of which being incorporated by reference herein in their entirety.

Rotation knob 310 is rotatably secured to base 306. Latch 312 includes a pin 312a (FIG. 40) configured to lock rotation knob 310 relative to base 306. In particular, pin 312a of latch 312 is received within a slot 307 formed in base 306 and is biased distally by a spring 314 into a notch 307a (FIG. 40) formed in base 306 and in communication with slot 307 to lock rotation knob 310 relative to base 306. Proximal movement of latch 312, as indicated by arrow "F" in FIG. 36, retracts pin 312a from within notch 307a to permit rotation of rotation knob 310 relative to base 306. Although not shown, it is envisioned that base 306 may define a number of notches radially spaced about base 306 and in communication with slot 307 that permit rotation knob 310 to be locked in a number of longitudinal orientations relative to base 306.

Drive transfer assembly 330, first drive pusher assembly 340, and second drive pusher assembly 350 of adapter assembly 300 are substantially identical to respective drive transfer assembly 130, first drive pusher assembly 160, and second drive pusher assembly 180 of adapter assembly 100 described hereinabove, and therefore, will only be described as relates to the differences therebetween.

Support structure 308 is fixedly received about first and second drive pusher assemblies 340, 350 and rotatably relative to base 306. As noted above, rotation knob 310 is fixedly secured to the proximal end of support structure 308 to facilitate rotation of support structure 308 relative to base 306. Support structure 308 is retained with outer sleeve 305 of adapter assembly 300 and is configured to maintain axial alignment of first and second drive pusher assemblies 340, 350. Support structure 308 may also reduce the cost of adapter assembly 300 when compared to the cost of adapter assembly 100.

Support structure 308 respectively includes first, second, third, fourth, fifth, sixth, and seventh plates 360a, 360b, 360c, 360d, 360e, 360f, 360g, a first and a second plurality of tubular supports 362a, 362b, first and second support rings 364a, 364b, a first and a second plurality of ribs 366a, 366b, and a plurality of rivets 368. From proximal to distal, first and second plates 360a, 360b are maintained in spaced apart relation to each other by the first plurality of tubular supports 362a, second and third plates 360b, 360c are maintained in spaced apart relation to each other by first support ring 364a, third and fourth plates 360c, 360d are maintained in spaced apart relation to each other by the first plurality of support ribs 366a, fourth and fifth plates 360d, 360e are maintained in spaced apart relation to each other by the second plurality of tubular supports 362b, fifth and sixth plates 360e, 360f are maintained in spaced apart relation to each other by second support ring 364b, and sixth and seventh plates 360f, 360g are maintained in spaced apart relation to each other by the second plurality of support ribs 366b. First, second, third, fourth, fifth, sixth, and seventh plates 360a-g are held together by a plurality of rivets 368 secured to first and seventh plates 360a, 360g and extending through second, third, fourth, fifth, and sixth plates 360b-360f, first and second support rings 364a, 364b, and respective first and second plurality of tubular support 362a, 362b.

Adapter assembly 300 operates in a substantially similar manner to adapter assembly 100 described hereinabove. In addition, as described in detail above, adapter assembly 300 is configured to permit rotation of an end effector, e.g., end effector 30 (FIG. 34) attached to adapter assembly 300 or attached to an extension assembly that is attached to adapter assembly 300 to be selectively rotated about longitudinal axis "X" (FIG. 37) during use.

Figure 42:
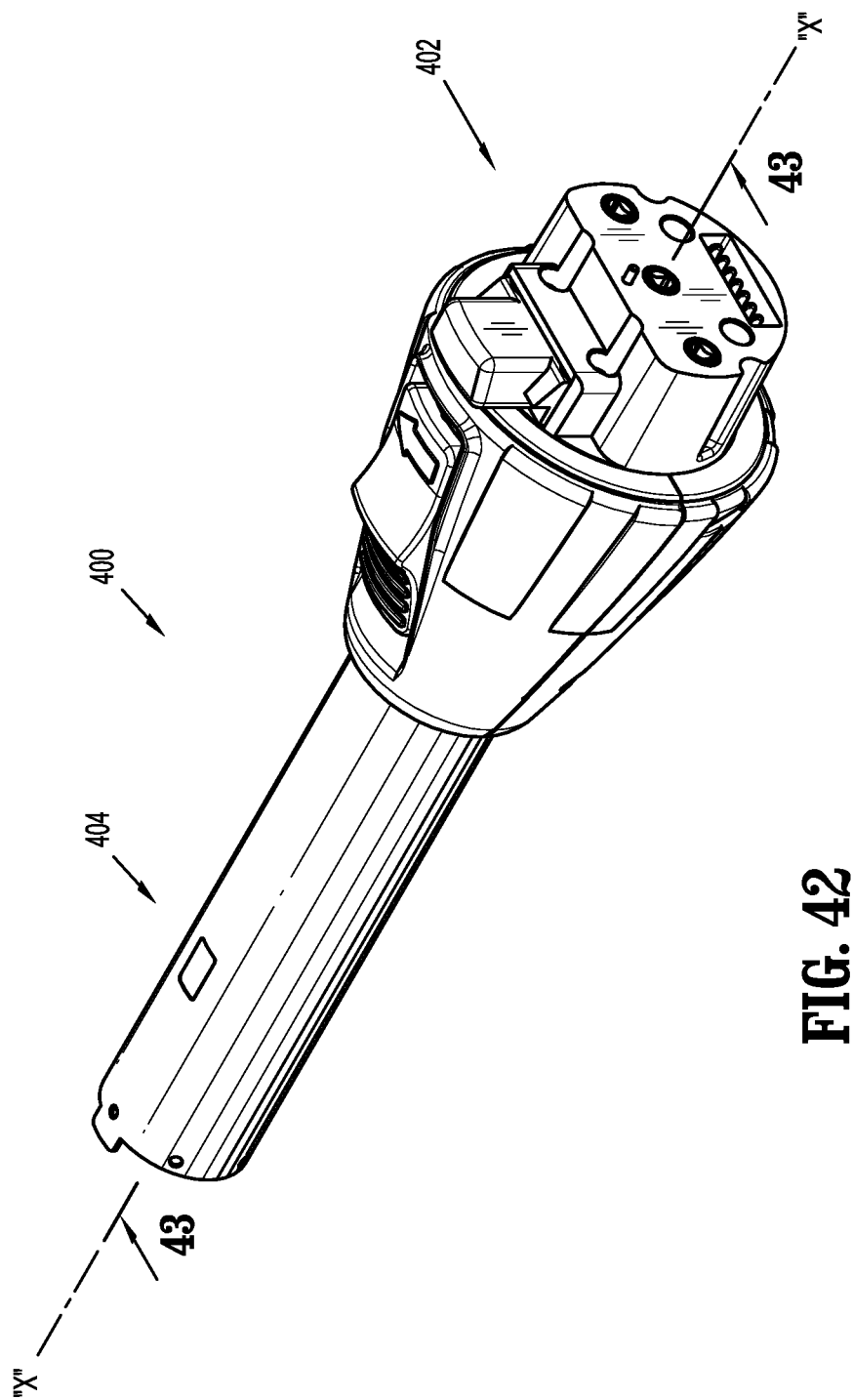
FIG. 42 is a rear, perspective view of an adapter assembly according to yet another embodiment of the present disclosure.
Figure 45:
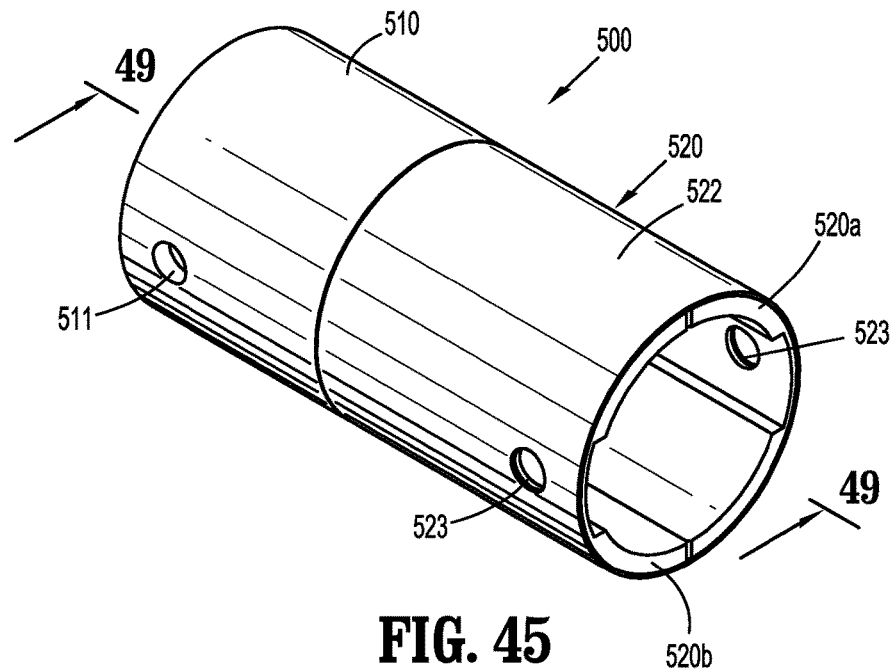
FIG. 45 is a perspective view of a connector assembly according to an embodiment of the present disclosure.
Figure 46:
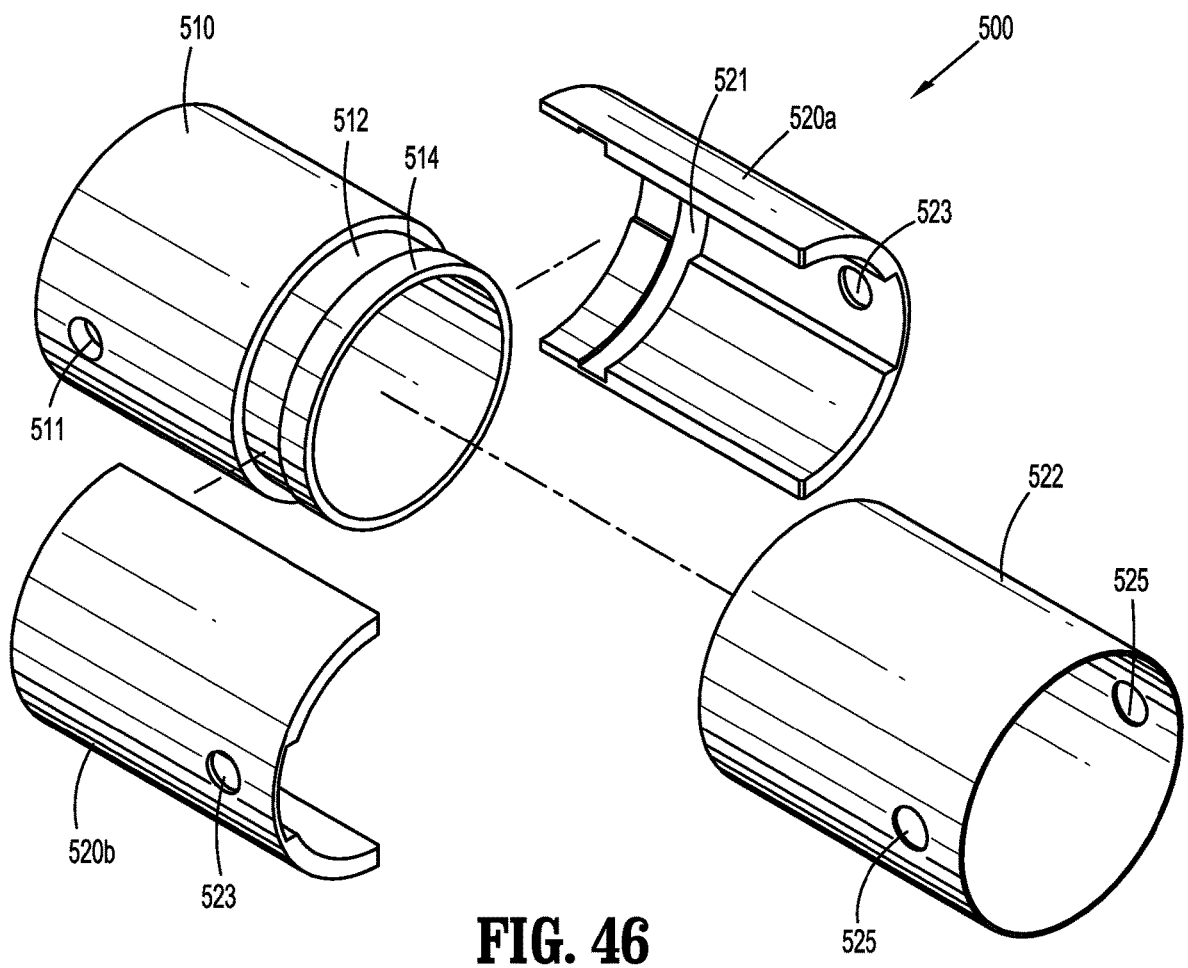
FIG. 46 is an exploded perspective view of the connector assembly of FIG. 45.
Figure 47:
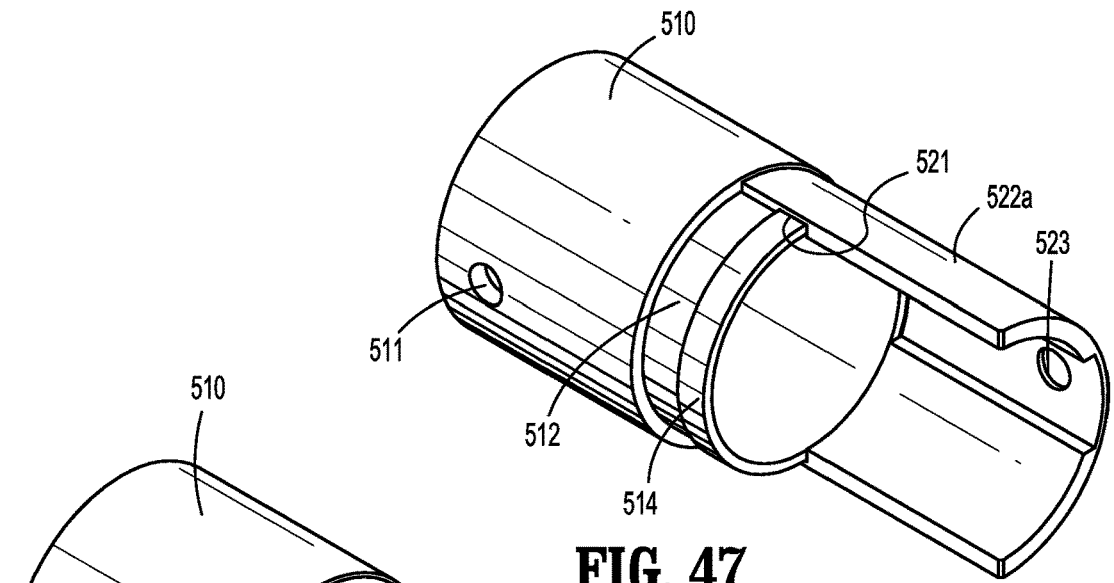
FIG. 47 is a perspective view of the connector assembly of FIG. 45 with a sleeve and first section of a tubular extension removed.
Figure 48:
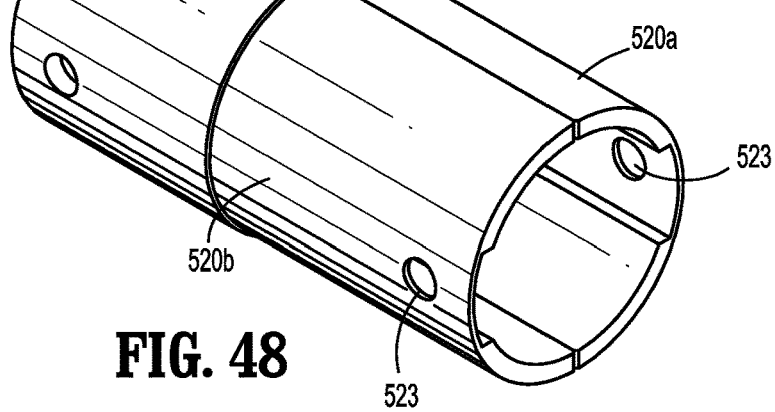
FIG. 48 is a perspective view of the connector assembly of FIG. 45 with the sleeve removed.
Figure 49:
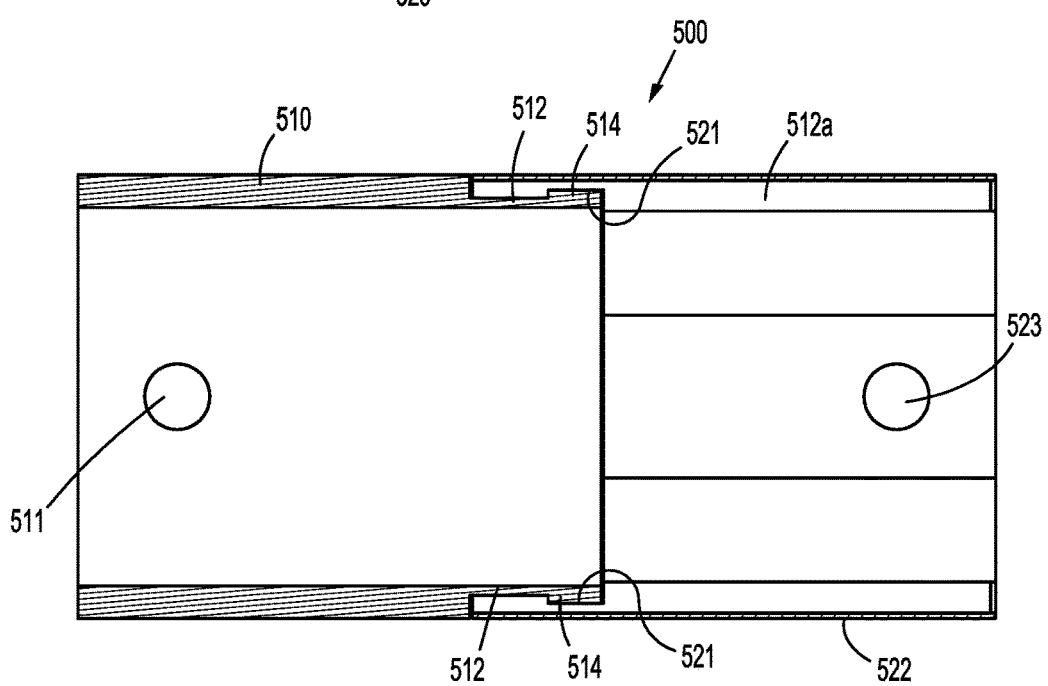
FIG. 49 is a cross-sectional side view taken along line 49-49 of FIG. 45.

With reference now to FIGS. 42-44, an adapter assembly according to another embodiment of the present disclosure is shown generally as adapter assembly 400. Adapter assembly 400 is substantially similar to adapter assemblies 100 and 300 described hereinabove, and therefore will only be described as relates to the differences therebetween.

Adapter assembly 400 includes a proximal portion 402 and a distal portion 404 rotatable along a longitudinal axis "X" relative to proximal portion 402. Distal portion 404 includes a support structure 408 secured to outer sleeve 405 and formed about first and second pusher assemblies 440, 450. Support structure 408 includes a plurality of reinforcing members 462 extending substantially the length of outer sleeve 405. Reinforcing members 462 each include a proximal tab 462a and a distal tab 462b which extend through outer sleeve 405 to secure reinforcing member 462 within outer sleeve 405. Proximal tabs 462 of reinforcing members 462 are further configured to engage a rotation knob 410 of adapter assembly 400. Adapter assembly 400 may include annular plates (not shown) positioned radially inward of reinforcing members 462 that maintain proximal and distal tabs 462a, 462b of reinforcing members 462 in engagement with outer sleeve 405. The annular plates may also provide structure support to distal portion 404 of adapter assembly 400.

With reference to FIGS. 45-49, a connection assembly according to an embodiment of the present disclosure is shown generally as connection assembly 500. As shown and will be described, connection assembly 500 is configured to be attached to first and second tubular bodies (not shown) for connecting the first tubular body, e.g., adapter assembly 100 (FIG. 3), 300 (FIG. 36), 400 (FIG. 42), to the second tubular body, e.g., extension assembly 200 (FIG. 17). It is envisioned, however, that the aspects of the present disclosure may be incorporated directly into the first and second tubular bodies to permit connection of the first tubular body directly to the second tubular body.

Connection assembly 500 includes a tubular base 510 and a tubular extension 520 formed of first and second sections 520a, 520b and an outer sleeve 522. As shown, tubular base 510 defines a pair of openings 511 for securing tubular base 510 to a first tubular body (not shown). Alternatively, tubular base 510 may include only a single opening, one or more tabs (not shown), and/or one or more slots (not shown), for securing tubular base 510 to the first tubular body (not shown). A flange 512 extends from a first end of tubular base 510 and includes an annular rim 514 extending thereabout.

First and second sections 520a, 520b of tubular extension 520 are substantially similar to one another and each define an annular groove 521 formed along an inner first surface thereof. Each of first and second section 520a, 520b of tubular extension 520 is configured to be received about flange 512 of tubular base 510 such that rim 514 of tubular base 510 is received within grooves 521 of first and second sections 520*a*, 520*b* of tubular extension 520. Once first and second sections 520*a*, 520*b* of tubular extension 520 are received about flange 512 of tubular base 510, outer sleeve 522 of tubular extension 520 is received about first and second sections 520*a*, 520*b* of tubular extension 520 to secure tubular extension 520 to tubular base 510.

As shown, each of first and second sections 520*a*, 520*b* of tubular extension 520 define an opening 523 configured to be aligned with a pair of openings 525 in outer sleeve 522 to secure outer sleeve 522 to first and second sections 520*a*, 520*b*. Either or both of first and second sections 520*a*, 520*b* and outer sleeve 522 may include one or more tabs, and/or one or more slots for securing outer sleeve 522 about first and second extensions. Alternatively, outer sleeve 522 may be secured to first and second sections 520*a*, 520*b* in any suitable manner.

Outer sleeve 522 may be selectively secured about first and second extensions for selective removal of outer sleeve 522 from about first and second sections 520*a*, 520*b* to permit separation of tubular extension 520 from tubular base 510. Alternatively, outer sleeve 522 may be permanently secured about first and second sections 520*a*, 520*b* to prevent tubular extension 520 from being separated from tubular base 510. As noted above, although tubular base 510 and tubular extension 520 are shown and described as forming an independent connection assembly 500, it is envisioned that tubular base 510 may be formed on a first tubular member, e.g., adapter assembly 100 (FIG. 3) and tubular extension 520 may be formed on a second tubular member, e.g., extension assembly 200 (FIG. 17) such that the first tubular member may be directly connected to the second tubular member.

Figure 50:
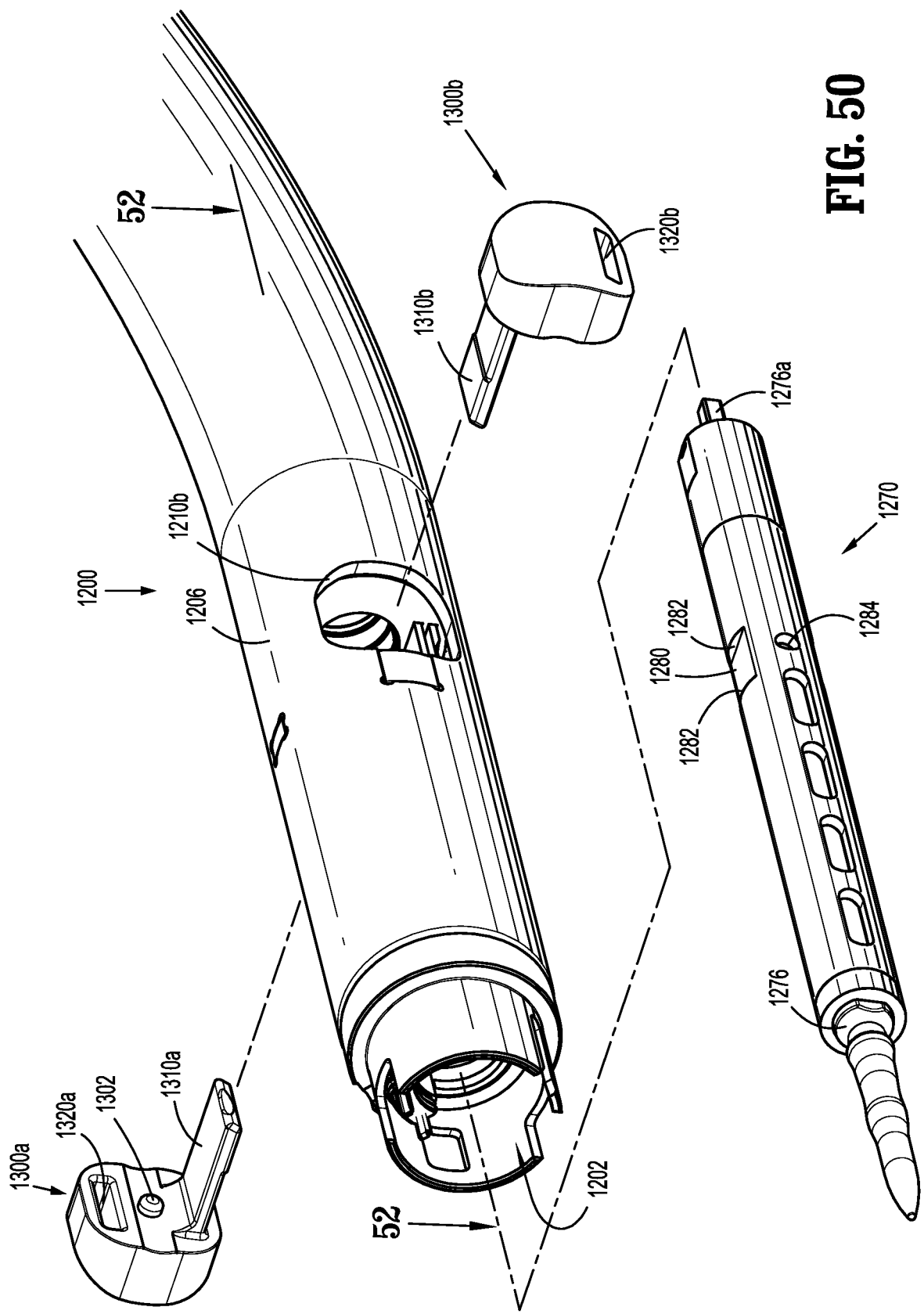
FIG. 50 is a perspective view, with parts separated, of a distal end of the adapter assembly of FIG. 1 in accordance with embodiments of the present disclosure.
Figure 51:
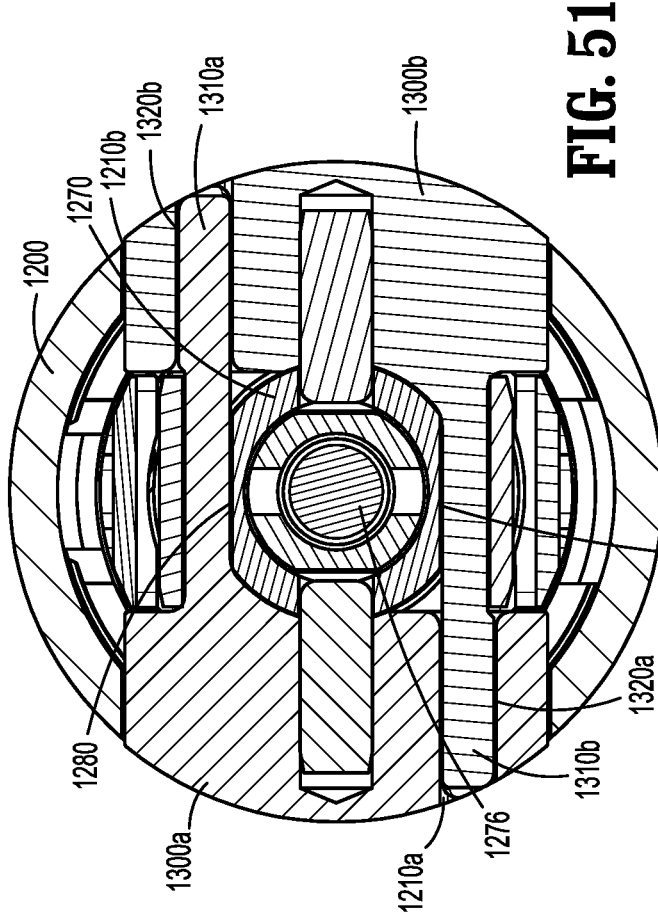
FIG. 51 is a transverse cross-sectional view of a portion of the distal end of the adapter assembly of FIG. 50.
Figure 52:
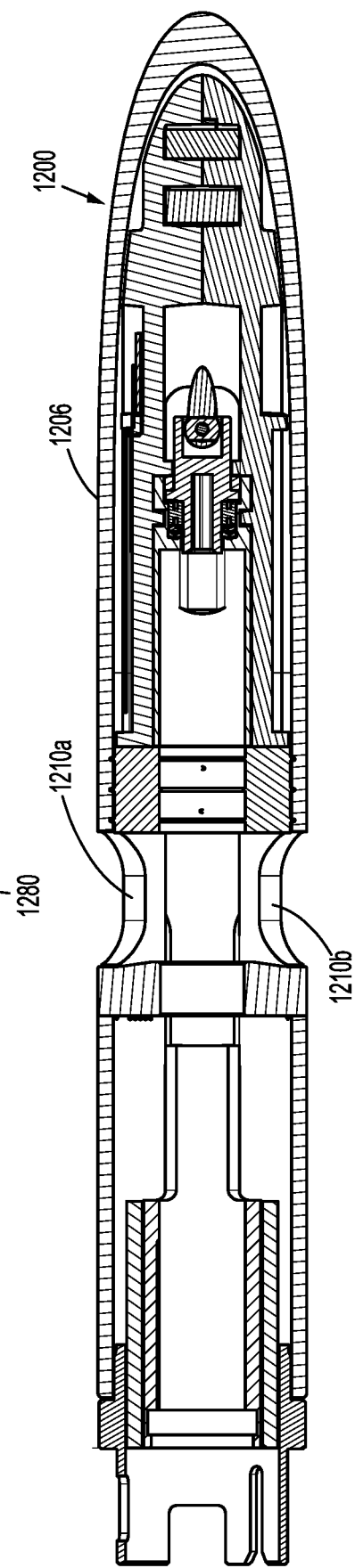
FIG. 52 is a longitudinal cross-sectional view of the distal end of the adapter assembly taken along line 52-52 of FIG. 50.

With reference to FIGS. 50-52, an alternate embodiment of a trocar assembly 1270 is shown in combination with an alternate embodiment of an extension assembly 1200. Trocar assembly 1270 is similar to trocar assembly 270 described above, and not all similarities will be discussed herein. However, while trocar assembly 270 is configured for secure engagement to link assembly 277 of extension assembly 200, trocar assembly 1270 is configured for releasable engagement with extension assembly 1200.

With particular reference to FIG. 50, trocar assembly 1270 includes a pair of flattened portions 1280 about its perimeter, and extension assembly 1200 includes a pair of openings 1210*a*, 1210*b* through its outer wall or sleeve 1206 (opening 1210*a* is not visible in FIG. 50). When trocar assembly 1270 is engaged with extension assembly 1200, flattened portions 1280 of trocar assembly 1270 are axially aligned with openings 1210*a*, 1210*b* of extension assembly 1200. In this position, a pair of retention members 1300*a*, 1300*b* is insertable through respective openings 1210*a*, 1210*b* and adjacent (e.g., in contact with) flattened portions 1280.

More particularly, each retention member 1300*a*, 1300*b* includes an extension portion 1310*a*, 1310*b* and a receptacle 1320*a*, 1320*b*, respectively. Each extension portion 1310*a*, 1310*b* is configured to releasably engage receptacle 1320*a*, 1320*b* of the opposite retention member 1300*a*, 1300*b*. That is, extension portion 1310*a* of retention member 1300*a* is configured to releasably engage receptacle 1320*b* of retention member 1300*b*; extension portion 1310*b* of retention member 1300*b* is configured to releasably engage receptacle 1320*a* of retention member 1300*a*. It is envisioned that extension portions 1310*a*, 1310*b* respectively engage receptacles 1320*b*, 1320*a* via a snap-fit connection. It is further envisioned that retention member 1300*a* is identical to retention member 1300*b*, which may be helpful to minimize manufacturing costs and to facilitate assembly.

In use, to engage trocar assembly 1270 with extension assembly 1200, trocar assembly 1270 is inserted through a distal opening 1202 of extension assembly 1200 until a proximal end 1276*a* of a drive screw 1276 of trocar assembly 1200 engages a link assembly of trocar assembly 1200 (see link assembly 277 of trocar assembly 270 in FIG. 32, for example). Next, extension portion 1310*a*, 1310*b* of each retention member 1300*a*, 1300*b*, respectively, is inserted through respective opening 1210*a*, 1210*b* of outer sleeve 1206, across flattened portion 1280 of trocar assembly 1270 and into receptacle 1320*b*, 1320*a* of the other retention member 1300*b*, 1300*a*, respectively. That is, extension portion 1310*a* of retention member 1300*a* is inserted through opening 1210*a* (or 1210*b*) of outer sleeve 1206, across flattened portion 1280 and into receptacle 1320*b* of retention member 1300*b*, and extension portion 1310*b* of retention member 1300*b* is inserted through opening 1210*b* (or 1210*a*) of outer sleeve 1206, across flattened portion 1280 and into receptacle 1320*a* of retention member 1300*a*. The engagement between extension portion 1310*a*, flattened portion 1280 and receptacle 1320*b*, and the engagement between extension portion 1310*b*, flattened portion 1280 and receptacle 1320*a* is configured to prevent longitudinal translation of a trocar member 1274 of trocar assembly 1270 with respect to outer sleeve 1206 of trocar assembly 1200 (e.g., due to the engagement between extension portions 1310*a*, 1310*b* and walls 1282 of flattened portion 1280). Additionally, the engagement between extension portion 1310*a*, flattened portion 1280 and receptacle 1320*b*, and the engagement between extension portion 1310*b*, flattened portion 1280 and receptacle 1320*a* is configured to prevent relative rotation between trocar member 1274 of trocar assembly 1270 and outer sleeve 1206 of trocar assembly 1200.

Additionally, and with particular reference to FIG. 50, each retention member 1300*a*, 1300*b* includes a nub 1302 (only nub 1302 associated with retention member 1300*a* is shown), which is configured to mechanically engage a detent 1284 of trocar assembly 1270. It is envisioned that the engagement between nubs 1302 and detents 1284 helps maintain the proper alignment and/or orientation between retention members 1300*a*, 1300*b* and trocar assembly 1270.

To disengage retention members 1300*a*, 1300*b* from each other, it is envisioned that a user can use a tool (e.g., a screwdriver-type tool) to push extension portions 1310*a*, 1310*b* out of receptacles 1320*b*, 1320*a*, respectively. It is also envisioned that retention members 1300*a*, 1300*b* are configured to be tool-lessly disengaged from each other and from trocar assembly 1270. Disengagement of retention members 1300*a*, 1300*b* allows trocar assembly 1270 to be removed from outer sleeve 1206 of trocar assembly 1200 (e.g., for replacement or cleaning). It is envisioned that cleaning can occur by inserting a cleaning device at least partially within at least one opening 1210*a*, 1210*b* of outer sleeve 1206 of extension assembly 1200, and directing a cleaning fluid (e.g., saline) proximally and/or distally to help flush out any contaminants that may be present within outer sleeve 1206, for example.

Additionally, while extension assembly 1200 and trocar assembly 1270 are shown used in connection with adapter assembly 100, the present disclosure also envisions the use of extension assembly 1200 and/or trocar assembly 1270 with a surgical instrument (e.g., a circular stapling instrument) without the use of an adapter assembly.

Figure 53:
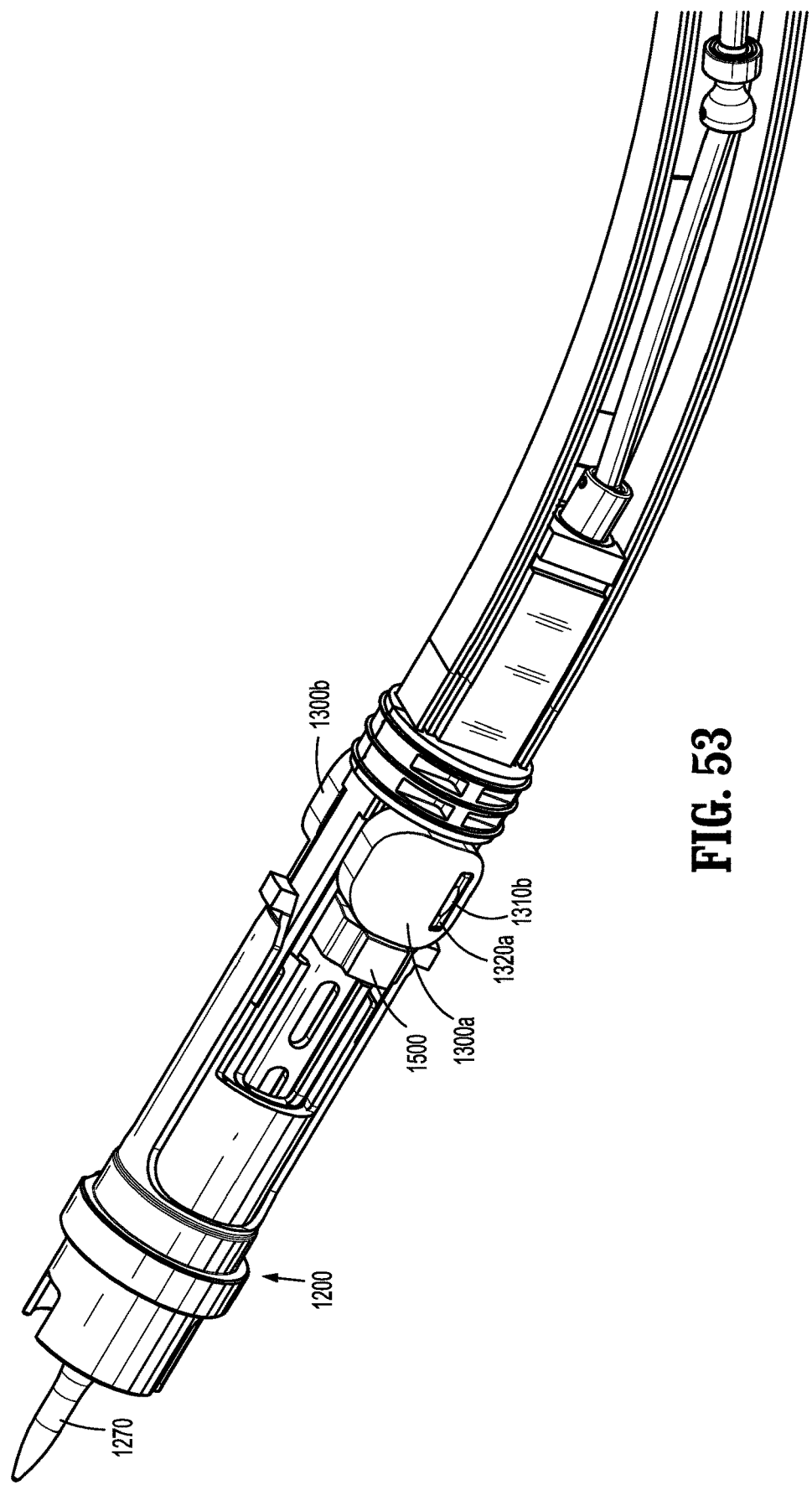

With reference to FIGS. 53-55, the present disclosure also includes a strain gauge 1500, a position sensor 1520, and a memory sensor 1540 (e.g., an E-PROM (erasable programmable read-only memory) sensor). With particular reference to FIG. 55, it is envisioned that a flexible cable 1600 extends between strain gauge 1500, position sensor 1520, memory sensor 1540 and a printed circuit board (not shown), and from the printed circuit board to an electrical connector disposed at proximal portion 302 of adapter assembly 300, for example.

It is envisioned that strain gauge 1500 is used to detect an axial load exerted on the tissue during clamping of tissue. Here, it is envisioned that if this load is too great, or exceeds a predetermined value, the user (or stapling device 10 itself) may abort the stapling operation or may choose to use a different stapling device 10 or adapter assembly 100, for example.

It is envisioned that position sensor 1520 is used to detect the axial position of the fasteners during the stapling process (e.g., when the fasteners are being ejected from adapter assembly 100). It is further envisioned that memory sensor 1540 is configured to recognize the size and/or type of staple cartridge that is engaged with adapter assembly 100 that is engaged with stapling device 10 and to relay this information to handle housing 12 of stapling device 10.

Referring now to FIGS. 56-62, a seal assembly 1700 for use with surgical device 10, adapter assembly 100, and/or extension assembly 200 of the present disclosure is shown. Seal assembly 1700 is configured to facilitate thoroughly cleaning debris (e.g., surgical debris) from surgical device 10 following use, prior to use, and/or prior to reuse, for instance. More specifically, seal assembly 1700 is particularly useful when internal portions of surgical device 10 are flushed with a fluid to help remove debris from within surgical device 10. Further, seal assembly 1700 is configured to minimize flow traps which may occur when a flushing introduction point is located distally of a seal or seal assembly, for instance. Additionally, while seal assembly 1700 is shown and described for use a particular type of surgical device 10, seal assembly 1700 is usable with various types of surgical instruments (e.g., reusable) where cleaning and/or sterilization may be desired. Further, when used with surgical device 10 of the present disclosure, seal assembly 1700 replaces proximal seal member 262, and first and second distal seal members 264, 266 (FIGS. 27 and 28).

Figure 56:
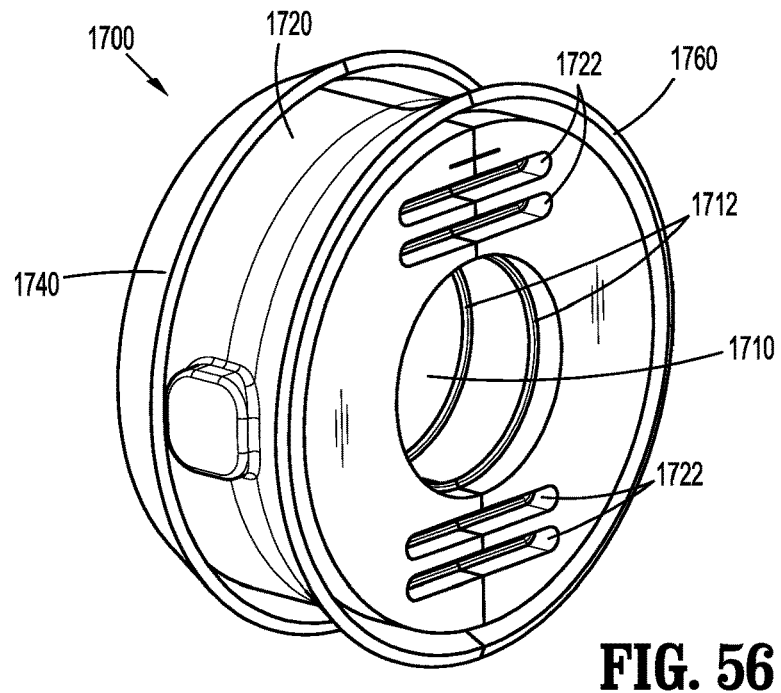
FIG. 56 is a perspective view of a seal assembly for use with the frame assembly of FIG. 20.
Figure 57:
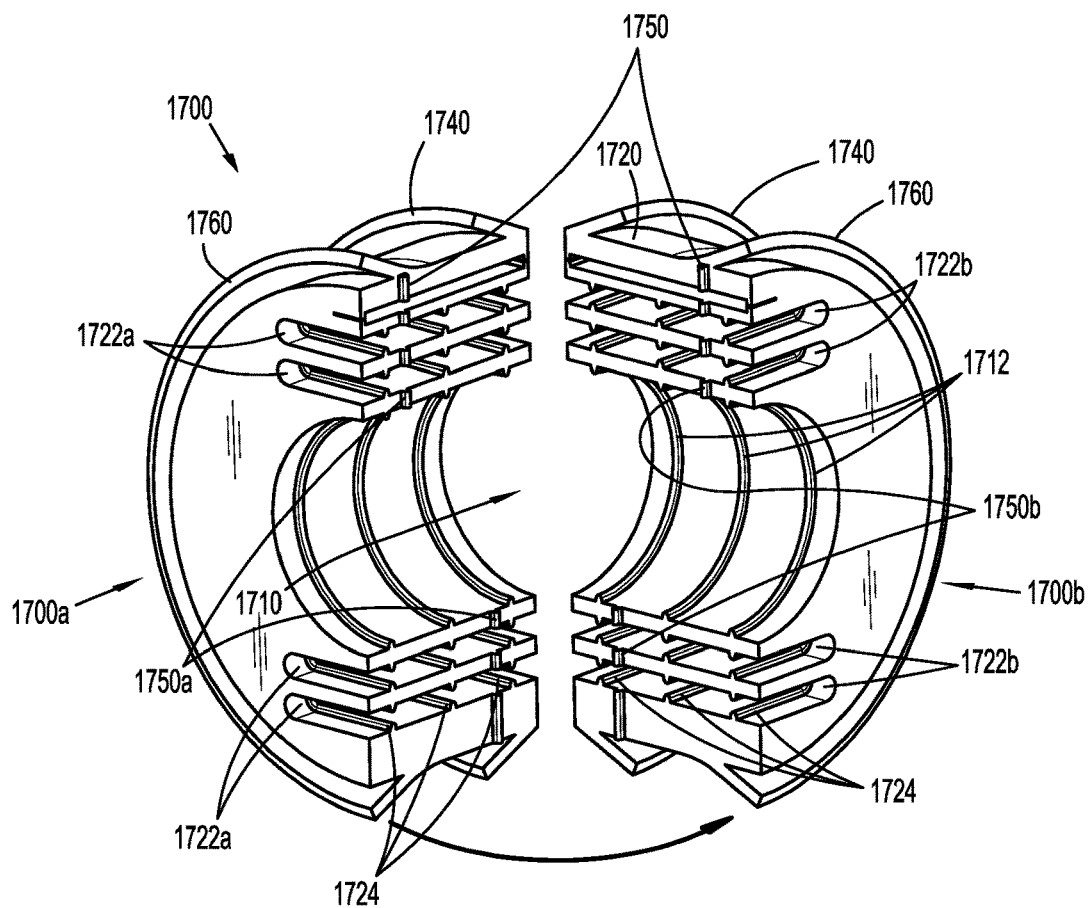
FIG. 57 is an assembly view of the seal assembly of FIG. 56.

Seal assembly 1700 is positioned within outer sleeve 206 and defines an aperture 1710 through which an actuation member, e.g., drive screw 276, is positioned. With particular reference to FIGS. 56 and 57, seal assembly 1700 is formed of a first portion 1700a and a second portion 1700b, which are configured to engage each other (e.g., frictionally held together by an inner wall 206c of outer sleeve 206). It is envisioned that first portion 1700a is a mirror image or a substantial mirror image of second portion 1700b.

Figure 62:
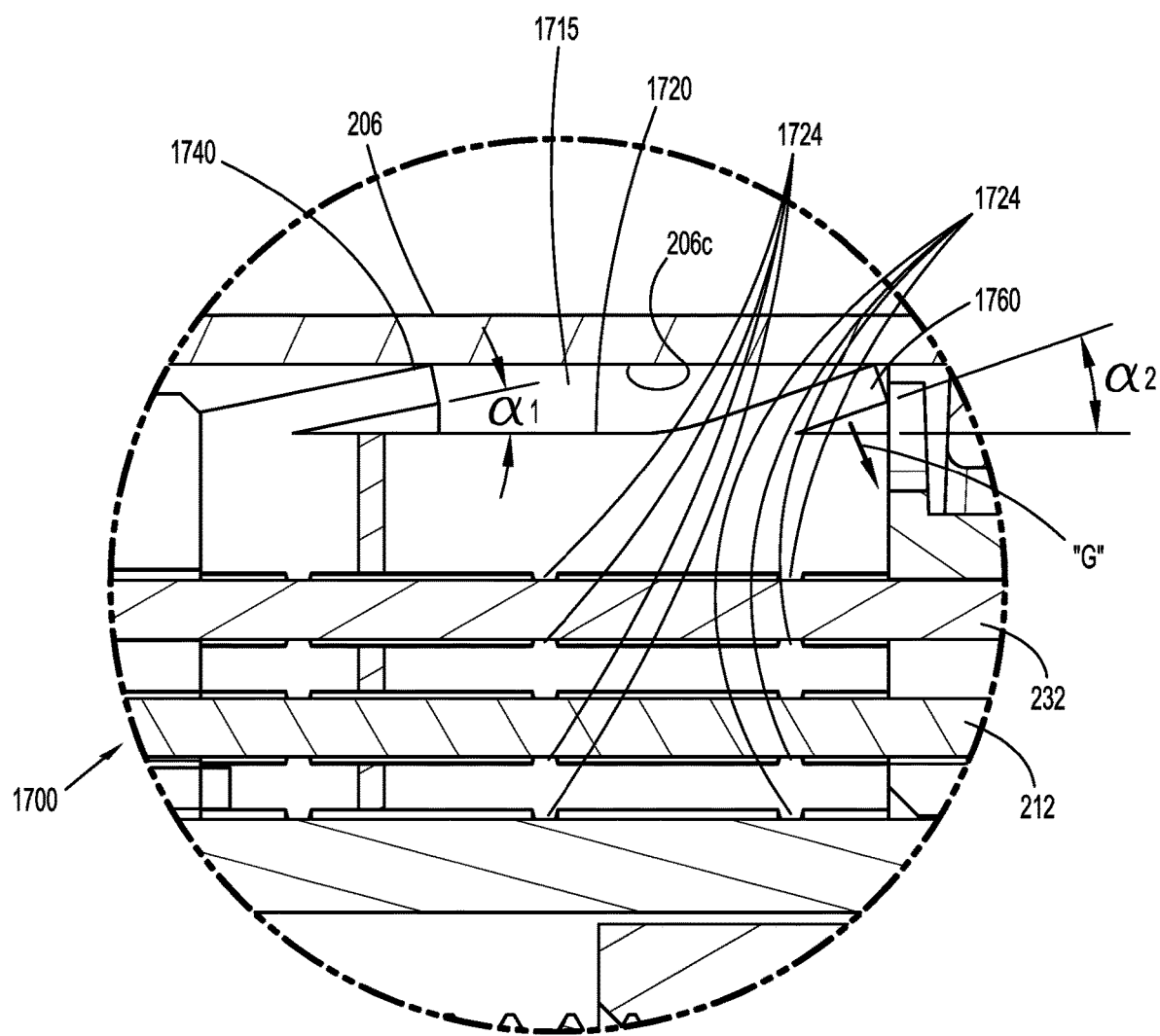
FIG. 62 is an enlarged view of the indicated area of detail of FIG. 61.

With continued reference to FIGS. 56, 57 and 62, seal assembly 1700 includes an annular body portion 1720, an annular proximal seal 1740 (e.g., a wiper seal), and an annular distal seal (e.g., a wiper seal) 1760. As shown, proximal seal 1740 and distal seal 1760 extend radially outward from body portion 1720, and define acute angles α1 and α2 (see FIG. 62), respectively, with respect to body portion 1720. Angles α1 and α2 may be the same or different from each other, and may be from about 15° to about 45°, for example. Additionally, as shown in FIG. 62, proximal seal 1740 and distal seal 1760 are configured to contact inner wall 206c of outer sleeve 206 of surgical device 10.

Body portion 1720 of seal assembly 1700 includes a plurality of channels 1722 formed therein. Channels 1722 are configured to allow inner flexible band assembly 210 (including first and second inner flexible bands 212, 214) and outer flexible band assembly 230 (including first and second flexible bands 232, 234) to pass therethrough (see FIG. 20). More particularly, and as shown in FIG. 57, each of first portion 1700a of seal assembly 1700 and second portion 1700b include openings 1722a, 1722b (e.g., U-shaped), respectively. When first portion 1700a and second portion 1700b engage each other, openings 1722a, 1722b form channels 1722 (FIG. 56). Accordingly, during assembly of surgical device 10, for instance, seal assembly 1700 is positionable to surround inner flexible band assembly 210 and outer flexible band assembly 230 without the need to thread inner flexible band assembly 210 and outer flexible band assembly 230 through channels 1722. Additionally, while four channels 1722 are shown, seal assembly 1700 may include more or fewer than four channels 1722 depending on the number of bands (or other features) extending therethrough.

Referring now to FIGS. 57 and 62, seal assembly 1700 also includes a plurality of channel seals 1724 associated with each channel 1722. In the illustrated embodiment, each channel 1722 includes three longitudinally-spaced channel seals 1724 extending along the periphery of channel 1722. Channel seals 1724 (e.g., rubber gaskets) are configured to provide a seal (e.g., a water-tight seal) between walls of seal assembly 1700 defining channels 1722 and bands 212, 214, 232, 234 extending therethrough. Seal assembly 1700 may include more or fewer than three channel seals 1724 per channel 1722.

With reference to FIGS. 56 and 57, seal assembly 1700 includes a plurality of aperture seals 1712 associated with aperture 1710. In the illustrated embodiment, aperture 1710 includes three longitudinally-spaced aperture seals 1712 extending along the periphery of aperture 1710. Aperture seals 1712 (e.g., rubber gaskets) are configured to provide a seal (e.g., a water-tight seal) between walls of seal assembly 1700 defining aperture 1710 and a component (or components) of surgical device 10 extending therethrough. Seal assembly 1700 may include more or fewer than three aperture seals 1712.

FIG. 57 also illustrates a plurality of portion seals 1750. A plurality of first portion seals 1750a is disposed on first portion 1700a of seal assembly 1700, and a plurality of second portion seals 1750b is disposed on second portion 1700b of seal assembly 1700. When first portion 1700a of seal assembly 1700 is engaged with second portion 1700b of seal assembly 1700, first portion seals 1750a engage or otherwise contact (e.g., compress) corresponding second portion seals 1750b, thereby creating a seal (e.g., a water-tight seal) therebetween. As shown, a first set of portion seals 1750 is disposed on a proximal part of first portion 1700a and second portion 1700b, and a second set of portion seals 1750 is disposed on a distal part of first portion 1700a and second portion 1700b.

The use of aperture seals 1712, channel seals 1724, and portion seals 1750 helps prevent contaminants from entering portions of surgical device 10 that are located proximal of seal assembly 1700.

Figure 58:
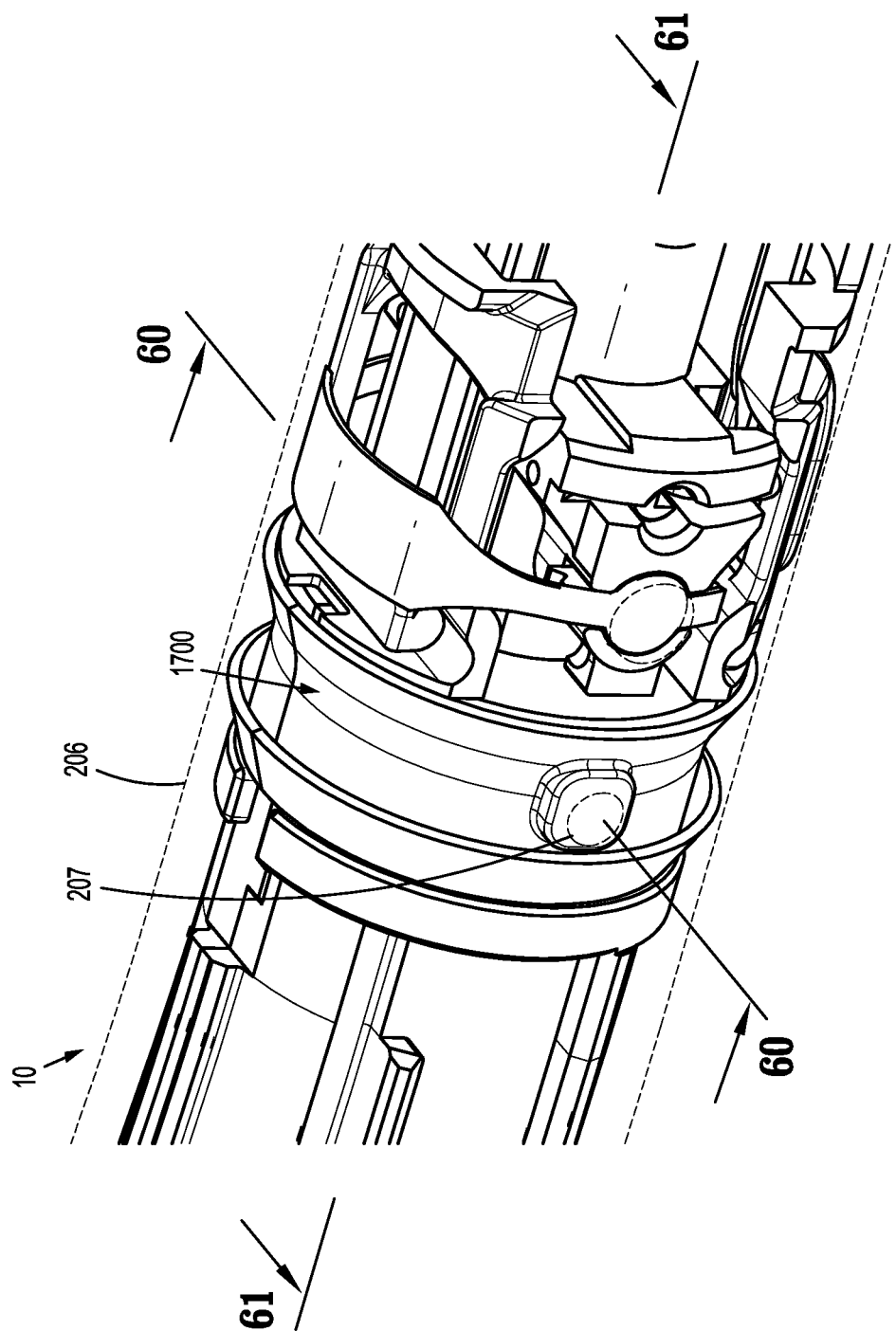
FIG. 58 is a perspective view of the seal assembly of FIGS. 56 and 57 shown within the frame assembly of FIG. 20.
Figure 59:
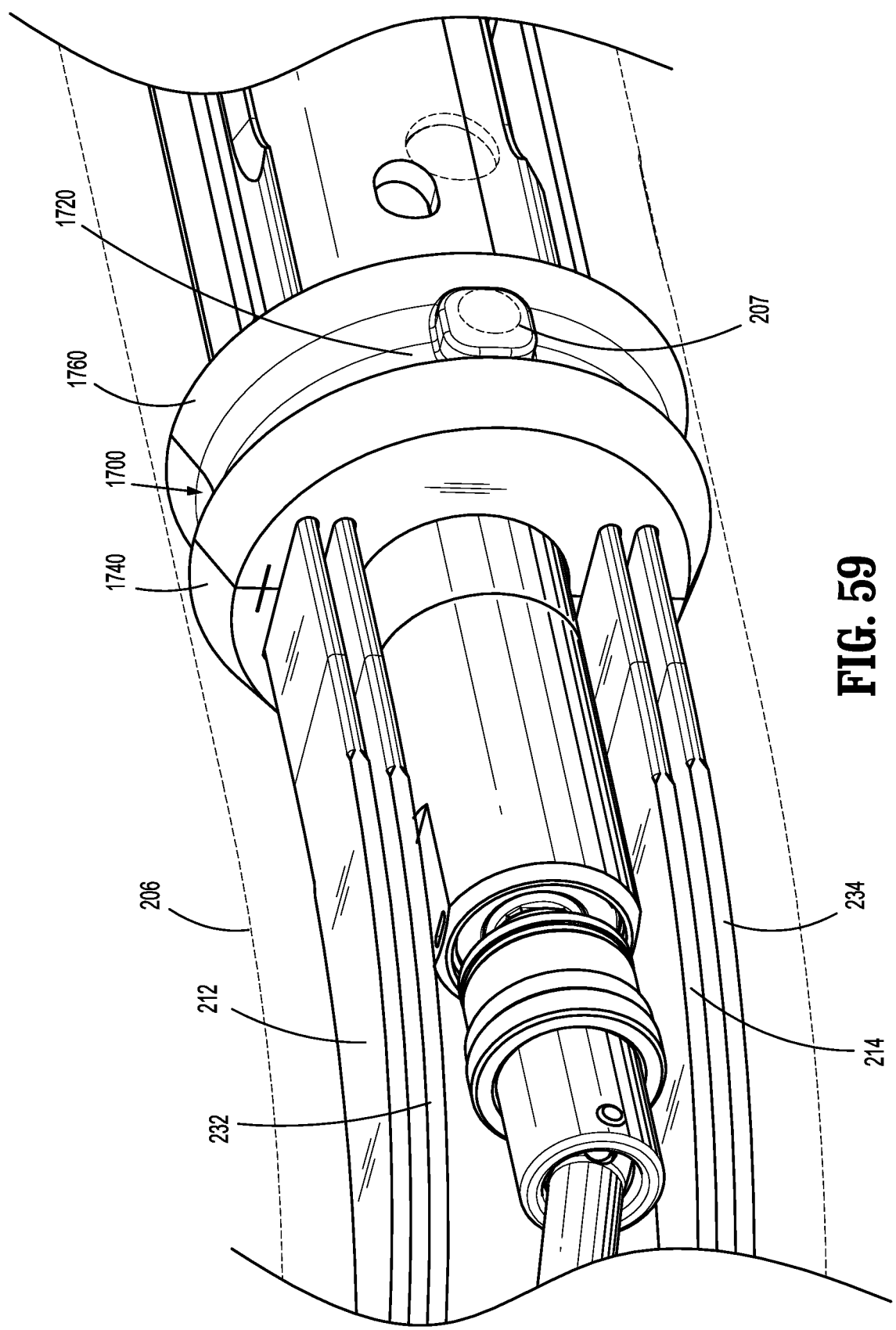
FIG. 59 is a perspective view of the seal assembly of FIGS. 56 and 57 shown within the frame assembly of FIG. 20 and with portions of the frame assembly omitted.
Figure 60:
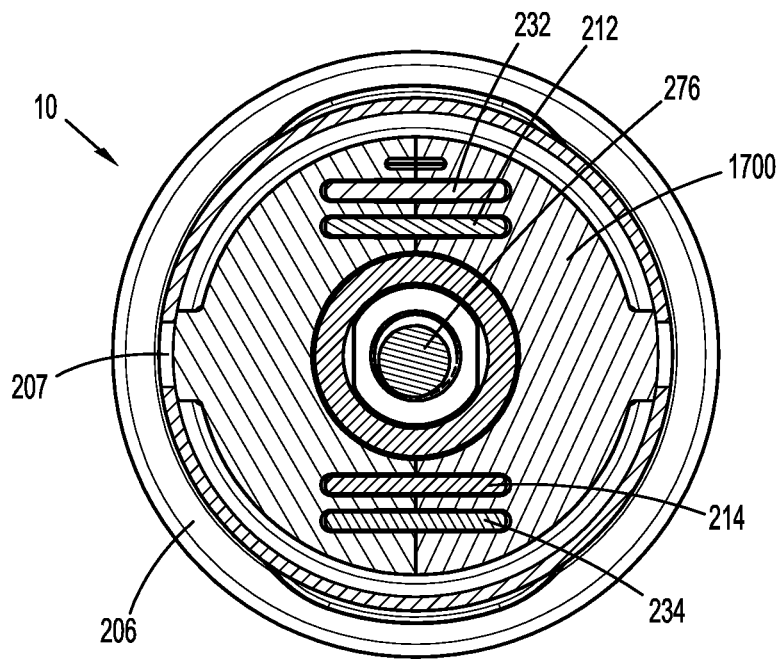
FIG. 60 is a transverse cross-sectional view taken along line 60-60 of FIG. 58.
Figure 61:
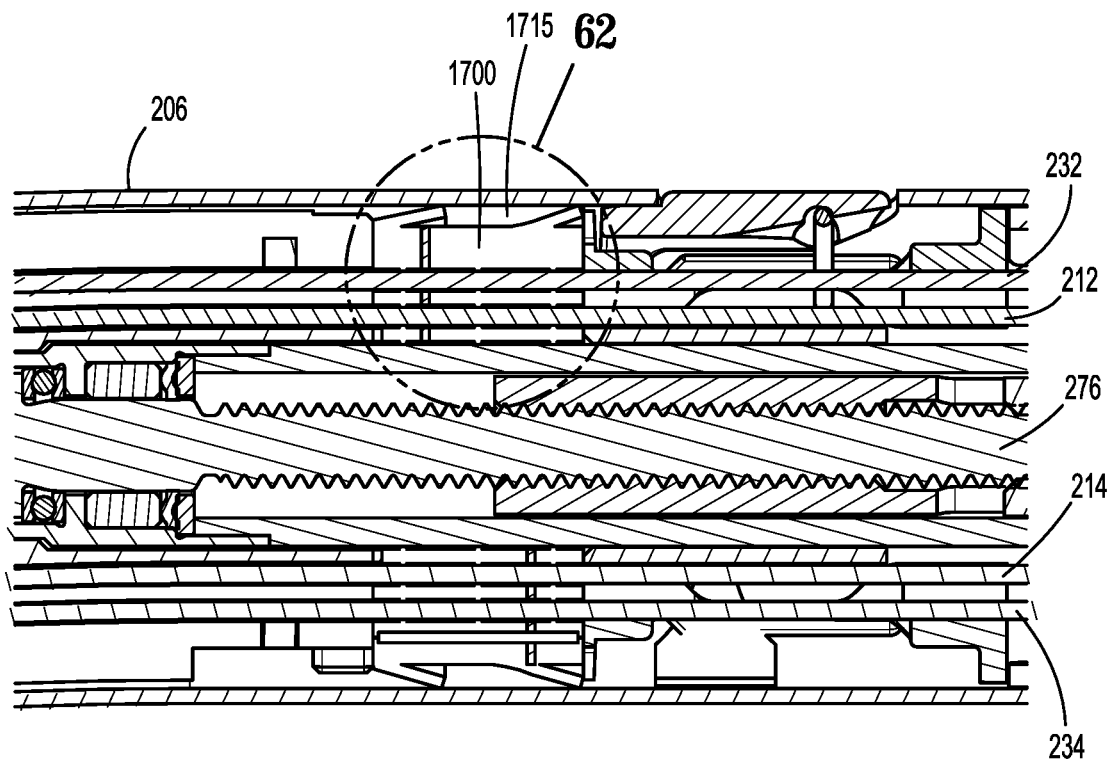
FIG. 61 is a longitudinal cross-sectional view taken along line 61-61 of FIG. 58.

Seal assembly 1700 is positioned within outer sleeve 206 of surgical device 10 such that an opening or port 207 extending through outer sleeve 206 is positioned adjacent an annular space 1715 between proximal seal 1740 and distal seal 1760 of seal assembly 1700, as shown in FIGS. 58 and 59. Additionally, seal assembly 1700 is positioned such that each band 212, 214, 232, 234 of surgical device 10 extends through one channel 1722 of seal assembly 1700, as noted above.

To clean portions of surgical device (e.g., portions located distally of seal assembly 1700), a fluid (e.g., water, saline, etc.; or a gas) is introduced through port 207 of outer sleeve 206 into annular space 1715 of seal assembly 1700. With particular reference to FIG. 62, as fluid fills annular space 1715, proximal seal 1740 prevents the fluid from moving proximally therepast due to the angle αl proximal seal 1740 makes with body portion 1720 of seal assembly 1700, and due to the interference (or contact) proximal seal 1740 makes with inner wall 206c of outer sleeve 206. Further, as the fluid pressure builds, the proximally-directed pressure causes proximal seal 1740 to be further forced against inner wall 206c of outer sleeve 206, thereby increasing the effectiveness of the seal.

With continued reference to FIG. 62, as fluid fills annular space 1715, the fluid pressure builds until distal seal 1760 is displaced away from inner wall 206c of outer sleeve 206 in the general direction of arrow "G." This displacement of distal seal 1760 away from inner wall 206c of outer sleeve 206 allows the pressurized fluid from annular space 1715 to sluice or flow between distal seal 1760 and inner wall 206c of outer sleeve 206, distally of seal assembly 1700, and through portions of extension assembly 200 and adapter assembly 100, for instance, thereby flushing these portions of surgical device 10 to remove surgical debris, for example. Since the fluid is introduced proximally of a distal end of seal assembly 1700, flow traps (which may otherwise occur between a fluid port and a seal disposed proximally thereof) are eliminated or minimized.

The present disclosure also includes methods of cleaning a surgical instrument (e.g., surgical device 10) utilizing seal assembly 1700. For instance, disclosed methods include inserting fluid through port 207 of outer sleeve 206 or an outer tube of surgical device 10 and into annular space 1715 between proximal seal 1740 and distal seal 1760, filling annular space 1715 with the fluid, deflecting distal seal 1760 away from its contact with outer sleeve 206 (in response to the pressure build-up of the fluid), and moving the fluid from annular space 1715 distally beyond distal seal 1760 of seal assembly 1700. The method also includes removing the fluid from a distal end of surgical device 10.

Figure 63:
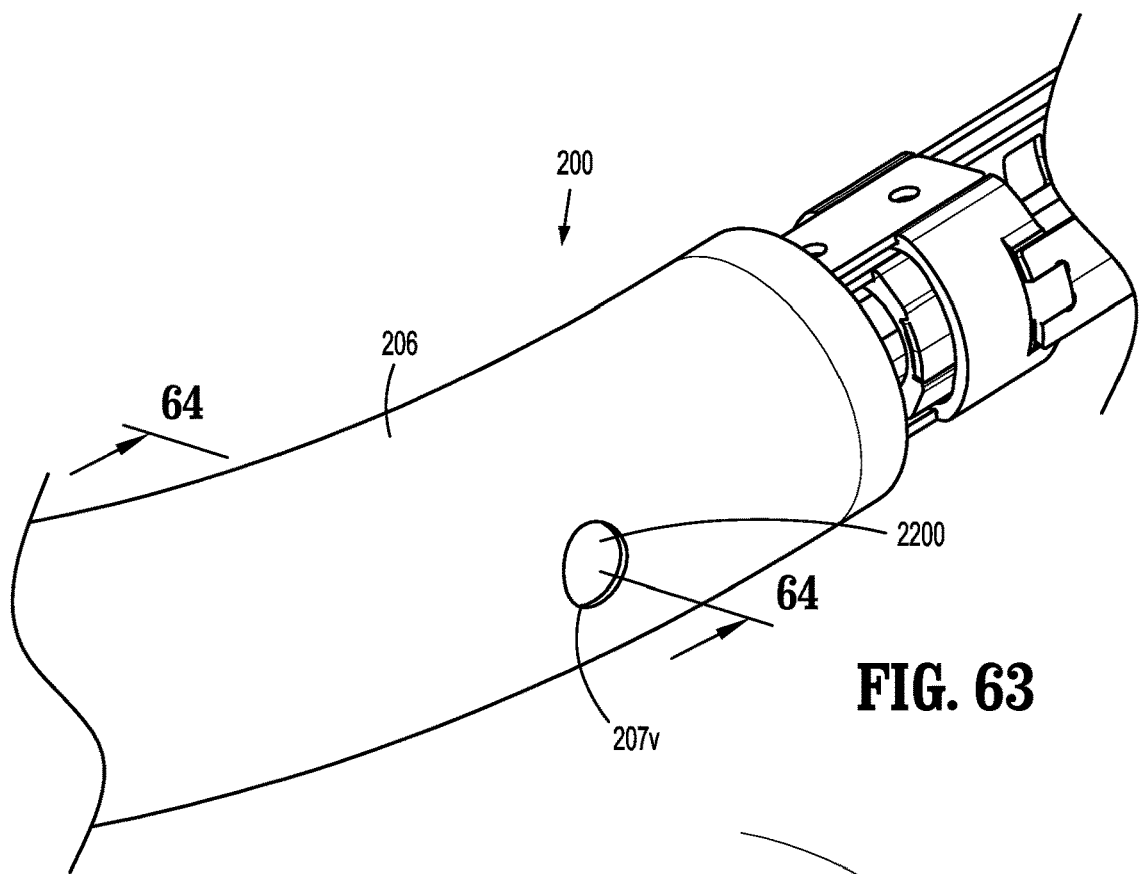
FIG. 63 is a perspective view of a portion of a surgical device including a valve in accordance with an embodiment of the present disclosure.
Figure 64:
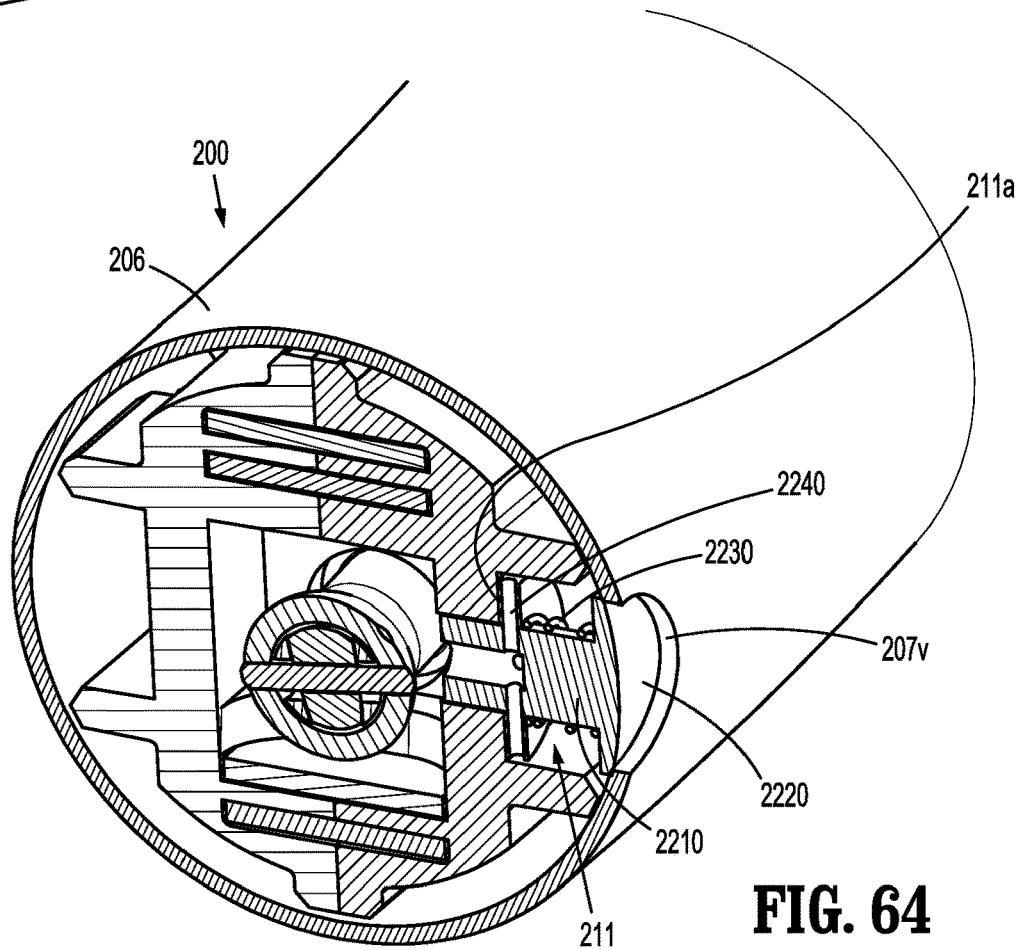
FIG. 64 is a transverse cross-sectional view of the surgical device taken along line 64 of FIG. 63.
Figure 65:
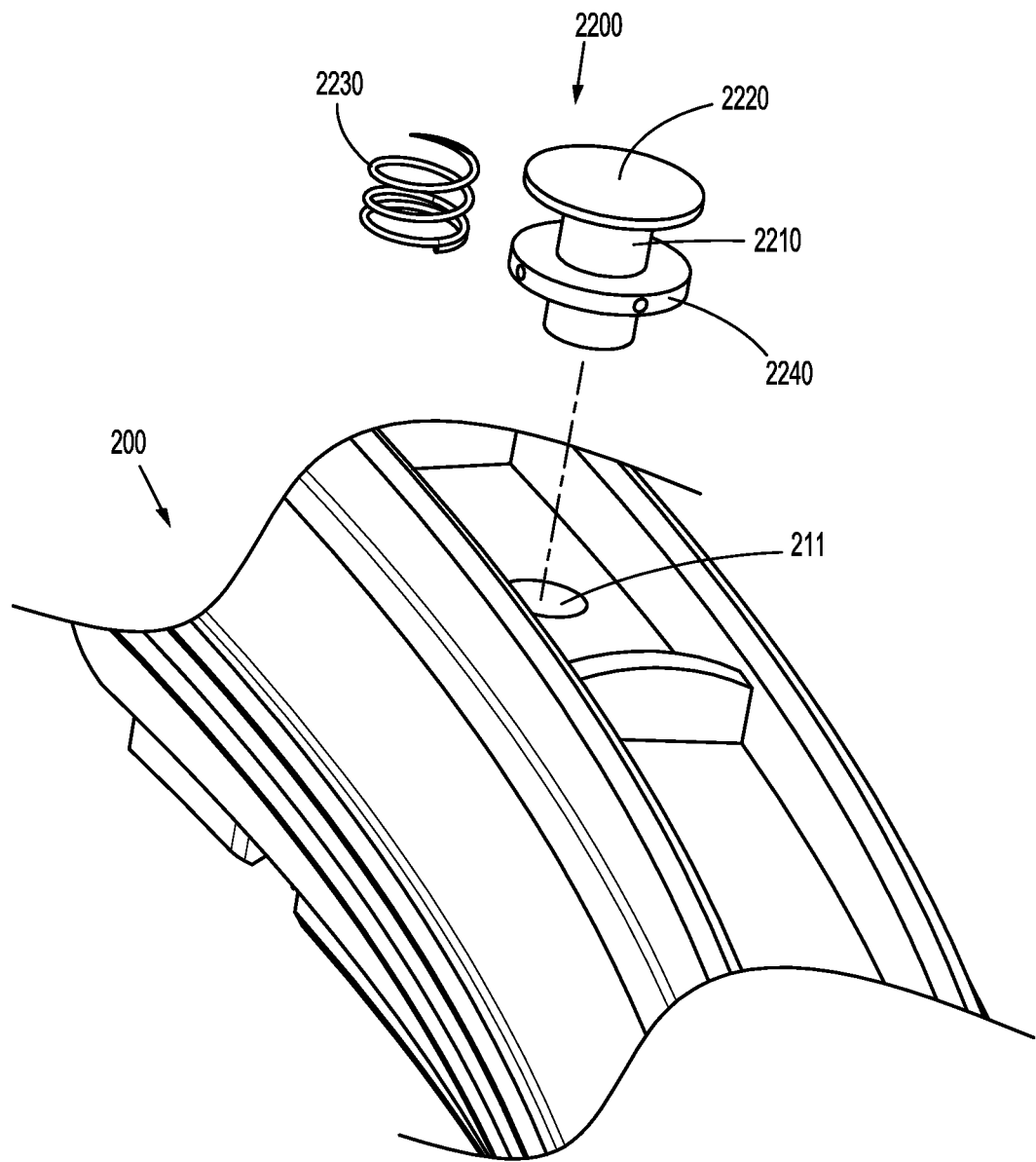
FIG. 65 is an assembly view of the valve of FIGS. 63 and 64.

Referring now to FIGS. 63-65, a valve 2200 for use with surgical device 10, adapter assembly 100, and/or extension assembly 200 of the present disclosure is shown. Valve 2200 is configured to selectively engage a first opening or port 207v extending through outer sleeve 206 of extension assembly 200 for selectively allowing air and/or fluid to pass through port 207v during cleaning, drying or venting of surgical device 10, for example.

Valve 2200 includes a body portion 2210, an engagement portion 2220, a biasing element 2230, and a shoulder 2240. Valve 2200 is disposed in a housing 211 within outer sleeve 206 and adjacent port 207v. Biasing element 2230 urges engagement portion 2220 toward and into contact with and/or through port 207v. In the illustrated embodiment, biasing element 2230 is a compression spring positioned about body portion 2210, and between engagement portion 2220 and shoulder 2240, and is configured to urge engagement portion 2220 away from shoulder 2240. Shoulder 2240 is positioned adjacent a wall 211a of housing 211. Other types of biasing elements are also contemplated by the present disclosure. It is also envisioned that engagement portion 2220 is movable into and out of engagement with port 207v without a biasing element, but with another mechanical actuator, for instance.

More particularly, engagement portion 2220 of valve 2200 is movable between an occluding position where engagement portion 2220 of valve 2200 is engaged with port 207v and an open position where at least a portion of engagement portion 2220 of valve 2200 is spaced radially inward from port 207v. Engagement portion 2220 of valve 2200 is biased radially outwardly in the occluding position. Either a mechanical device, or a user's finger, for example, can move engagement portion 2220 of valve 2200 radially inwardly from the occluding position to the open position. In the occluding position, engagement portion 2220 of valve 2200 provides a fluid-tight seal with port 207v, which prevents fluid from entering or exiting outer sleeve 206 through port 207v. When valve 2200 is in the open position, fluid and/or air are able to enter and exit outer sleeve 206 through the space between engagement portion 2220 and port 207v (e.g., walls defining port 207v).

When valve 2200 is in its rest position, when no extraneous forces are acting on valve 2200, engagement portion 2220 of valve 2200 is in the occluding position such that engagement portion 2220 is in mechanical engagement with and occluding (e.g., plugging or blocking) port 207v of outer sleeve 206.

When surgical device 10 is used to perform a surgical task, engagement portion 2220 of valve 220 is in its biased, occluding position. In this position, bodily fluid and gas is prevented or hindered from entering surgical device 10 through port 207v.

When cleaning debris from surgical device 10 (e.g., after a surgical procedure) is desired, a user can introduce fluid through a port of surgical device 10. During such a cleaning process, engagement portion 2220 of valve 2200 may either be in its occluding position or in its open position. It may be desirable to have engagement portion 2220 of valve 2200 in its occluding position during cleaning when a user desires to insert cleaning fluid into outer sleeve 206 through a different port (other than port 207v), for example. It may be desirable to have engagement portion 2220 of valve 2200 in its open position during cleaning when a user desires to insert cleaning fluid into outer sleeve 206 through port 207v. Additionally, it may be desirable to have engagement portion 2220 of valve 2200 in its open position during cleaning when port 207v is used as an air valve to facilitate the flow of fluid or gas through surgical device 10 when fluid or gas enters surgical device through a different port.

Additionally, when the cleaning of surgical device 10 is performed by introducing fluid through port 207v, engagement between a syringe (or the fluid exiting the syringe) and engagement portion 2220 of valve 2200 may cause engagement portion 2220 to move from its occluding position to its open position to allow fluid to enter surgical device 10 through port 207v.

Further, it may also be helpful to have engagement portion 2220 of valve 2200 in the open position to help dry out surgical device 10 after surgical device 10 has been used and/or cleaned. That is, when engagement portion 2220 of valve 2200 in the open position, air (e.g., ambient air, forced heated air, forced cooled air, or forced ambient air) is able to freely enter and exit surgical device 10 through port 207v to assist drying internal components of surgical device 10 which may include residual moisture, for example.

Additionally, while valve 2200 and port 207v are shown in a particular location on surgical device 10 (e.g., distally of seal assembly 1700; FIGS. 56-62), other locations of valve 2200 and port 207v are contemplated by the present disclosure. Further, surgical device 10 may include more than one valve 2200, and more than one associated port 207v. For instance, multiple valves 2200 and ports 207v can be used to create a particular path for fluid and air to flow to facilitate cleaning and drying surgical device 10.

In other embodiments, outer sleeve 206 of surgical device 10 is able to be at least partially disassembled from the remainder of surgical device 10 (e.g., via a threaded connection) to help facilitate drying out moisture from within surgical device 10.

Additionally, while valve 2200 is shown and described for use with a particular type of surgical device 10, valve 2200 is usable with various types of surgical instruments (e.g., reusable) where cleaning and/or sterilization may be desired.

The present disclosure also includes methods of cleaning a surgical instrument (e.g., surgical device 10) utilizing valve 2200. For instance, disclosed methods include inserting fluid through port 207c or a different port, and moving engagement portion 2220 of valve 2200 from its occluding position to its open position to allow air to enter surgical device 10 to facilitate drying internal components of surgical device 10.

Figure 66:
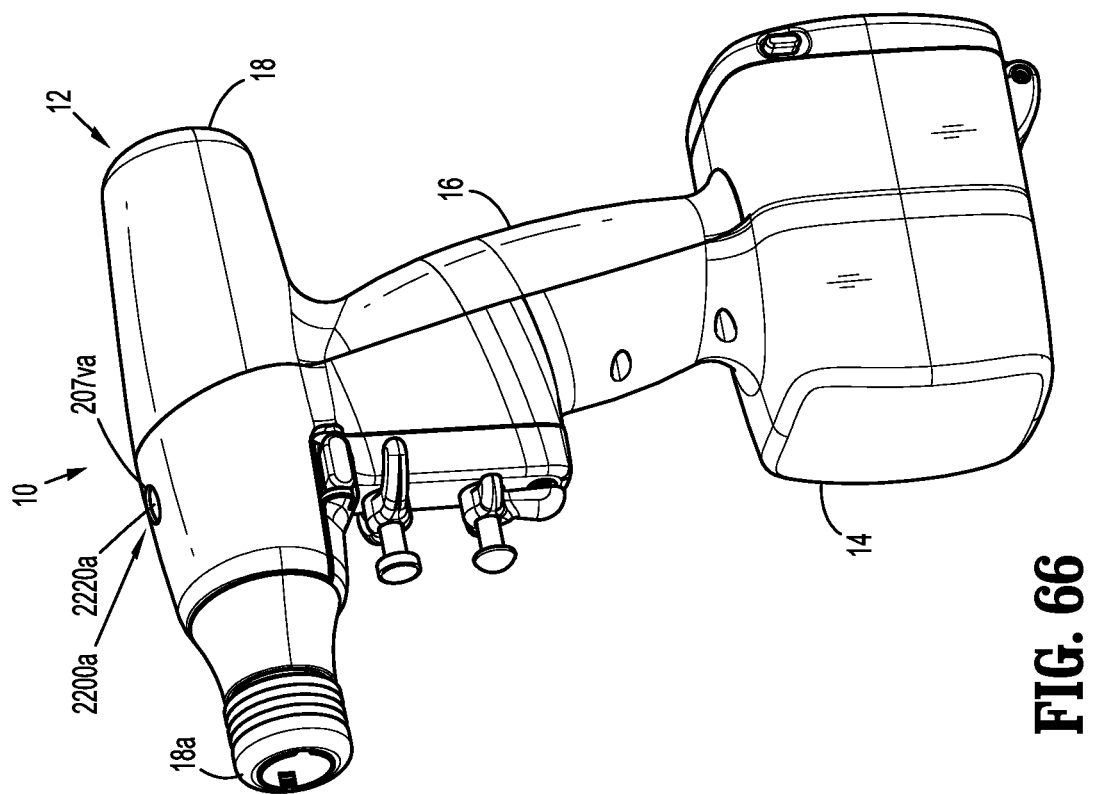
FIG. 66 is a perspective side view of a handle housing of a surgical device including a vent in accordance with an embodiment of the present disclosure.

Further, with reference to FIG. 66, surgical device 10 includes a valve 2200a and an associated port 207va disposed on a proximal portion of surgical device 10. In the illustrated embodiment, valve 2200a is located on handle housing 12. As discussed above with regard to valve 2200, valve 2200a is configured to selectively engage port 207va extending through handle housing 12 for selectively allowing air and/or fluid to pass through port 207va during cleaning, drying or venting of surgical device 10, for example.

Valve 2200a may be the same or similar to valve 2200 discussed above. For instance, an engagement portion 2220a of valve 2200a may be movable into and out of engagement with port 207va with a biasing element, without a biasing element, or with another mechanical actuator, for example.

Additionally, while valve 2200a and port 207va are shown in a particular location on handle housing 12, other locations of valve 2200a and port 207va are contemplated by the present disclosure. For instance, valve 2200a and port 207va may be located farther proximally or distally on handle housing 12 than the particular position shown in FIG. 66. Further, surgical device 10 may include more than one valve 2200a, and more than one associated port 207va. For instance, multiple valves 2200a and ports 207va can be included on handle housing 12 to create a particular path for fluid and air to flow to facilitate cleaning and drying surgical device 10.

Additionally, while valves 2200, 2200a are shown and described for use with a particular type of surgical device 10, valves 2200, 2200a are usable with various types of surgical instruments (e.g., reusable) where cleaning and/or sterilization may be desired.

The present disclosure also includes methods of cleaning a surgical instrument (e.g., surgical device 10) utilizing valve 2200, 2200a. For instance, disclosed methods include inserting fluid through port 207c or a different port, and moving respective engagement portions 2220, 2220a of valves 2200, 2200a from the occluding position to the open position to allow air to enter surgical device 10 to facilitate drying internal components of surgical device 10.

Referring now to FIGS. 67-70, various tools are disclosed for opening valves 2200, 2200a (see FIGS. 63-66) of surgical device 10. As discussed above, valves 2200, 2200a are configured to selectively allow air and/or fluid to pass through respective ports 207v, 207va during cleaning, drying or venting of surgical device 10, for example.

Figure 67:
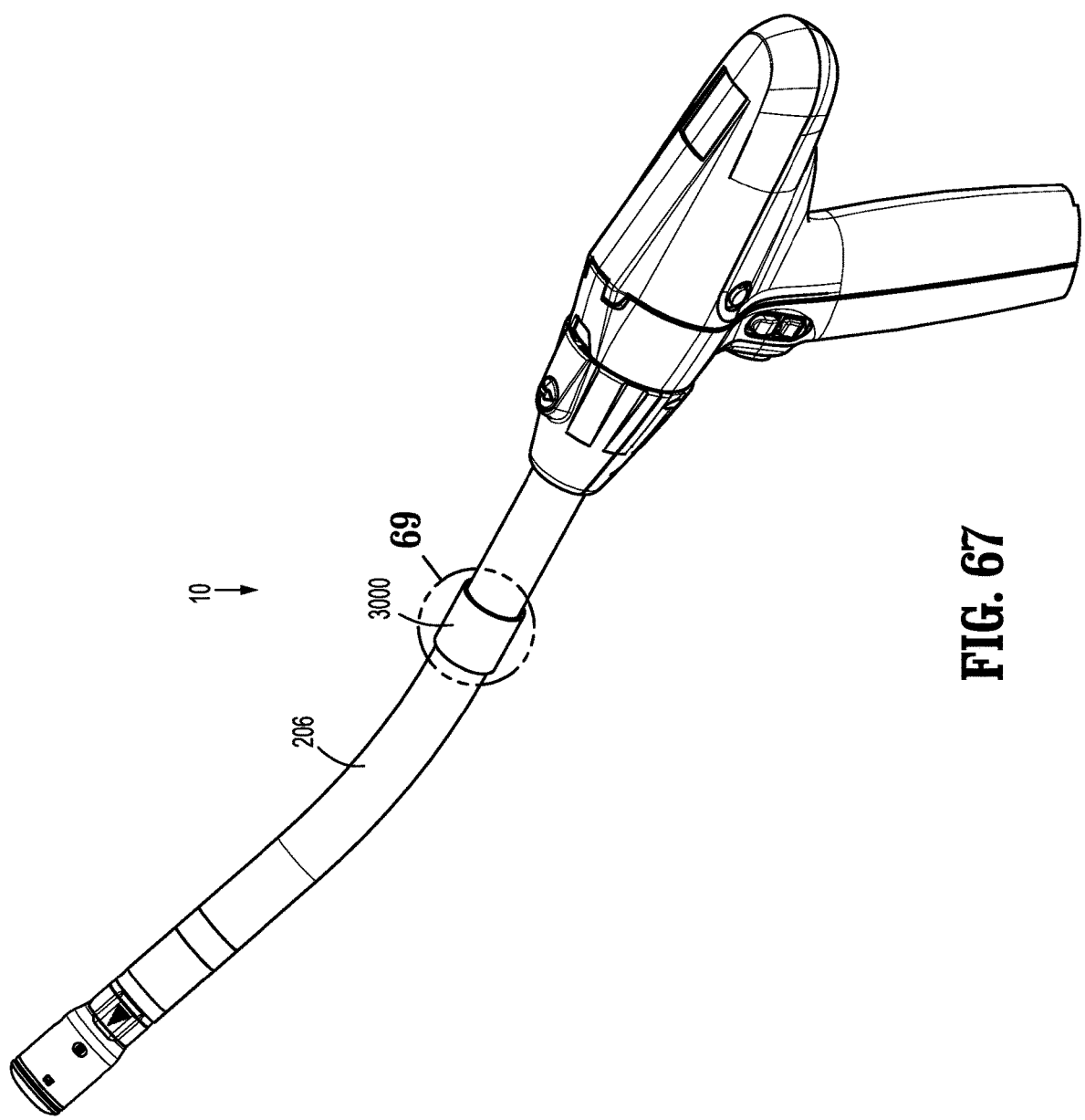
FIG. 67 is a perspective view of a surgical device including a valve, and an actuator engaged with a portion of the surgical device.
Figure 68:
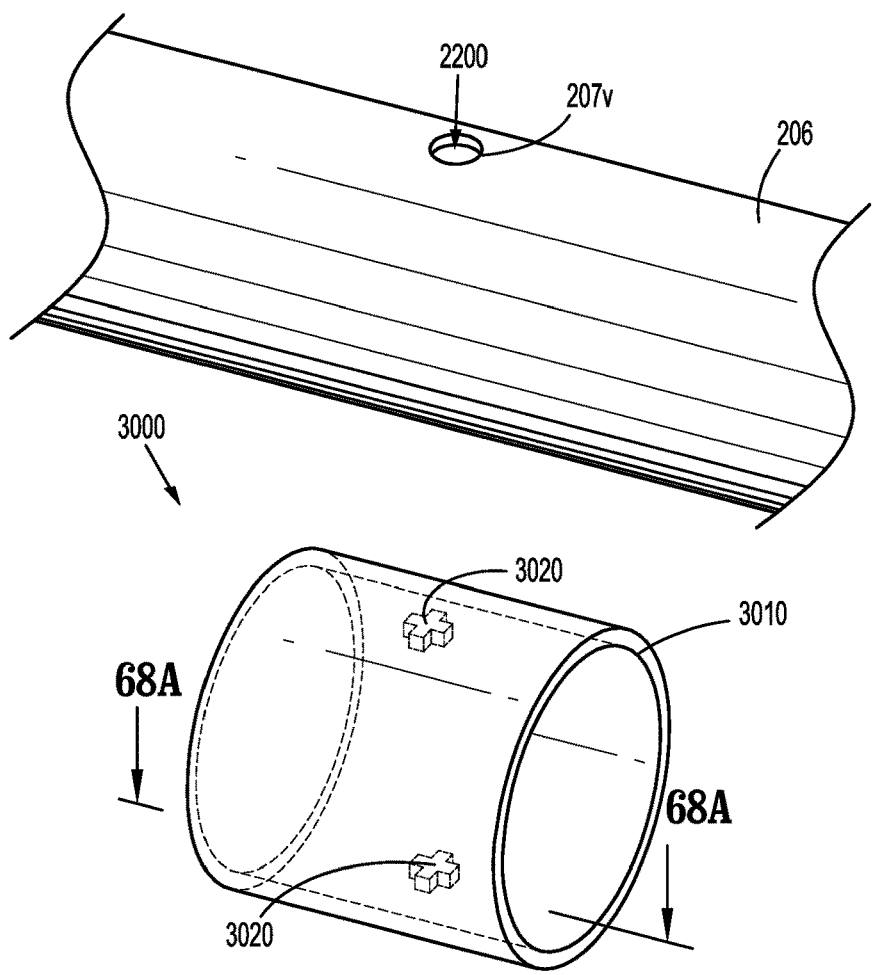
FIG. 68 is a perspective view of a portion of the surgical device and actuator of FIG. 67, with the actuator separated from the surgical device.
Figure 69:
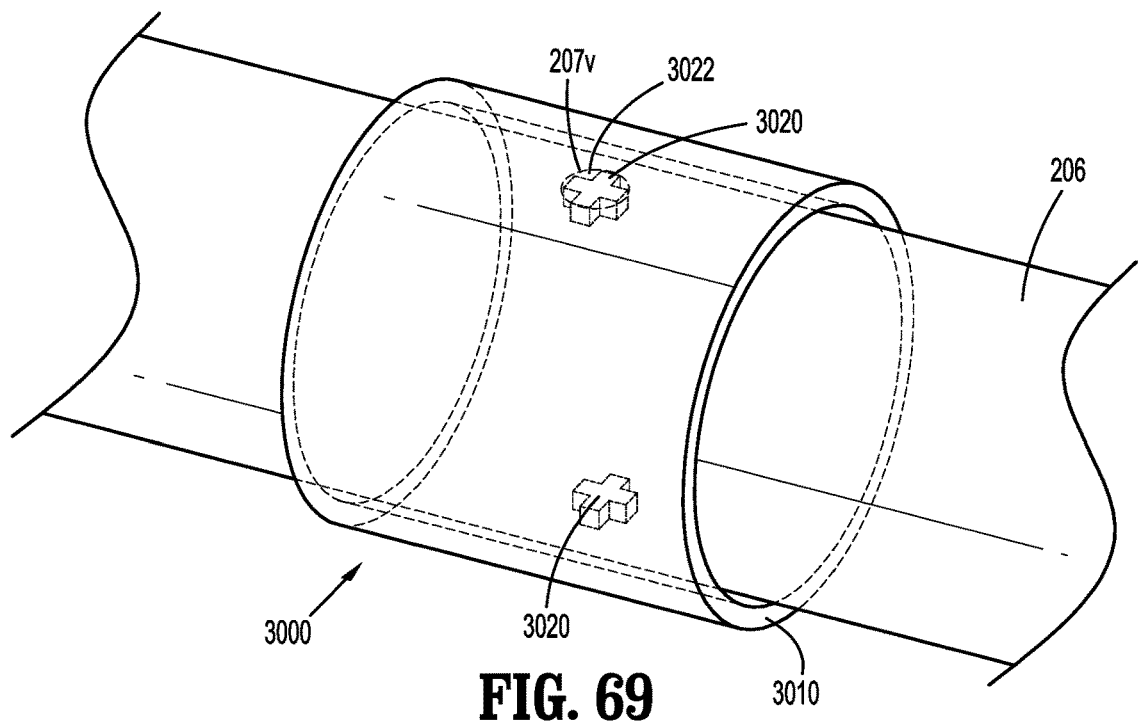
FIG. 69 is a perspective view of a portion of the surgical device of FIG. 67 with the actuator engaged therewith.

With initial reference to FIGS. 67-69, a first tool or actuator 3000 for opening valve 2200 of surgical device 10 is shown. Actuator 3000 includes a sleeve body 3010, and at least one post or finger 3020. Actuator 3000 is selectively engagable with surgical device 10 to surround or at least partially surround outer sleeve 206 of surgical device 10. Further, actuator 3000 is positionable adjacent valve 2200 of surgical device 10. Finger 3020 of actuator 3000 extends radially inward from sleeve body 3010 and is configured to selectively contact engagement portion 2220 of valve 2200.

The contact between finger 3020 of actuator 3000 and engagement portion 2220 of valve 2200 causes engagement portion 2220 of valve 2200 to deflect radially inward against the bias of biasing element 2230, thereby moving engagement portion 2220 to its open position to allow water and/or air to travel through port 207v of surgical device 10.

Figure 68A:
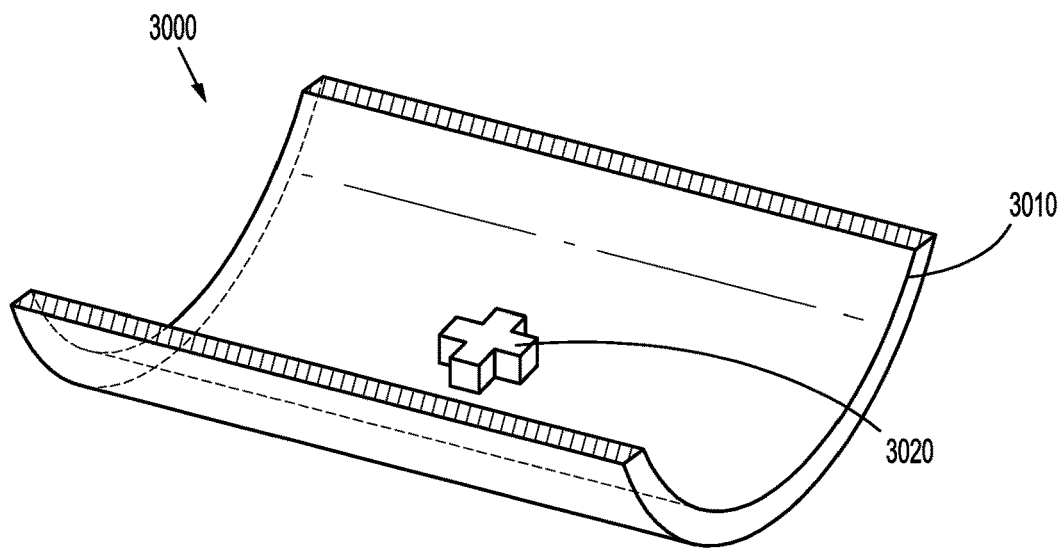
FIG. 68A is a cut-away view of the actuator taken along line 68A-68A of FIG. 68.

As shown in FIGS. 68 and 68A, the shape of finger 3020 is different than the shape of engagement portion 2220 of valve 2200 and port 207v. While both engagement portion 2220 of valve 2200 and port 207v have a circle or circular transverse cross-sectional profile, finger 3020 includes a plus sign-like or cruciform shape transverse cross-sectional profile. The difference in shapes or cross-sectional profiles between finger 3020 of actuator 3000 and engagement portion 2220 of valve 2200 (and/or port 207v) facilitates air/water to flow through spaces 3022 (FIG. 69) therebetween. While finger 3020 is shown having a particular shape, the present disclosure also contemplates fingers 3020 having other shapes or transverse cross-sectional profiles, including but not limited to a circle.

Figure 70:
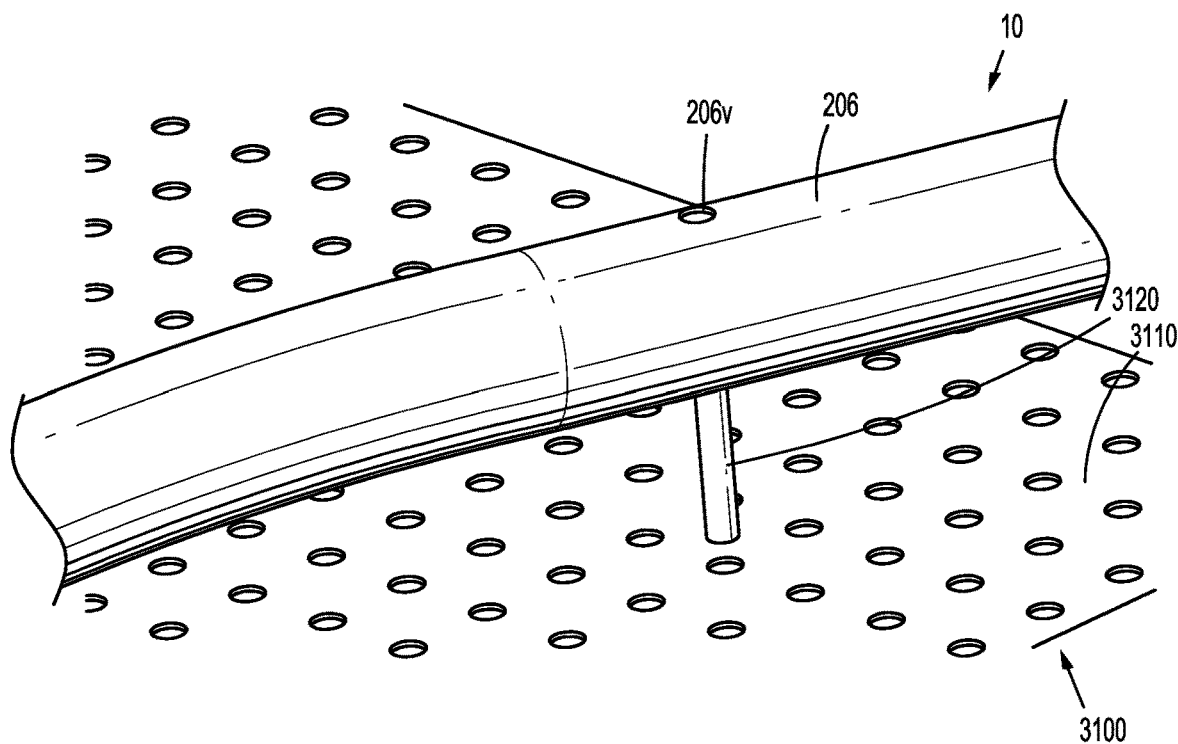
FIG. 70 is a perspective view of the surgical device of FIG. 67 engaged with a second actuator.
Figure 71:
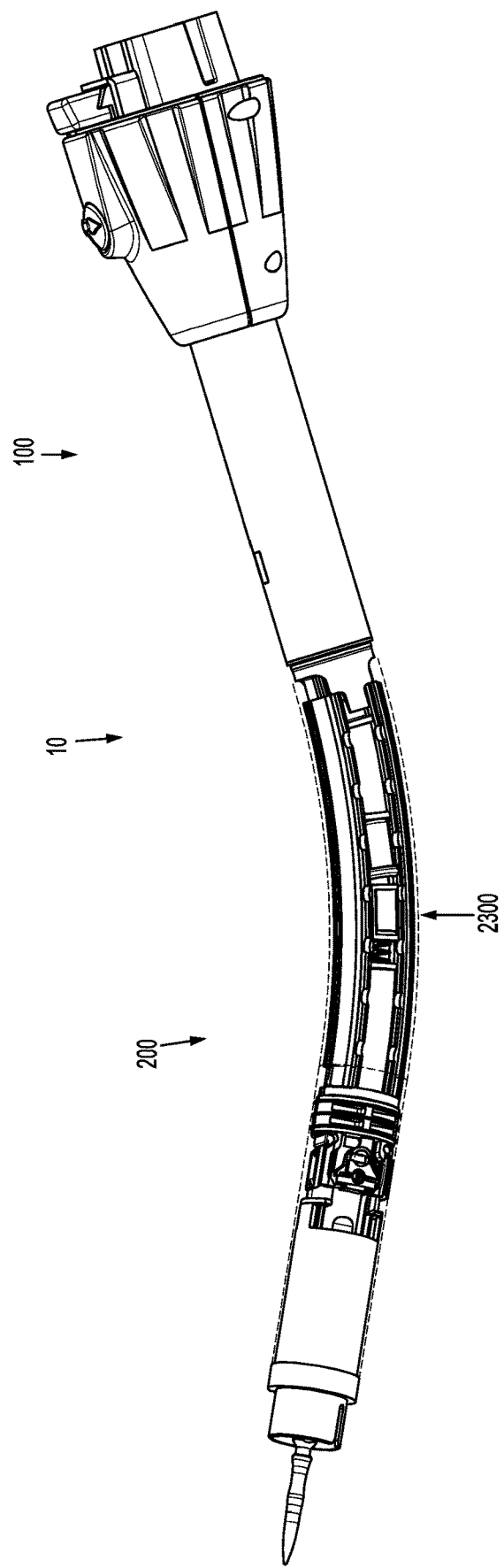
FIG. 71 is a perspective view of a surgical device including a valve in accordance with an embodiment of the present disclosure.

Referring now to FIG. 70, a second tool or actuator 3100 for opening valve 2200, 2200a of surgical device 10 is shown. Actuator 3100 is in the form of a rack 3110 (e.g., a drying rack) having at least one post 3120 extending therefrom. Post 3120 of actuator 3100 is positionable or selectively engagable with valve 2200, 2200a of surgical device 10 to selectively contact engagement portion 2220, 2220a of respective valve 2200, 2200a.

The contact between post 3120 of actuator 3100 and engagement portion 2220, 2220a of valve 2200, 2200a causes respective engagement portion 2220, 2220a to deflect radially inward against the bias of biasing element 2230, thereby moving engagement portion 2220, 2220a to its open position to allow water and/or air to travel through port 207v, 207va of surgical device 10.

As shown in FIG. 70, the shape of post 3120 of actuator 3100 is cylindrical. It is envisioned that post 3120 includes a shape other than cylindrical or transverse cross-sectional profile other than circular, such as a plus sign-like or cruciform shape or transverse cross-sectional profile, as discussed above with regard to finger 3020 of actuator 3000. It is also envisioned that the cross-section of cylinder of post 3120 is smaller than the cross-section of engagement portion 2220, 2220a of respective valve 2200, 2200a to facilitate air/water to flow therebetween. Further, while rack 3110 is shown having a single post 3120, the present disclosure also contemplates rack 3110 having multiple posts 3120 to simultaneously engage multiple valves 2200, 2200a, for instance.

The present disclosure also includes methods of drying and/or venting a surgical instrument (e.g., surgical device 10) utilizing actuator 3000 and/or actuator 3100. For instance, disclosed methods include engaging actuator 3000 with surgical device 10 (e.g., after surgical device has been cleaned with a fluid), positioning finger 3020 of actuator in contact with engagement portion 2220 of valve 2200, and moving engagement portion 2220 of valve 2200 to its open position to facilitate water/air to travel through port 207v of surgical device 10 to help dry internal components of surgical device 10. Other disclosed methods include positioning surgical device 10 onto rack 3110 of second actuator 3100 (e.g., after surgical device has been cleaned with a fluid), positioning post 3120 of actuator 3100 in contact with engagement portion 2220, 2220a of respective valve 2200, 2200a, and moving engagement portion 2220, 2220a to its open position to facilitate water/air to travel through respective port 207v, 207va of surgical device 10 to help dry internal components of surgical device 10.

Additionally, the present disclosure includes surgical kits including surgical device 10 having at least one valve 2200, 2200a, and actuator 3000 and/or actuator 3100.

Referring now to FIGS. 71-76, a valve 2300 for use with surgical device 10, adapter assembly 100, and/or extension assembly 200 of the present disclosure is shown. Valve 2300 is positioned within surgical device 10 and is configured to selectively engage a first opening or port 207p (FIG. 72) extending through outer sleeve 206 of extension assembly 200 for selectively allowing air, steam and/or fluid to pass through port 207p during cleaning, sanitizing, drying or venting of surgical device 10, for example.

Figure 73:
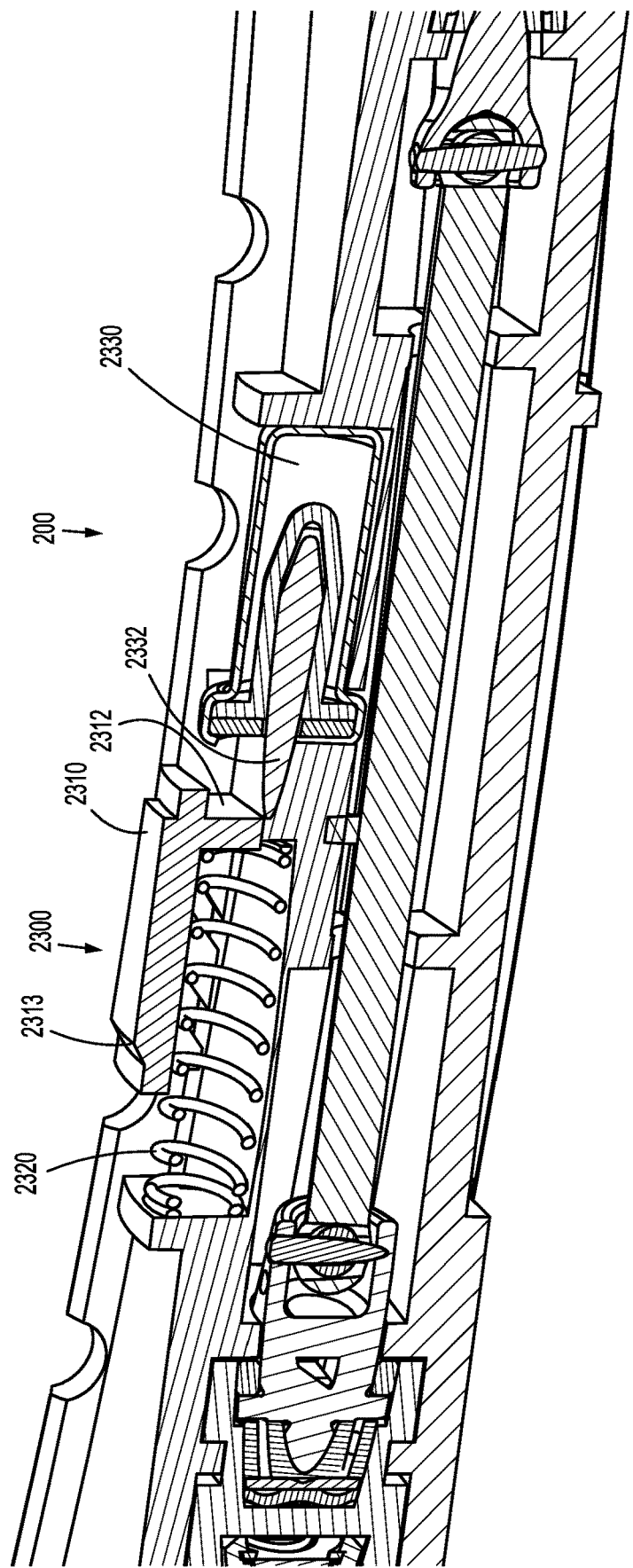
FIG. 73 is a cut-away view of the portion of the surgical device and valve of FIG. 72.

With particular reference to FIG. 73, valve 2300 includes a vent 2310, a biasing element 2320, and a thermostat 2330. Vent 2310 is slidably disposed with respect to port 207p of outer sleeve 206 between an open position (e.g., distally, or to the left in FIG. 73) and an occluding position (e.g., proximally, or to the right in FIG. 73) with respect to port 207p. Biasing element 2320 is in contact with a lip 2312 of vent 2310 and is configured to urge vent 2310 towards the occluding position (e.g., proximally in FIG. 73). While biasing element 2320 is illustrated as a compression spring, other types of biasing elements are also contemplated by the present disclosure. Thermostat 2330 is positioned within extension assembly 200 and adjacent (e.g., proximally of) vent 2310. A piston 2332 of thermostat 2330 is configured to selectively urge vent 2310 towards the open position (e.g., distally) against the bias of biasing element 2320.

Figure 74:
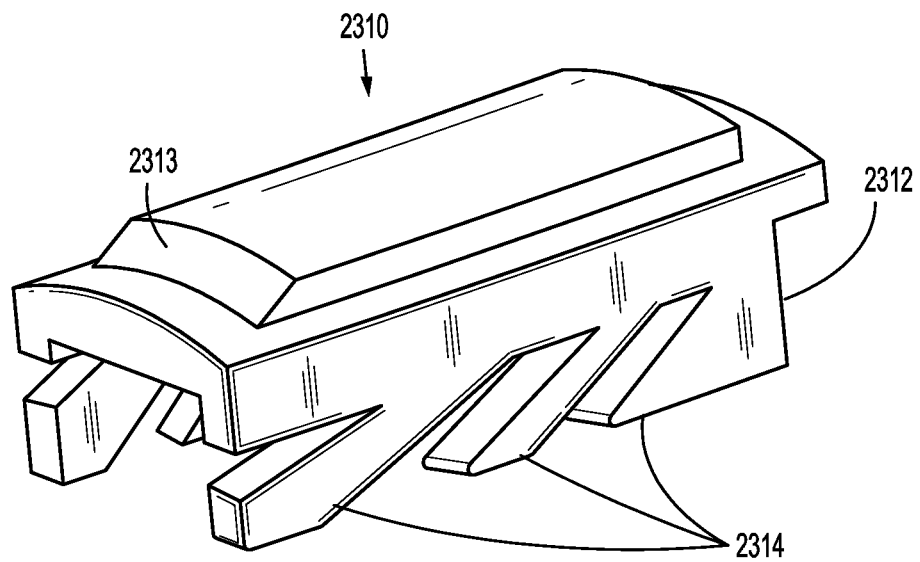
FIG. 74 is a perspective view of a vent of the valve of FIGS. 71-73.

More particularly, and with specific reference to FIG. 74, vent 2310 includes a ramped surface 2313 towards its distal end which is configured to facilitate a portion of vent 2310 being displaced under (e.g., radially within) outer sleeve 206. Additionally, as shown in FIG. 74, vent 2310 includes a plurality of legs 2314 (e.g., spring-like legs) which are configured to allow at least a portion (e.g., a distal portion) of vent 2310 to flex with respect to a different portion (e.g., a proximal portion) of vent 2310 to further facilitate a portion of vent 2310 being displaced under outer sleeve 206.

Figure 75:
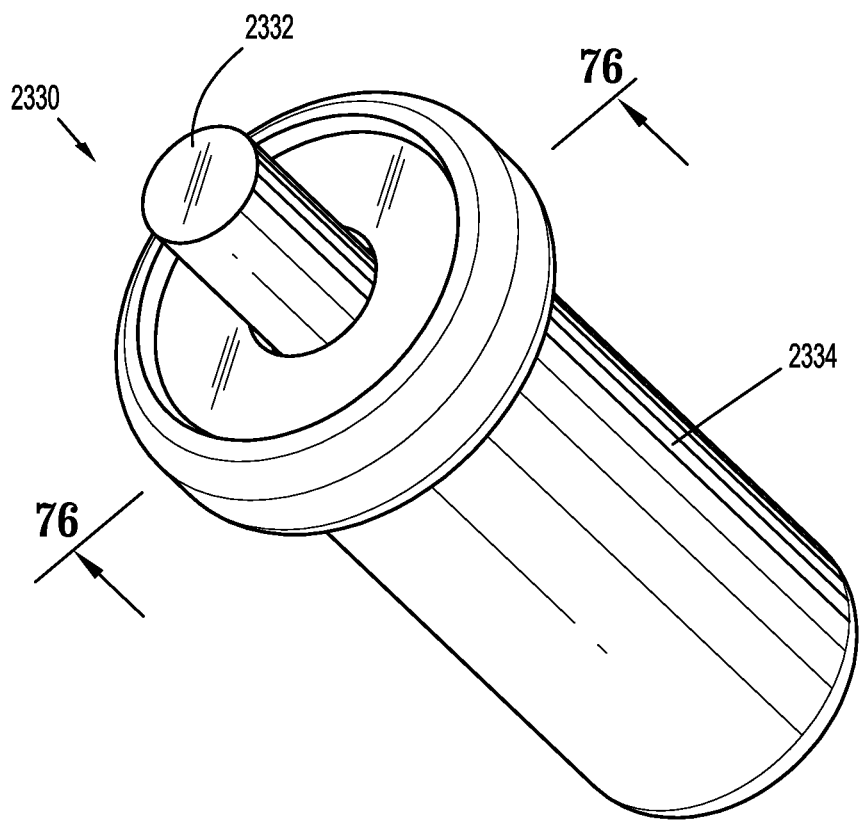
FIG. 75 is a perspective view of a thermostat of the valve of FIGS. 71-73.
Figure 76:
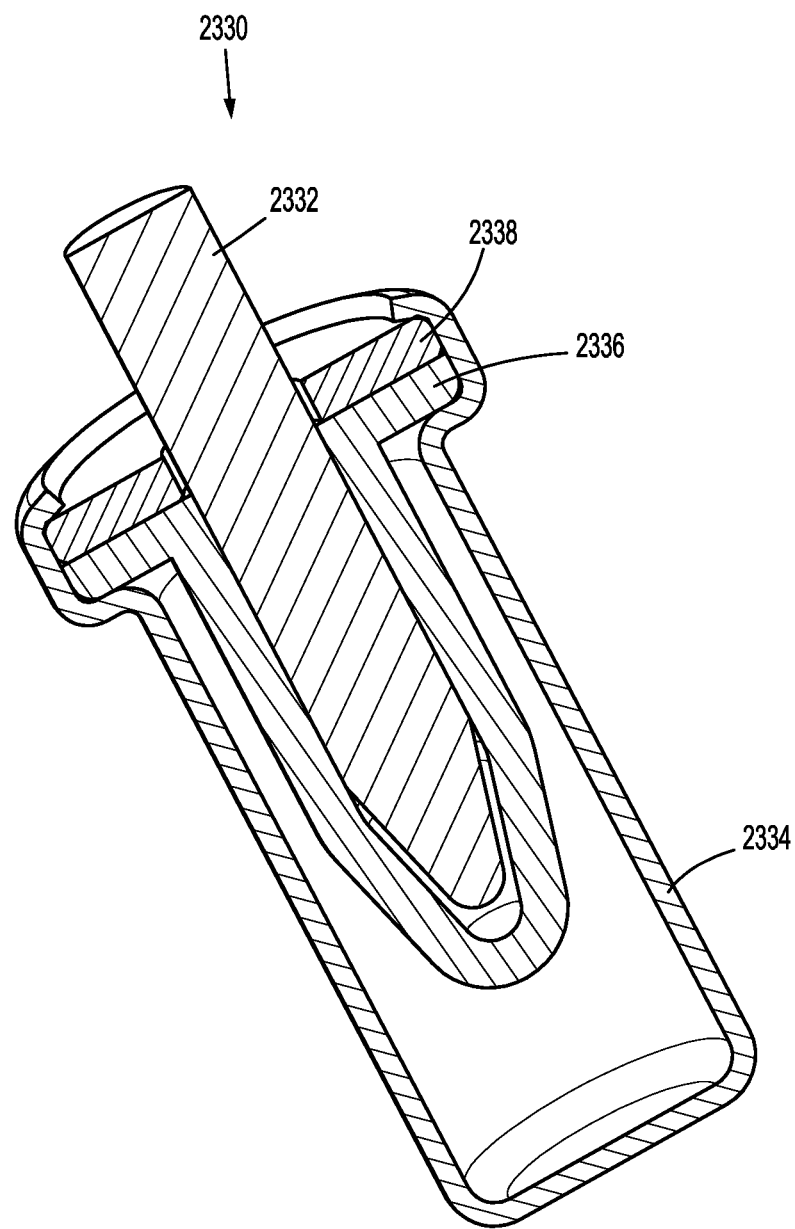
FIG. 76 is a cross-sectional view of the thermostat of FIG. 75 taken along line 76-76 of FIG. 75.

With particular reference to FIGS. 75 and 76, further details of thermostat 2330 are shown. Thermostat 2330 includes piston 2332, a housing 2334, a diaphragm 2336, and a washer 2338. Piston 2332 of thermostat 2330 is configured to move between an initial (e.g., proximal) position and an extended (e.g., distal) position. More particularly, when thermostat 2330 is exposed to a particular minimum temperature (e.g., about 130° C.), piston 2332 (e.g., a thermally-activated piston) automatically moves from its initial position to its extended position. When moving to its extended position, piston 2332 moves vent 2310 (via contact with lip 2312 thereof) from its occluding position to its open position. Further, when the temperature of thermostat 2330 falls below the minimum temperature, piston 2332 automatically moves from its extended position to its initial position, thereby allowing biasing element 2320 to move vent 2310 from its open position to its occluding position.

In the occluding position, vent 2310 provides a fluid-tight seal with port 207p, which prevents fluid, steam, air or gas from entering or exiting outer sleeve 206 through port 207p. When vent 2310 is in the open position, fluid, steam, air and/or gas are able to enter and exit outer sleeve 206 through the space between vent 2310 and port 207p (e.g., walls defining port 207p).

When surgical device 10 is used to perform a surgical task, vent 2310 is in its biased, occluding position. In this position, bodily fluid and gas are prevented or hindered from entering or exiting surgical device 10 through port 207p.

When cleaning debris from surgical device 10 (e.g., after a surgical procedure) is desired, a user can introduce fluid or steam through a port of surgical device 10. Prior to such a cleaning process, vent 2310 is in its occluding position to help prevent fluids or gas from entering surgical device 10 through port 207p. During the cleaning and/or sterilization process, when the temperature (e.g., of the steam) adjacent thermostat 2330 reaches or exceeds the pre-determined minimum temperature (e.g., about 130° C.), piston 2332 of thermostat 2330 automatically moves from its initial position to its extended position, which thereby moves vent 2310 to its open position. In its open position, vent 2310 facilitates the drying and venting of surgical device 10 by creating a path (e.g., an additional path) for the air, steam and/or fluid to exit surgical device 10. Further, when the temperature adjacent thermostat 2330 inside surgical device 10 falls below the pre-determined minimum temperature (e.g., about 130° C.; or a different pre-determined temperature), piston 2332 of thermostat 2330 automatically moves from its extended position to its initial position, thereby allowing biasing element 2320 to move vent 2310 back to its occluded position.

Figure 72:
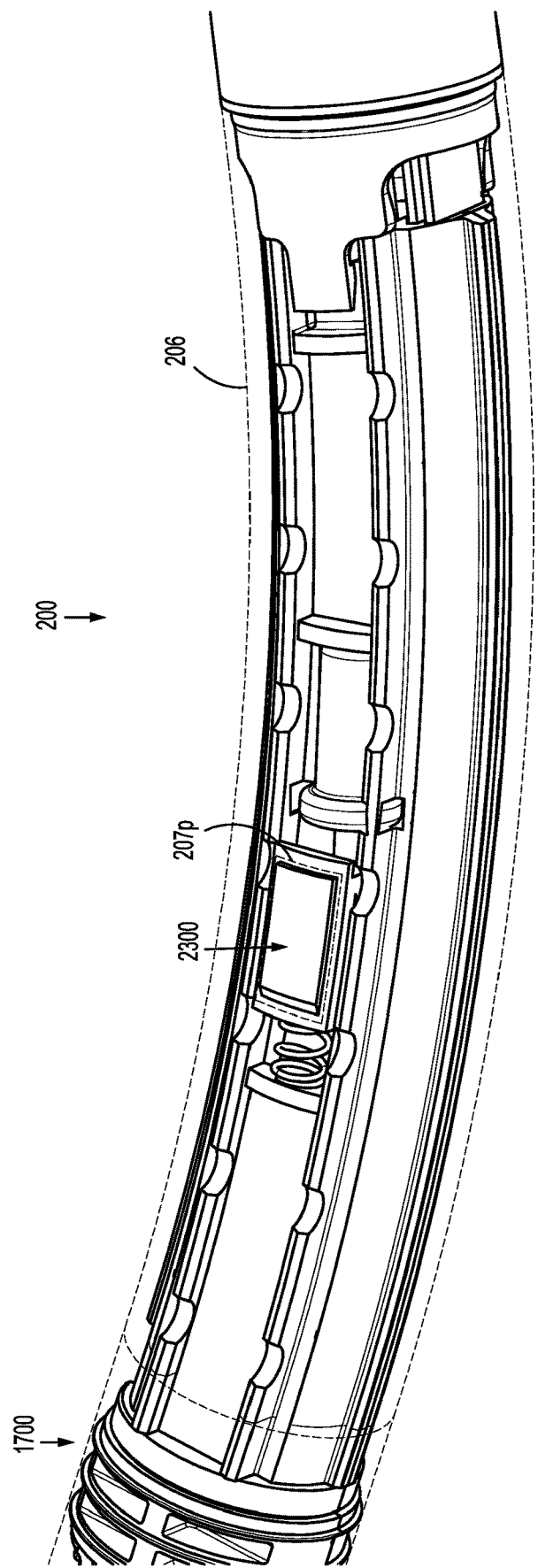
FIG. 72 is a perspective view of a portion of the surgical device of FIG. 71 illustrating the valve and showing internal components.

Additionally, while valve 2300 and port 207p are shown in a particular location on surgical device 10 (e.g., proximally of seal assembly 1700; FIG. 72), other locations of valve 2300 and port 207p are contemplated by the present disclosure. Further, surgical device 10 may include more than one valve 2300, and more than one associated port 207p. For instance, multiple valves 2300 and ports 207p can be used to create a particular path for fluid and air to flow to facilitate cleaning, venting and drying surgical device 10. Additionally, while port 207p is depicted as being rectangular in shape, port 207p may be another type of regular or irregular shape.

Additionally, while valve 2300 is shown and described for use with a particular type of surgical device 10, valve 2300 is usable with various types of surgical instruments (e.g., reusable) where cleaning and/or sterilization may be desired.

The present disclosure also includes methods of cleaning a surgical instrument (e.g., surgical device 10) utilizing valve 2300. For instance, disclosed methods include introducing fluid or steam within surgical device 10 through a port, and automatically moving vent 2310 of valve 2300 from its occluding position to its open position, based on the temperature within surgical device 10, to allow fluid and gas to enter and exit surgical device 10 to facilitate venting and drying internal components of surgical device 10. Methods also include automatically moving vent 2310 of valve 2300 from its open position to its occluding position in response to a temperature, adjacent thermostat 2330, falling below a pre-determined value.

Figure 77:
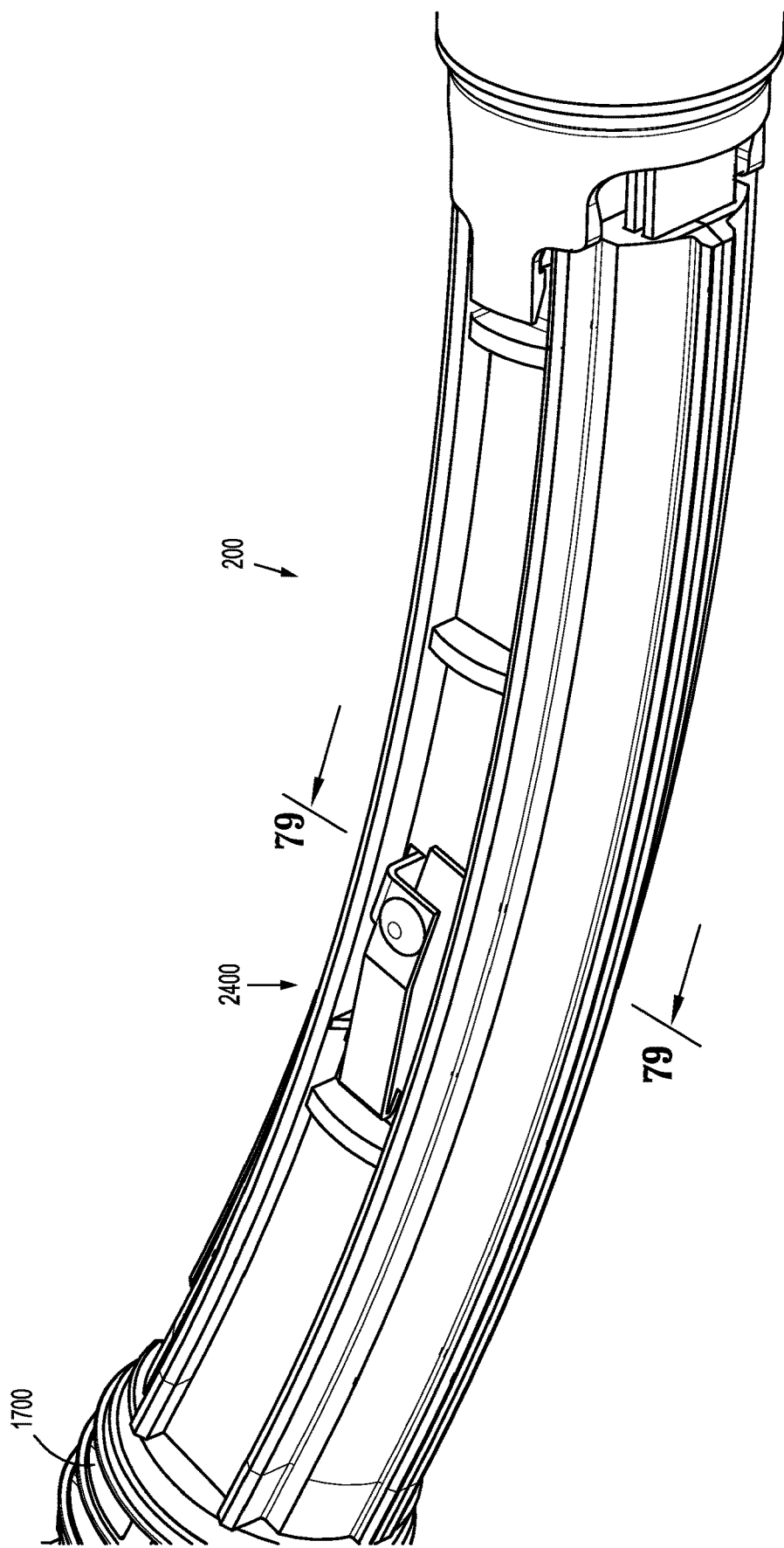
FIG. 77 is a perspective view of a portion of a surgical device with portions removed and showing a valve in accordance with an embodiment of the present disclosure.
Figure 78:
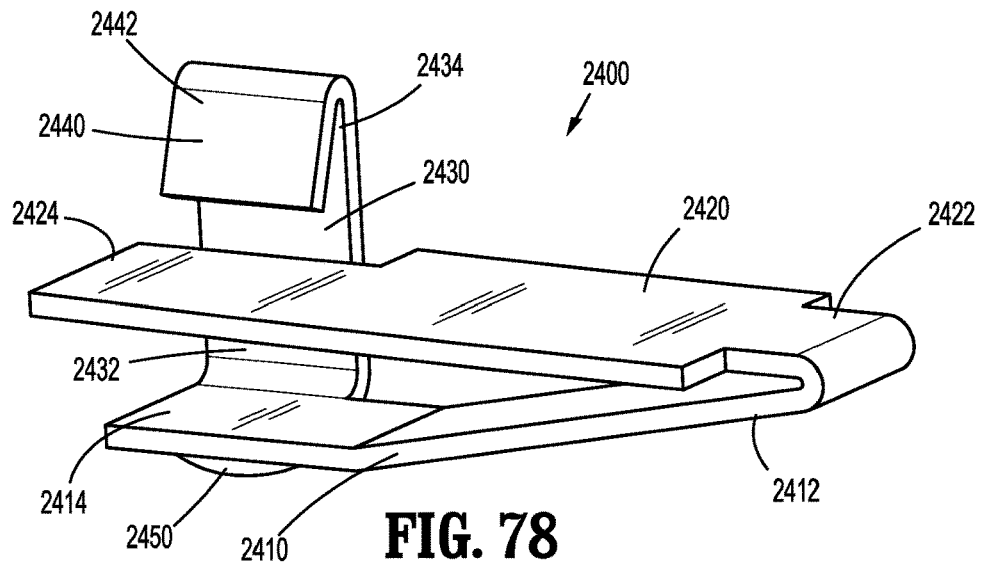
FIG. 78 is a perspective view of the valve of FIG. 77.
Figure 79:
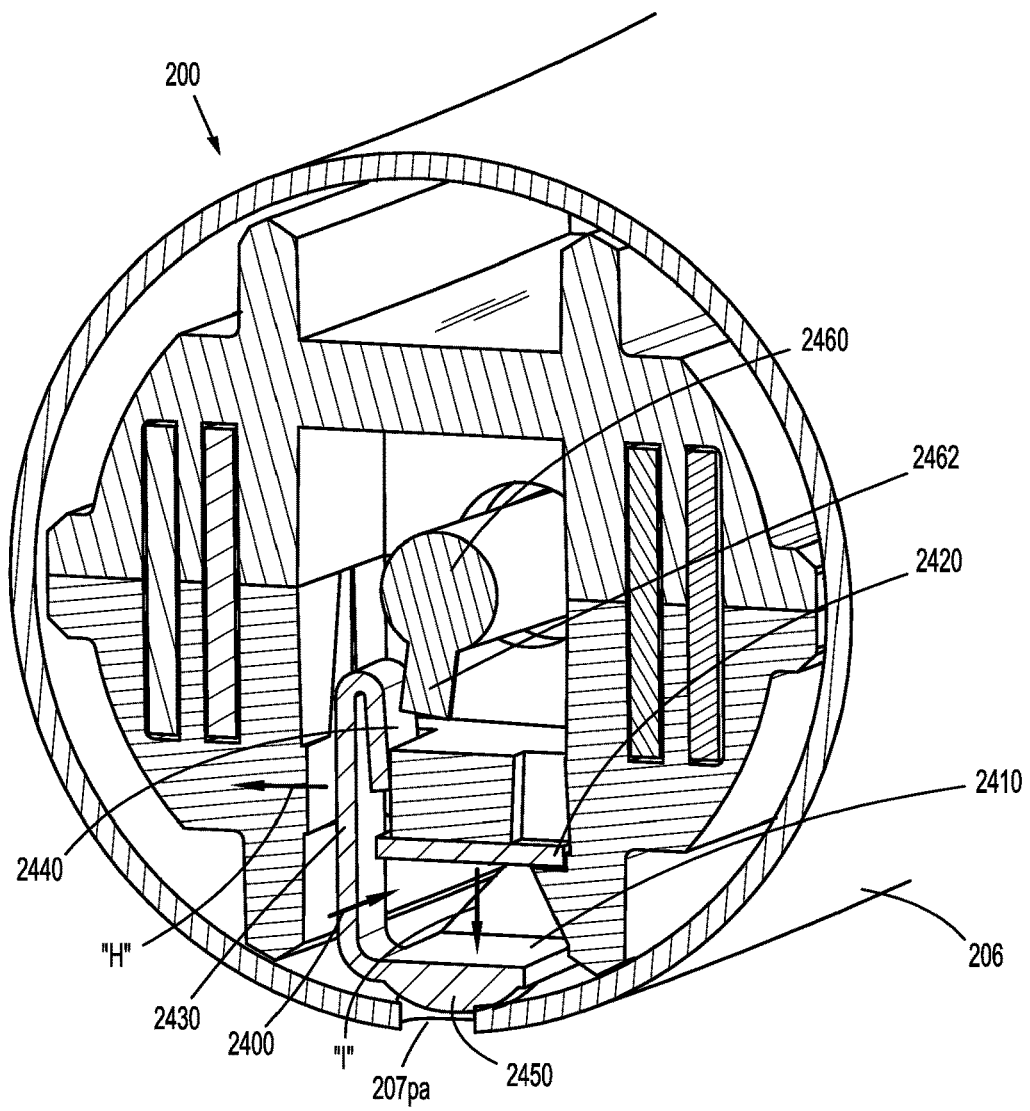
FIG. 79 is a cut-away view taken along line 79-79 of FIG. 77, illustrating the valve in an open position.

Referring now to FIGS. 77-79, a valve 2400 for use with surgical device 10, adapter assembly 100, and/or extension assembly 200 of the present disclosure is shown. Valve 2400 is positioned within surgical device 10 and is configured to selectively engage a first opening or port 207pa (FIG. 79) extending through outer sleeve 206 of extension assembly 200 for selectively allowing air, steam and/or fluid to pass through port 207pa during cleaning, sanitizing, drying or venting of surgical device 10, for example.

At least some portions of valve 2400 are made from a bimetal material, and valve 2400 includes several folded or bent portions, as detailed herein. With particular reference to FIG. 78, valve 2400 includes a first leg 2410, a second leg 2420, a third leg 2430, a fourth leg 2440, and an occluding portion 2450. A first end 2422 of second leg 2420 extends from a first end 2412 of first leg 2410 such that first leg 2410 is pivotal relative to second leg 2420. A first end 2432 of third leg 2430 extends (e.g., perpendicularly) adjacent a second end 2414 of first leg 2410. A first end 2442 of fourth leg 2440 extends (e.g., at an acute angle) from a second end 2434 of third leg 2430. Occluding portion 2450, which may be made from rubber or a similar material which facilitates sealing, extends outward from first leg 2410 (e.g., adjacent second end 2414 thereof) and is configured to selectively engage port 207pa (FIG. 79) in a sealing arrangement.

The bimetal material included on valve 2400 is configured to bend or otherwise change shape when subjected to a predetermined temperature (e.g., about 130° C.), such that portions of valve 2400 are movable between an open position and an occluding position with respect to port 207pa. In particular, when surgical device 10 is heated and valve 2400 is subjected to the predetermined temperature, first leg 2410 of valve 2400 is configured to move toward second leg 2420 of valve 2400 (e.g., from the occluding position to the open position). More particularly, due to the arrangement of first leg 2410 and second leg 2420, second end 2414 of first leg 2410 of valve 2400 is configured to move away from port 207pa and toward a second end 2424 of second leg 2420 of valve 2400. The movement of first leg 2410 away from port 207pa also moves occluding portion 2450 of valve 2400 away from and out of engagement with port 207pa to its open position.

In the open position, fluid, steam, air and/or gas are able to enter and exit outer sleeve 206 through the space between occluding portion 2450 of valve 2400 and port 207pa (e.g., walls defining port 207pa). In the occluding position, occluding portion 2450 of valve 2400 provides a fluid-tight seal with port 207pa, which prevents fluid, steam, air or gas from entering or exiting outer sleeve 206 through port 207pa.

When surgical device 10 is used to perform a surgical task, occluding portion 2450 of valve 2400 is in its occluding position with respect to port 207pa. In this position, bodily fluid and gas are prevented or hindered from entering surgical device 10 through port 207pa.

When cleaning debris from surgical device 10 (e.g., after a surgical procedure) is desired, a user can introduce fluid or steam through a port of surgical device 10. Prior to such a cleaning process, occluding portion 2450 of valve 2400 is in its occluding position to help prevent fluid or gas from entering surgical device 10 through port 207pa. During the cleaning and/or sterilization process, when the temperature (e.g., of the steam) adjacent valve 2400 reaches or exceeds the pre-determined minimum temperature (e.g., about 130° C.), first leg 2410 of valve 2400 moves (e.g., bends or pivots) toward second leg 2430 of valve 2400 due to the characteristics of the bimetal material from which portions of valve 2400 are made. As noted above, the movement of first leg 2410 toward second leg 2420 also moves occluding portion 2450 of valve 2400 from its occluding position to its open position with respect to port 207pa, thereby facilitating drying and venting of surgical device 10 by creating a path (e.g., an additional path) for the air, steam and fluid to exit surgical device 10.

When the cleaning or sanitizing process is complete, and when the temperature within surgical device 10 adjacent valve 2400 falls below the pre-determined minimum temperature, the bimetal characteristics of valve 2400 cause valve 2400 to retain its shape (e.g., in the open position). That is, occluding portion 2450 of valve 2400 remains in the open position with respect to port 207pa while surgical device 10 is cooling and after it has cooled. The open port 207pa allows additional drying and venting to occur even after the temperature within surgical device 10 has fallen below the pre-determined minimum temperature.

With particular reference to FIG. 79, to move occluding portion 2450 of valve 2400 to its occluding position (e.g., when reusing surgical device 10), a user actuates a handle or other actuator to rotate a shaft 2460 of surgical device 10 relative to valve 2400. The rotation of shaft 2460 causes a latch 2462 of shaft 2460 to engage fourth leg 2440 of valve 2400. The engagement between latch 2462 of shaft 2460 and fourth leg 2440 of valve 2400 causes third leg 2430 of valve 2400 to flex or bend in the general direction of arrow "H", which causes first leg 2410 of valve 2400 to move away from second leg 2420 of valve 2400, such that occluding portion 2450 moves in the general direction of arrow "I" into its occluding position.

Additionally, while valve 2400 and port 207pa are shown in a particular location on surgical device 10 (e.g., proximally of seal assembly 1700; FIG. 77), other locations of valve 2400 and port 207pa are contemplated by the present disclosure. Further, surgical device 10 may include more than one valve 2400, and more than one associated port 207pa. For instance, multiple valves 2400 and ports 207pa can be used to create a particular path for fluid and air to flow to facilitate cleaning, venting and drying surgical device 10.

Additionally, while valve 2400 is shown and described for use with a particular type of surgical device 10, valve 2400 is usable with various types of surgical instruments (e.g., reusable) where cleaning and/or sterilization may be desired.

The present disclosure also includes methods of cleaning a surgical instrument (e.g., surgical device 10) utilizing valve 2400. For instance, disclosed methods include inserting fluid or steam through port 207pa or a different port, and automatically moving occluding portion 2450 valve 2400 from its occluding position to its open position, based on the temperature and the bimetal properties of portions of valve 2400, to allow fluid and gas to enter and exit surgical device 10 to facilitate drying internal components of surgical device 10. Methods also include maintaining occluding portion 2450 of valve 2400 in its open position after the temperature falls below a pre-determined temperature. Additionally, methods include actuating a portion of surgical device 10 to manually move occluding portion 2450 of valve 2400 to its occluding position.

Referring now to FIGS. 80-84, a wick 2500 for use with surgical device 10, adapter assembly 100, and/or extension assembly 200 of the present disclosure is shown. Wick 2500 is positioned within surgical device 10 and is configured to absorb residual moisture from within portions of surgical device 10, adapter assembly 100, and/or extension assembly 200 and allow the moisture to travel to drier portions (or portions easier to dry) thereof during the drying, cleaning or sanitizing process to help improve moisture removal.

Wick 2500 is made from synthetic or natural fibers (e.g. a fibrous material), which may readily absorb, transmit, and desorb liquid (e.g., water). For instance, wick 2500 may be a cloth, fiber sheet, or thread of suitable thickness, or a combination of materials. It is contemplated that wick 2500 may be impregnated with desiccating compounds, materials or the like (e.g., activated alumina, aerogel, benzophenone, bentonite clay, calcium chloride, calcium oxide, calcium sulfate, cobalt(II) chloride, copper(II) sulfate, lithium chloride, lithium bromide, magnesium sulfate, magnesium perchlorate, molecular sieve, potassium carbonate, potassium hydroxide, silica gel, sodium, sodium chlorate, sodium chloride, sodium hydroxide, sodium sulfate, sucrose and/or sulfuric acid).

Wick 2500 is positioned such that a first part of wick 2500 (e.g., a proximal portion 2510) is within a first portion of surgical device (e.g., a proximal portion of extension assembly 200), and a second part of same wick 2500 (e.g., a distal portion 2520) is within a second portion of surgical device (e.g., a distal portion of extension assembly 200). Wick is configured to transfer the moisture from the wetter portion of wick 2500 (e.g., proximal portion 2510) to the dryer portion of wick 2500 (e.g., distal portion 2520). Further, wick 2500 increases surface area of the liquid within extension assembly 200 (for instance), thereby decreasing drying time.

Figure 80:
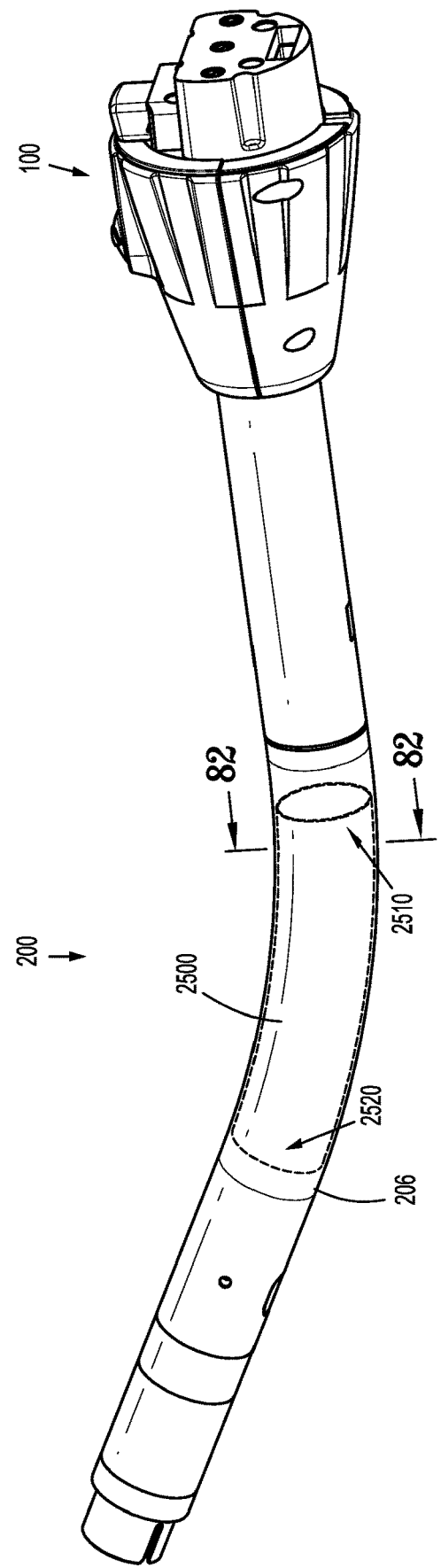
FIG. 80 is a perspective view of a surgical device including a wick in accordance with an embodiment of the present disclosure.
Figure 81:
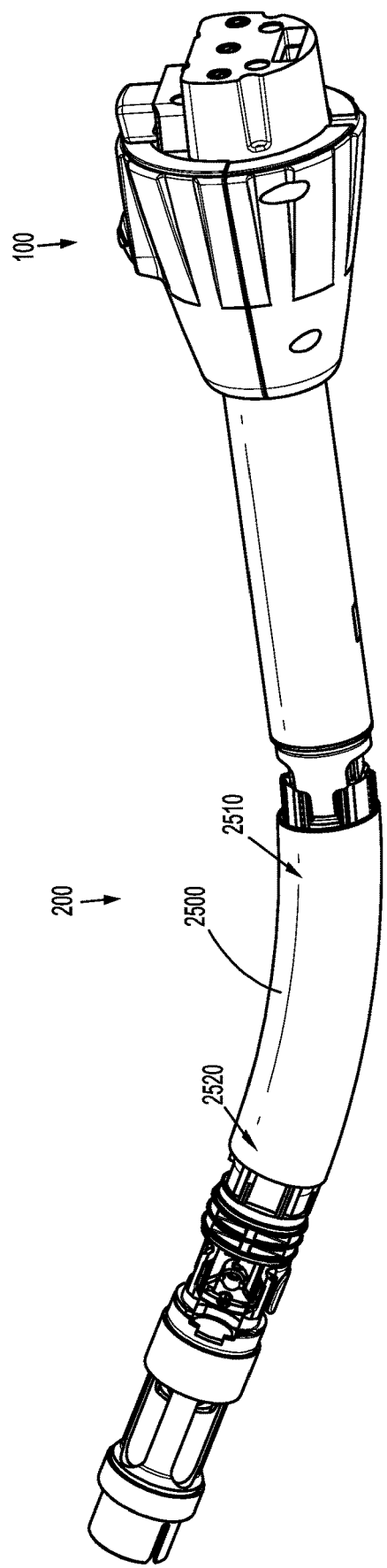
FIG. 81 is a perspective view of a portion of the surgical device of FIG. 80 illustrating the wick and showing internal components.
Figure 82:
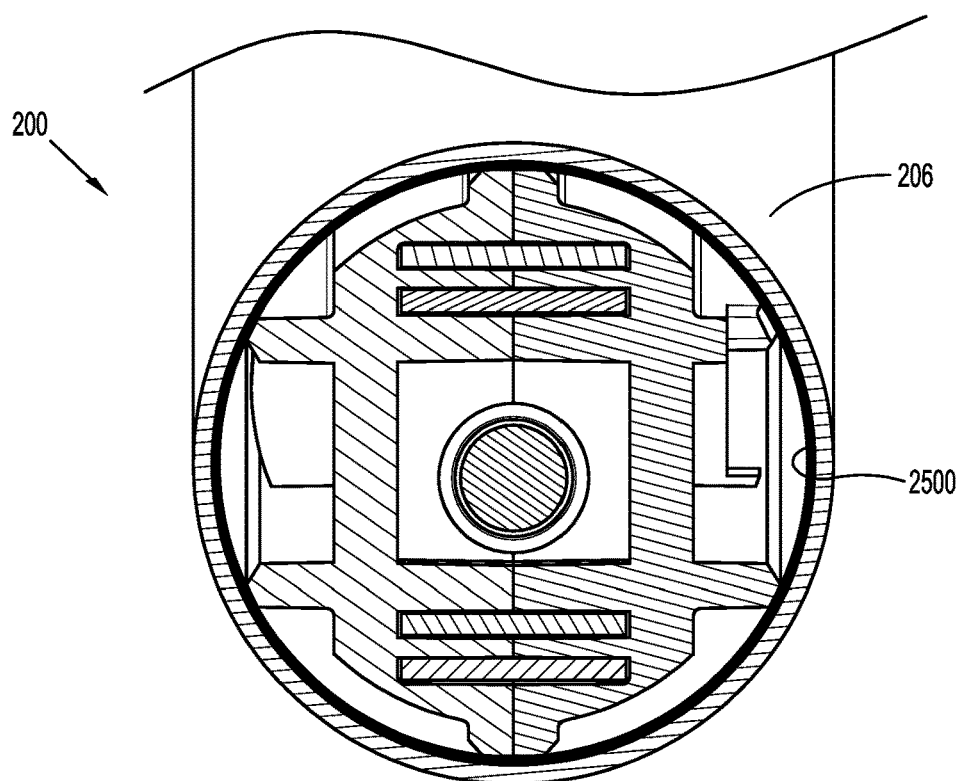
FIG. 82 is a cut-away view taken along line 82-82 of FIG. 80.

With particular reference to FIGS. 80-82, wick 2500 is in the shape of a cylindrical ring or sleeve, and is positioned within outer sleeve 206 of extension assembly 200. Here, when liquid is present within extension assembly 200 (e.g. during cleaning or sanitizing), a portion (e.g., proximal portion 2510) of wick 2500 is configured to absorb at least some of the liquid or moisture from within outer sleeve 206 of extension assembly 200 and transfer the liquid or moisture to another portion (e.g., distal portion 2520) of wick 2500. It is envisioned that distal portion 2520 of wick 2500 is in fluid communication with the outside of surgical device 10 (e.g., ambient air). Further, wick 2500 is configured to transfer liquid or moisture from a relatively wet portion of wick 2500 to a relatively dry portion of wick 2500, regardless of its location within extension assembly 200. Next, the liquid or moisture absorbed by wick 2500 desorbs or evaporates from wick 2500 into the ambient air and/or the air within surgical device 10.

Accordingly, wick 2500 helps remove liquid or moisture that entered surgical device 10 during use, cleaning and/or sanitization. Wick 2500 is usable with other types of valves, vents and other moisture control features, as discussed herein, or wick 2500 is usable without other types moisture control features. Further, since the presence of wick 2500 allows liquid or moisture to enter surgical device 10 without impacting its sanitization effectiveness, for instance, wick 2500 reduces the need for or tolerance of water-tight seals and unions, which thereby facilitates and/or reduces cost of manufacturing surgical device 10 or components thereof.

Additionally, while surgical device 10 is shown including a single wick 2500 in FIGS. 80-82, surgical device 10 may include more than one wick 2500 therein. Further, wick 2500 is shown including a cylindrical shape (including a circle cross-section), however wick 2500 may be any regular or irregular shape and may be positioned at any suitable location(s) within surgical device 10.

Figure 83:
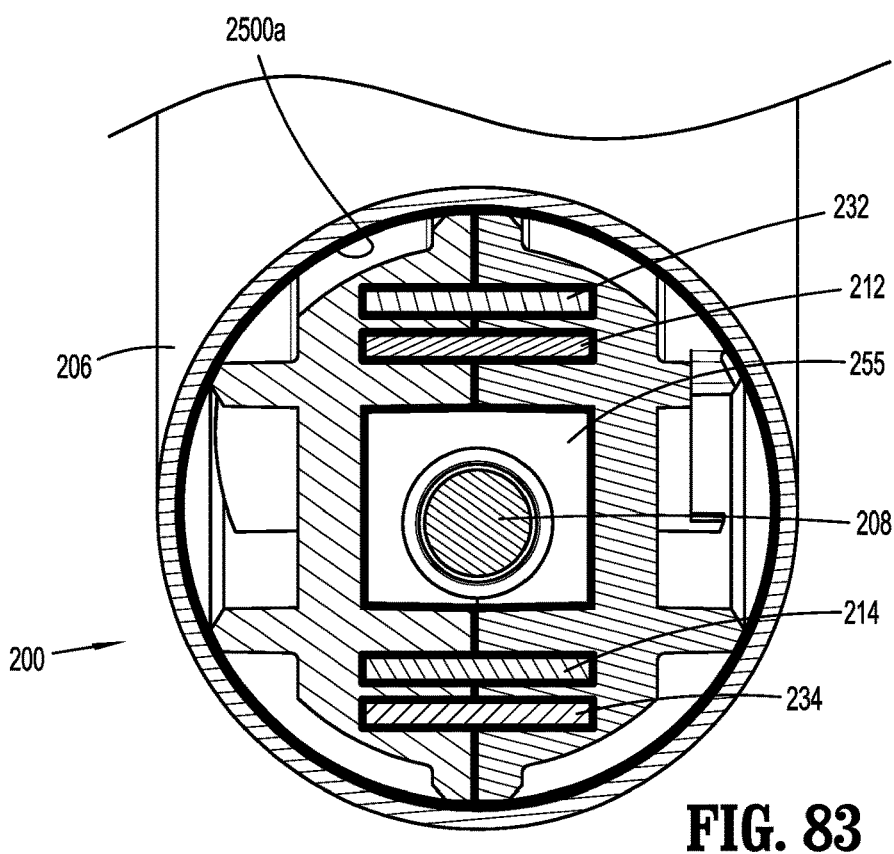
FIGS. 83 and 84 are cut-away views of different embodiments of the wick of the surgical device of FIGS. 80-82.

Referring now to FIG. 83, an additional embodiment of a wick 2500a is shown. Wick 2500a is similar to wick 2500 of FIGS. 80-82, but also surrounds, partially surrounds and/or passes between several internal components of extension assembly 200. In particular, wick 2500a surrounds longitudinal passage 255 (which surrounds drive shaft 208) and flexible bands 212, 214, 232, 234. While FIG. 83 indicates a single wick 2500a that surrounds various components, the present disclosure also includes wick 2500a having several un-connected segments.

Figure 84:
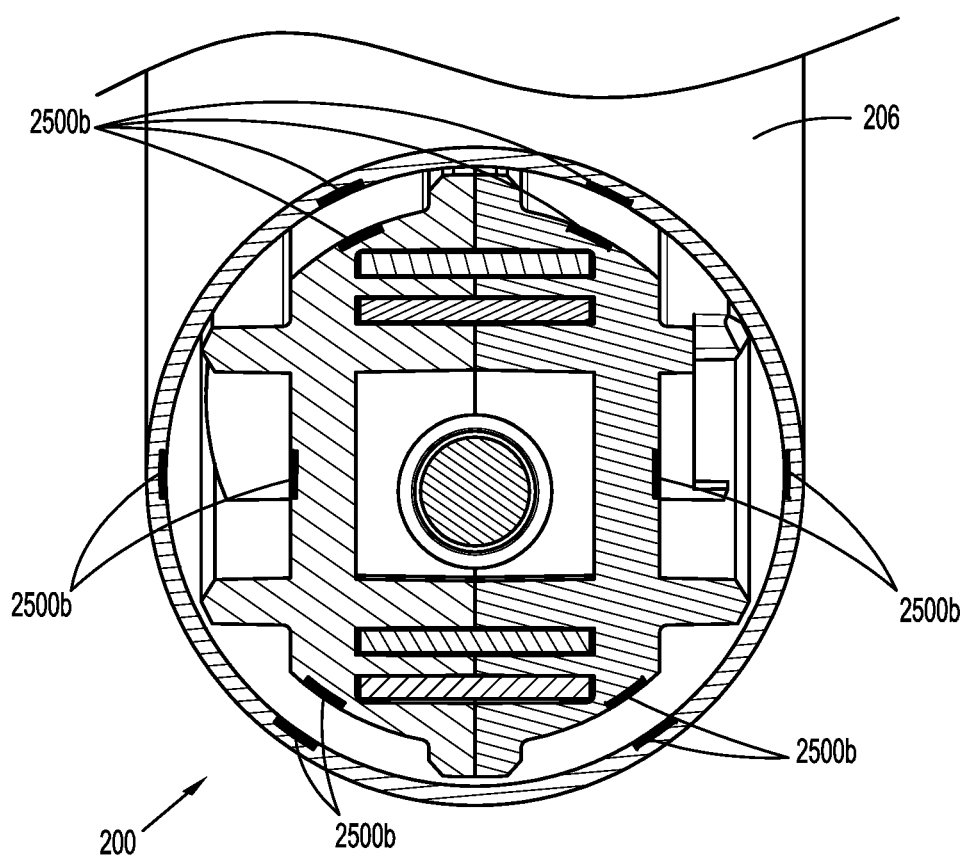

With reference to FIG. 84, extension assembly 200 is shown includes several wicks 2500b extending therethrough. Here, a plurality of wicks 2500b is strategically placed within extension assembly 200 to help dry out various portions thereof. While wicks 2500b are shown in particular locations within extension assembly 200, wicks 2500b may be included in other locations within surgical device 10. It is envisioned that each wick of the several wicks 2500b has the same length or a different length as one another. It is further envisioned that the several wicks 2500b are disposed within channels (e.g., recessed channels) of various components of extension assembly 200, for example.

The present disclosure also includes methods of drying and/or venting internal components of a surgical instrument (e.g., surgical device 10) utilizing wick 2500, 2500a, 2500b. For instance, disclosed methods include absorbing moisture or liquid from within extension assembly 200 using wick 2500, transferring the moisture or liquid from a relatively wet portion of wick 2500 to a relatively dry portion of wick 2500, and desorbing the moisture or liquid from wick 2500 to ambient air and/or air within surgical device 10.

Surgical devices such as those described herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Figure 85:
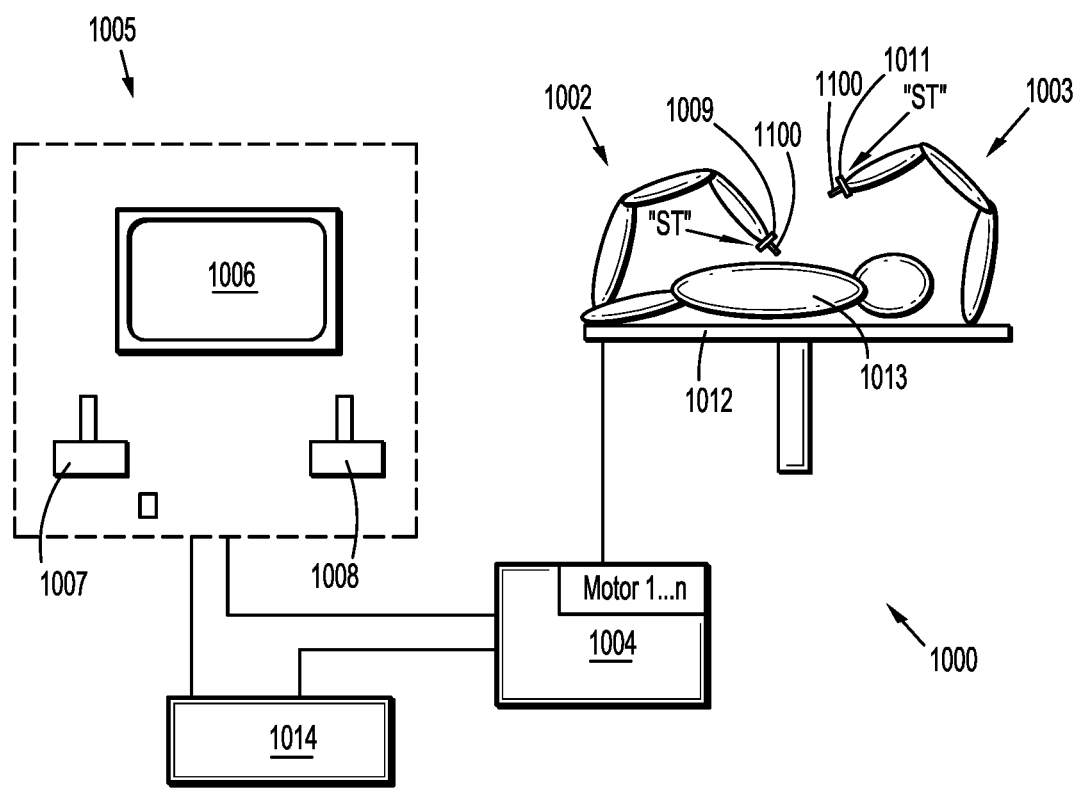
FIG. 85 is a schematic illustration of a robotic surgical system configured for use in accordance with the present disclosure.

Referring to FIG. 85, a medical work station is shown generally as work station 1000 and generally may include a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person (not shown), for example a surgeon, may be able to telemanipulate robot arms 1002, 1003 in a first operating mode.

Each of the robot arms 1002, 1003 may include a plurality of members, which are connected through joints, and an attaching device 1009, 1011, to which may be attached, for example, a surgical tool "ST" supporting an end effector 1100, in accordance with any one of several embodiments disclosed herein, as will be described in greater detail below.

Robot arms 1002, 1003 may be driven by electric drives (not shown) that are connected to control device 1004. Control device 1004 (e.g., a computer) may be set up to activate the drives, in particular by means of a computer program, in such a way that robot arms 1002, 1003, their attaching devices 1009, 1011 and thus the surgical tool (including end effector 1100) execute a desired movement according to a movement defined by means of manual input devices 1007, 1008. Control device 1004 may also be set up in such a way that it regulates the movement of robot arms 1002, 1003 and/or of the drives.

Medical work station 1000 may be configured for use on a patient 1013 lying on a patient table 1012 to be treated in a minimally invasive manner by means of end effector 1100. Medical work station 1000 may also include more than two robot arms 1002, 1003, the additional robot arms likewise being connected to control device 1004 and being telemanipulatable by means of operating console 1005. A medical instrument or surgical tool (including an end effector 1100) may also be attached to the additional robot arm. Medical work station 1000 may include a database 1014, in particular coupled to with control device 1004, in which are stored, for example, pre-operative data from patient/living being 1013 and/or anatomical atlases.

Reference is made herein to U.S. Pat. No. 8,828,023 to Neff et al., entitled "Medical Workstation," the entire content of which is incorporated herein by reference, for a more detailed discussion of the construction and operation of an exemplary robotic surgical system.

Any of the components described herein may be fabricated from either metals, plastics, resins, composites or the like taking into consideration strength, durability, wearability, weight, resistance to corrosion, ease of manufacturing, cost of manufacturing, and the like.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. A surgical device comprising:
   an elongated portion; and
   a wick disposed at least partially within the elongated portion and made from a fibrous material, the wick configured to transfer moisture from a first portion of the wick to a second portion of the wick.

2. The surgical device according to claim 1, wherein the wick is in the shape of a cylindrical sleeve.

3. The surgical device according to claim 1, wherein the wick is configured to transfer moisture from a proximal portion of the wick to a distal portion of the wick.

4. The surgical device according to claim 3, wherein the distal portion of the wick is in fluid communication with ambient air outside of the elongated portion.

5. The surgical device according to claim 1, wherein the wick is a fibrous sheet of material.

6. The surgical device according to claim 1, wherein the wick is impregnated with a desiccating compound.

7. The surgical device according to claim 6, wherein the desiccating compound includes at least one of activated alumina, aerogel, benzophenone, bentonite clay, calcium chloride, calcium oxide, calcium sulfate, cobalt(II) chloride, copper(II) sulfate, lithium chloride, lithium bromide, magnesium sulfate, magnesium perchlorate, molecular sieve, potassium carbonate, potassium hydroxide, silica gel, sodium, sodium chlorate, sodium chloride, sodium hydroxide, sodium sulfate, sucrose or sulfuric acid.

8. The surgical device according to claim 1, further including an end effector operatively engaged with a distal portion of the elongated portion.

9. The surgical device according to claim 8, wherein the wick is configured to transfer moisture from a proximal portion of the wick to a distal portion of the wick.

10. The surgical device according to claim 8, further including a drive shaft extending at least partially through the elongated portion and disposed in mechanical cooperation with the end effector.

11. The surgical device according to claim 10, wherein at least a portion of the wick surrounds a longitudinal passage which surrounds the drive shaft.

12. The surgical device according to claim 1, wherein the elongated portion includes an outer sleeve.

13. The surgical device according to claim 12, wherein an entirety of the wick is disposed within the outer sleeve.

14. A surgical device comprising:
    an elongated portion; and
    a wick disposed at least partially within the elongated portion, the wick defining a cylindrical sleeve.

15. The surgical device according to claim 14, wherein the wick and the elongated portion are coaxial.

16. The surgical device according to claim 14, wherein the wick is a fibrous sheet of material.

17. The surgical device according to claim 14, wherein the wick is impregnated with a desiccating compound.

18. A method of cleaning a surgical device, comprising:
    injecting fluid into the surgical device;
    absorbing a first amount of the fluid with a first portion of a wick disposed at least partially within the surgical device; and transferring at least some of the first amount of the fluid from the first portion of the wick to a second portion of the wick.

19. The method according to claim 18, wherein transferring the fluid from the first portion of the wick to the second portion of the wick includes moving the fluid distally.

20. The method according to claim 18, further including desorbing the fluid from the wick into ambient air.

* * * * *